US007544501B2

(12) United States Patent
Hovanec et al.

(10) Patent No.: US 7,544,501 B2
(45) Date of Patent: Jun. 9, 2009

(54) NITRITE-OXIDIZING BACTERIA AND METHODS OF USING AND DETECTING THE SAME

(75) Inventors: Timothy A. Hovanec, Moorpark, CA (US); Carol M. Phalen, Chatsworth, CA (US)

(73) Assignee: Aquaria, Inc., Moorpark, CA (US)

( * ) Notice: Subject to any disclaimer, the term of this patent is extended or adjusted under 35 U.S.C. 154(b) by 155 days.

(21) Appl. No.: 10/682,179

(22) Filed: Oct. 9, 2003

(65) Prior Publication Data

US 2005/0079596 A1 Apr. 14, 2005

(51) Int. Cl.
*C12N 1/20* (2006.01)
(52) U.S. Cl. ................. 435/252.1; 435/252.4; 424/93.4; 424/93.3
(58) Field of Classification Search ........................ None
See application file for complete search history.

(56) References Cited

U.S. PATENT DOCUMENTS

| | | | |
|---|---|---|---|
| 4,737,289 A | 4/1988 | Castaldi et al. | |
| 4,844,013 A | 7/1989 | de Haan et al. | |
| 4,995,980 A | 2/1991 | Jaubert | |
| 5,462,666 A | 10/1995 | Kimmel | |
| 5,462,855 A | 10/1995 | Springer et al. | |
| 6,207,440 B1 * | 3/2001 | Hovanec | 435/252.1 |
| 6,265,206 B1 | 7/2001 | Hovanec | |
| 6,268,154 B1 | 7/2001 | Hovanec | |

FOREIGN PATENT DOCUMENTS

WO    WO 99/32603 A    7/1999

OTHER PUBLICATIONS

Tal, Yossi et al., "Characterization of the microbial community and nitrogen transformation processes associated with moving bed bioreactors in a closed recirculated mariculture system," Aquaculture, Elsevier Science B.V., 2003, pp. 187-202.
Ehrich, Silke et al, "A new obligately chemolithoautotrophic, nitrate-oxidizing bacterium, *Nitrospira moscoviensis* sp. nov. and its phylogenetic relationship," Arch Microbiol, Springer-Verlag, 1995, pp. 16-23.
Hovanec, Timothy A. et al., "*Nitrospira*-Like Bacteria Associated with Nitrite Oxidation in Freshwater Aquaria," Applied and Environmental Microbiology, American Society for Microbiology, 1998, pp. 258-264.
Schmidt, Thomas M. et al., "Analysis of a Marine Picoplankton Community by 16S rRNA Gene Cloning and Sequencing," Journal of Bacteriology, American Society for Microbiology, Jul. 1991, pp. 4371-4378.
Hovanec, Timothy A. et al., "Comparative Analysis of Nitrifying Bacteria Associated with Freshwater and Marine Aquaria," Applied and Environmental Microbiology, American Society of Microbiology, Aug. 1996, pp. 2888-2896.
Teske, A. et al., "Evolutionary Relationships among Ammonia- and Nitrite-Oxidizing Bacteria," Journal of Bacteriology, American Society for Microbiology, Nov. 1994, pp. 6623-6630.
Pommerening-Roser, Andreas et al., "Phylogenetic Diversity with the Genus *Nitrosomonas*," System Appl. Microbiol., Gustav Fischer Verlag, 1996, pp. 344-351.
Kowalchuk, George A., "Analysis of Ammonia-Oxidizing Bacteria of the β Subdivision of the Class *Proteobacteria* in Coastal Sand Dunes by Denaturing Gradient Gel Electrophoresis and Sequencing of PCR-Amplified 16S Ribosomal DNA Fragments," Applied and Environmental Microbiology, American Society for Microbiology, Apr. 1997, pp. 1489-1497.
Burrell, Paul C. et al., "Microbiology of a Nitrite-Oxidizing Bioreactor," Applied and Environmental Microbiology, American Society for Microbiology, May 1998, pp. 1878-1883.
Schramm, Andreas et al., "Identification and Activities in Situ of *Nitrosospira* and *Nitrospira* spp. As Dominant Populations in a Nitrifying Fluidized Bed Reactor," Applied Environmental Microbiology, American Society for Microbiology, Sep. 1998, pp. 3480-3485.
Juretschko, Stefan et al., "Combined Molecular and Conventional Analyses of Nitrifying Bacterium Diversity in Activated Sludge: *Nitrosococcus mobilis* and *Nitrospira*-Like Bacteria as Dominant Populations," Applied and Environmental Microbiology, American Society for Microbiology, Aug. 1998, pp. 3042-3051.
Hiorns, William D., "Amplification of 16S Ribosomal RNA Genes of Autotrophic Ammonia-oxidizing Bacteria Demonstrates the Ubiquity of *Nitrosospiras* in the Environment," Microbiology, Great Britain, 1995, pp. 2793-2800.
Mobarry Bruce K. et al., "Phylogenetic Probes for Analyzing Abudance and Spatial Organization of Nitrifying Bacteria," Applied and Environmental Microbiology, American Society for Microbiology, Jun. 1996, pp. 2156-2162.
Koops, H.P. et al., "Classification of Eight New Species of Ammonia-Oxidizing Bacteria," Journal of General Microbiology, 1991, pp. 1689-1699.
Navarro, Elisabeth et al., "Characterization of Natural Populations of *Nitrobacter* spp. Using PCR/RFLP Analysis of the Ribosomal Intergenic Spacer," Archives of Microbiology, 1992, pp. 107-115.
Navarro, E. et al., "Genetic Structure of Natural Populations of *Nitrobacter* in an Aquatic Environment," Hydrobiologia, Kluwer Academic Publishers, 1995, pp. 43-48.

(Continued)

*Primary Examiner*—Irene Marx
(74) *Attorney, Agent, or Firm*—Pillsbury Winthrop Shaw Pittman LLP

(57) ABSTRACT

Described herein are nitrite-oxidizing bacteria. Particular bacteria of the present invention are tolerant of saltwater environments, saltwater environments, or both. Furthermore, in various embodiments, various bacteria of the present invention are capable of surviving a freezing or freeze-drying process, and may remain viable thereafter. Methods for preventing or alleviating the accumulation of nitrite in aqueous environments are also provided, using the nitrite-oxidizing bacteria of the present invention. Methods for detecting the bacteria of the present invention are also provided. Compositions comprising the nitrite-oxidizing bacteria of the present invention and, inter alia, ammonia-oxidizing bacteria, are also provided.

4 Claims, 15 Drawing Sheets

OTHER PUBLICATIONS

Stephen, John R. et al. "Molecular Diversity of Soil and Marine 16S rRNA Gene Sequences Related to β-Subgroup Ammonia-Oxidizing Bacteria," Applied and Environmental Microbiology, American Society for Microbiology, Nov. 1996, pp. 4147-4154.

Utaker, Janne B. et al., "Phylogenetic Analysis of Seven New Isolates of Ammonia-Oxidizing Bacteria Based on 16S rRNA Gene Sequences," System Appl. Microbiol., Gustav Fischer Verlag, 1995, pp. 549-558.

Wagner, Michael et al., "Probing Activated Sludge with Oligonucleotides Specific for Proteobacteria: Inadequacy of Culture-Dependent Methods for Describing Microbial Community Structure," Applied and Environmental Microbiology, American Society for Microbiology, May 1993, pp. 1520-1525.

Wagner, Michael et al., "Identification and in situ Detection of Gram-negative Filamentous Bacteria in Activated Sludge," System. Appl. Microbiol., Gustav Fischer Verlag Stuttgart Jena, 1994, pp. 405-417.

Wagner, Michael et al.; "In situ Identification of Ammonia-oxidizing Bacteria," System. Appl. Microbiol., Gustav Fischer Verlag Stuttgart Jena, 1995, pp. 251-264.

Wagner, Michael et al., "In situ Analysis of Nitrifying Bacteria in Sewage Treatment Plants," Wat. Sci. Tech., Elsevier Science Ltd., 1996, pp. 237-244.

Ward, B.B., "Nitrification and Denitrification: Probing the Nitrogen Cycle in Aquatic Environments," Microbial Ecology, Springer-Verlag, 1996, pp. 247-261.

Ward, B.B. et al., "Phylogenetic Diversity of Natural Populations of Ammonia Oxidizers Investigated by Specific PCR Amplification," Microbial Ecology, Springer-Verlag, 1997, pp. 87-96.

Voytek, M.A. et al., "Detection of Ammonium-Oxidizing Bacteria of the Beta-Subclass of the Class *Proteobacteria* in Aquatic Samples with the PCR," Applied and Environmental Microbiology, American Society for Microbiology, 1995, pp. 1444-1450.

Amann, Rudolf et al., "Phylogenetic Identification and In Situ Detection of Individual Microbial Cells with Cultivation," Microbiological Reviews, American Society for Microbiology, Mar. 1995, pp. 143-169.

Ehrich et al, GenEMBL Accession No. X82558, Aug. 1995.

Teske, A. et al., Evolutionary Relationships among Ammonia- and Nitrite-Oxidizing Bacteria, Journal of Bacteriology, American Society for Microbiology, vol. 176 (No. 21), pp. 6623-6630, (1994).

Hovanec, T.A. et al., Identification of Ammonia- and Nitrite-Oxidizing Bacteria Responsible for Nitrification in Saltwater Aquaria, Abstracts of the General Meeting of the American Society for Microbiology, American Society of Microbiology (Orlando, Florida), pp. 499-500, (May 21, 2001).

Hovanec, T.A. et al., Large-Scale Culture of Novel Ammonia- and Nitrite-Oxidizing Bacteria, Abstracts of the American Society for Microbiology, American Society for Microbiology (Salt Lake City, Utah), pp. 351, (May 20, 2002).

Hovanec, Timothy A. et al., Characterization of the Nitrifying Bacteria in Aquaria and Mono Lake, California, Using Molecular Methods, Dissertation Abstracts International, vol. 60 (No. 2), pp. 453, (Aug. 1999).

Regan, John A. et al., Diversity of Nitrifying Bacteria in Full-Scale Chloraminated Distribution Systems, Water Research, Elsevier Science Ltd., pp. 197-205, (2002).

Bartosch, Sabine et al., Identification of Nitrite-Oxidizing Bacteria with Monoclonal Antibodies Recognizing the Nitrite Oxidoreductase, Applied and Environmental Microbiology, American Society for Microbiology, vol. 65 (No. 9), pp. 4126-4133, (Sep. 1999).

Burrell, Paul C. et al., Identification of Bacteria Responsible for Ammonia Oxidation in Freshwater Aquaria, Applied and Environmental Microbiology, American Society for Microbiology, vol. 67 (No. 12), pp. 5791-5800, (Dec. 2001).

Utaker, Janne B. et al., Phylogenetic Analysis of Seven New Isolates of Ammonia-Oxidizing Bacteria Based on 16S rRNA Gene Sequences, Systematic and Applied Microbiology, Gustave Fischer Verlag, vol. 18 (No. 4), pp. 549-559, (1995).

Wagner, Michael et al., Identification and in situ Detection of Gram-Negative Filamentous Bacteria in Activated Sludge, Systematic and Applied Microbiology, Gustav Fischer Verlag, vol. 17 (No. 3), pp. 405-417, (1994).

Wagner, Michael et al., In situ Identification of Ammonia-Oxidixing Bacteria, Systematic and Applied Microbiology, Gustav Fischer Verlag, vol. 18 (No. 2), pp. 251-264, (1995).

Wagner, Michael et al., "In situ Identification of Ammonia-Oxidixing Bacteria," Systematic and Applied Microbiology, Gustav Fischer Verlag, vol. 18 (No. 2), p. 251-264.

Ward, B.B,, "Nitrification and Denitrification: Probing the Nitrogen Cycle in Aquatic Environments," Microbial Ecology, vol. 32 (No. 3), p. 247-261.

Teske, A., *Nitrococcus mobilis* (ATCC 25380) 16S ribosomal RNA (16S rRNA) gene, EBI Accession No. NM16SR2, pp. whole document, (Jan. 6, 1995).

\* cited by examiner

NITRITE-OXIDIZING BACTERIA AND METHODS OF USING AND DETECTING THE SAME

RELATED APPLICATIONS

This application is related to, but does not make a claim of priority from, U.S. patent application Ser. No. 10/659,983, filed Sep. 10, 2003, now U.S. Pat. No. 7,267,816, U.S. patent application Ser. No. 10/659,980, filed Sep. 10, 2003, now U.S. Pat. No. 7,270,957, U.S. patent application Ser. No. 10/659,948, filed Sep. 10, 2003, and U.S. patent application Ser. No. 10/659,965, filed Sep. 10, 2003, now abandoned, the contents of each of which is hereby incorporated by reference in its entirety as if fully set forth.

FIELD OF THE INVENTION

The invention relates generally to nitrite oxidizers and specifically to bacteria capable of oxidizing nitrite to nitrate.

BACKGROUND OF THE INVENTION

Ammonia is the principal nitrogenous waste product of teleosts and many invertebrates in both freshwater and seawater. The ammonia results from the deamination or transamination of proteins the organism receives via its diet. However, high ammonia concentrations can be toxic to many of these same aquatic organisms. In natural systems, such as lakes, rivers and oceans, the concentration of ammonia rarely reaches deleterious levels because the density of fish (and other organisms) per mass of water is low.

However, in man-made aquatic systems such as aquaculture rearing pens, tanks, raceways and ponds plus aquaria, both public and private, ammonia can reach toxic concentrations, sometimes very quickly. One reason for this is that in the above-named systems the fish density can be very large in relation to the small amount of water. Another reason is that in many of these systems the water is not continually changed; rather it recirculates through the system with only periodic partial water changes.

Therefore, most aquaculture systems and aquaria use filtration, in one form or another, to maintain a degree of water quality that is suitable for the maintenance and growth of aquatic organisms. A major component of any such filtration unit is the biological filter. The biological filter gets its name from the fact that it acts as a substrate or site for the growth of bacteria which have the capability to convert, by way of oxidation, ammonia to another compound—nitrite. High concentrations of nitrite can also be toxic but there are other species of bacteria which grow on the biological filter and oxidize the nitrite to nitrate, such as those described in U.S. Pat. Nos. 6,268,154, 6,265,206 and 6,207,440, each of which is incorporated by reference herein in its entirety as if fully set forth. Nitrate is considered non-toxic to aquatic organisms except in extreme cases of very high concentrations.

There are other situations or applications which use biological filters. These include sewage treatment facilities, wastewater treatment facilities and drinking water filtration plants. While each will have its own particular reason for using a biological filter, the goal is the same: the conversion of toxic inorganic nitrogen compounds to less harmful inorganic nitrogen substances. Biological filtration is necessary for many facilities to meet the National Recommended Water Quality Criteria as set by the Environmental Protection Agency (EPA) of the United States of America.

The oxidation of ammonia to nitrite is a process mediated by ammonia-oxidizing bacteria (AOB). Specifically, it is a two step oxidation process involving the conversion of ammonia to nitrite according to the following equations:

$$NH_3 + O_2 + H_2O + 2e^- \rightarrow NH_2OH + H_2O \quad (1)$$

$$NH_2OH + H_2O \rightarrow NO_2^- + 5H^+ + 4e^- \quad (2)$$

The oxidation of nitrite to nitrate is also a bacterially-mediated process. Specifically, it is a one step oxidation process involving the conversion of nitrite to nitrate according to the following equation:

$$NO_2^- + H_2O \rightarrow NO_3^- + 2H^+ + 4e^- \quad (1)$$

The most commonly studied nitrite oxidizing bacteria (NOB) is *Nitrobacter winogradskyi*. It was originally isolated from soils and is purported to be the active NOB in aquaculture facilities (Wheaton, F. W. 1977. Aquacultural Engineering. John Wiley & Sons, Inc. New York.), in wastewater treatment facilities (Painter, H. A. 1986. Nitrification in the treatment of sewage and waste-waters. In Nitrification J. I. Prosser ed. IRL Press. Oxford.) and in aquaria (Spotte, S. 1979. Seawater Aquariums—The Captive Environment. Wiley-Interscience. New York). These references, and all other references cited herein are hereby incorporated by reference in their entirety as if fully set forth.

However, recent research conducted with modern molecular methods which use the uniqueness of the DNA sequence of an organism (or group of organisms) has shown that *N. winogradskyi* and its close relatives were below detection limits in freshwater aquaria environments (Hovanec, T. A. and E. F. DeLong. 1996. Comparative analysis of nitrifying bacteria associated with freshwater and marine aquaria. Appl. Environ. Microbiol. 62:2888-2896.). Furthermore, research has shown that bacteria from the phylum *Nitrospira* are responsible for the oxidation of nitrite to nitrate in aquaria (Hovanec, T. A., L. T. Taylor, A. Blakis and E. F. DeLong. 1998. *Nitrospira*-like bacteria associated with nitrite oxidation in freshwater aquaria. Appl. Environ. Microbiol. 64:258-264.) and in wastewater treatment facilities (Burrell, P. C., J. Keller and L. L. Blackall. 1998. Microbiology of a nitrite-oxidizing bioreactor. Appl. Environ. Microbiol. 64:1878-1883.). However, the *Nitrospira* isolate determined to be responsible for nitrite oxidation in freshwater aquaria was not found in marine aquaria (Hovanec et. al. 1998).

*Nitrospira marina* was first discovered by Watson in 1986 (Watson, S. W., E. Bock, F. W. Valois, J. B. Waterbury, and U. Schlosser; 1986. *Nitrospira marina* gen. nov., sp. nov.: A chemolithotrophic nitrite oxidizing bacterium. Archives Microbiology, 144:1-7). However, it was not considered an important or dominant nitrite-oxidizing organism in natural (soils, marine or freshwaters nor reservoirs) or artificial environments (wastewater treatment facilities) (Abeliovich, A. 2003. The Nitrite Oxidizing Bacteria. In M. Dworkin et al. Eds. The Prokaryotes: An Evolving Electronic Resource for the Microbiological Community, third edition, release 3.13, March 2003. Springer-Verlag, New York). A second species of *Nitrospira* (*Nitrospira moscoviensis*) was isolated from a partially corroded iron pipe in a heating system of a building located in Moscow, Russia. This bacterium grew optimally at 39° C. in a non-marine medium (Abeliovich, A. 2003). It has also been reported that the microbial consortium of a marine moving bed reactor (MBB) included both AOB (*Nitrosomonas cryotolerans*) and NOB (*Nitrospira marina*), along with a number of heterotrophic bacteria. (Y. Tal, J. E. M. Watts, S. Schreier, K. R. Sowers and H. J. Schreier, 2003. Characterization of the microbial community and nitrogen transformation process associated with moving bed bioreactors in a closed recirculated mariculture system. Aquaculture 215 (2003) 187-202.)

An environmental factor of particular import with aquaria environments and wastewater treatment is salinity, and, more specifically, the numerous physicochemical differences between freshwater and saltwater environments. The distinction among various NOB in their ability to tolerate such dramatic changes in local environment is critical in the design of these systems and implementation of NOB therein. As such, a demonstrated tolerance by a particular NOB to a saltwater environment may render that NOB suitable for use in particular aquaria and wastewater environments. Moreover, an ability to withstand the change between a freshwater and saltwater environment may have even broader implications, such as suitability of a particular NOB for use in a range of environments, both freshwater and saltwater.

Furthermore, the storage and transport of NOB is often limited to liquid and similar, potentially inconvenient media, owing, at least in part, to the inability of various strains of NOB to withstand a freeze-drying process. Freeze-drying allows one to formulate a volume of NOB into a solid, freeze-dried powder or similar composition that may be tolerant of greater fluctuations in, e.g., temperature, and may be correspondingly more practical for purposes of shipping and handling in a commercialized product and for maintaining an extended shelf-life.

Thus, there exists a need in the art for the identification of NOB which are capable of tolerating a saltwater environment and/or both saltwater and freshwater environments. There is also a need in the art for NOB that remain viable after being subjected to a freeze-drying process.

SUMMARY OF THE INVENTION

In an embodiment of the present invention, isolated bacteria or bacterial strains capable of oxidizing nitrite to nitrate are provided. In one embodiment, the 16S rDNA of the bacteria or bacterial strains has the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. The nucleotide sequences described as SEQ ID NO:1 and SEQ ID NO:2 are exemplary of *Nitrococcus*-like NOB, and the nucleotide sequences described as SEQ ID NO:3, SEQ ID NO:4, SEQ ID NO:5, SEQ ID NO:6, SEQ ID NO:7, and SEQ ID NO:8 are exemplary of *Nitrospira*-like NOB. The *Nitrococcus* like NOB represented by SEQ ID NO:1 and SEQ ID NO:2 have been deposited on Aug. 28, 2003 with the American Type Culture Collection (ATCC) located at 10801 University Boulevard, Manassas, Va. 20110-2209 and have been assigned accession number PTA-5424. The *Nitrospira*-like NOB represented by SEQ ID NO:3, SEQ ID NO:4, SEQ ID NO:5, SEQ ID NO:6, SEQ ID NO:7, and SEQ ID NO:8 have been deposited on Aug. 28, 2003 with the American Type Culture Collection (ATCC) located at 10801 University Boulevard, Manassas, Va. 20110-2209 and have been assigned accession number PTA-5422.

In various embodiments, the 16S rDNA of the bacteria or bacterial strains have the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

The present invention also includes nucleic acid sequences and bacteria with sequences which have the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

For the purposes of this application, "96% similar" means that single base substitutions may occur in up to 4% of the bases, "97% similar" means that single base substitutions may occur in up to 3% of the bases, "98% similar" means that single base substitutions may occur in up to 2% of the bases and "99% similar" means that single base substitutions may occur in up to 1% of the bases.

The present invention also includes compositions capable of, inter alia, alleviating the accumulation of nitrite in a medium, wherein the compositions comprise one or more of the bacterial strains of the present invention, wherein the 16S rDNA of the bacterial strain(s) has the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

The present invention also includes methods of freeze-drying the bacteria or bacterial strains disclosed herein. The methods comprise treating the bacteria or bacterial strains with a cryoprotectant, placing them in a freezer and drying the bacteria or bacterial strains under vacuum pressure. The freeze-drying methods of the present invention produce freeze-dried NOB that can be stored in freeze-dried form while maintaining their viability and ability to oxidize nitrite to nitrate.

The present invention also includes methods of alleviating the accumulation of nitrite in a medium. The methods include a step of placing into the medium a sufficient amount of a bacterial strain or a composition comprising a bacterial strain, wherein the 16S rDNA of the bacterial strain has the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

The present invention also includes methods for detecting and determining the quantity of bacteria in a medium capable of oxidizing nitrite to nitrate. The method includes providing a detectably labeled probe of the present invention, isolating total DNA from the medium, exposing the isolated DNA to the probe under conditions wherein the probe hybridizes to only the nucleic acid of the bacteria when the 16 rDNA of the bacteria has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, and detecting and measuring the probe to detect and measure the amount of bacteria.

The present invention also includes polymerase chain reaction (PCR) primers that may be used to detect the bacteria and nucleic acid sequences of the present invention.

DETAILED DESCRIPTION OF THE INVENTION

Figure 1:
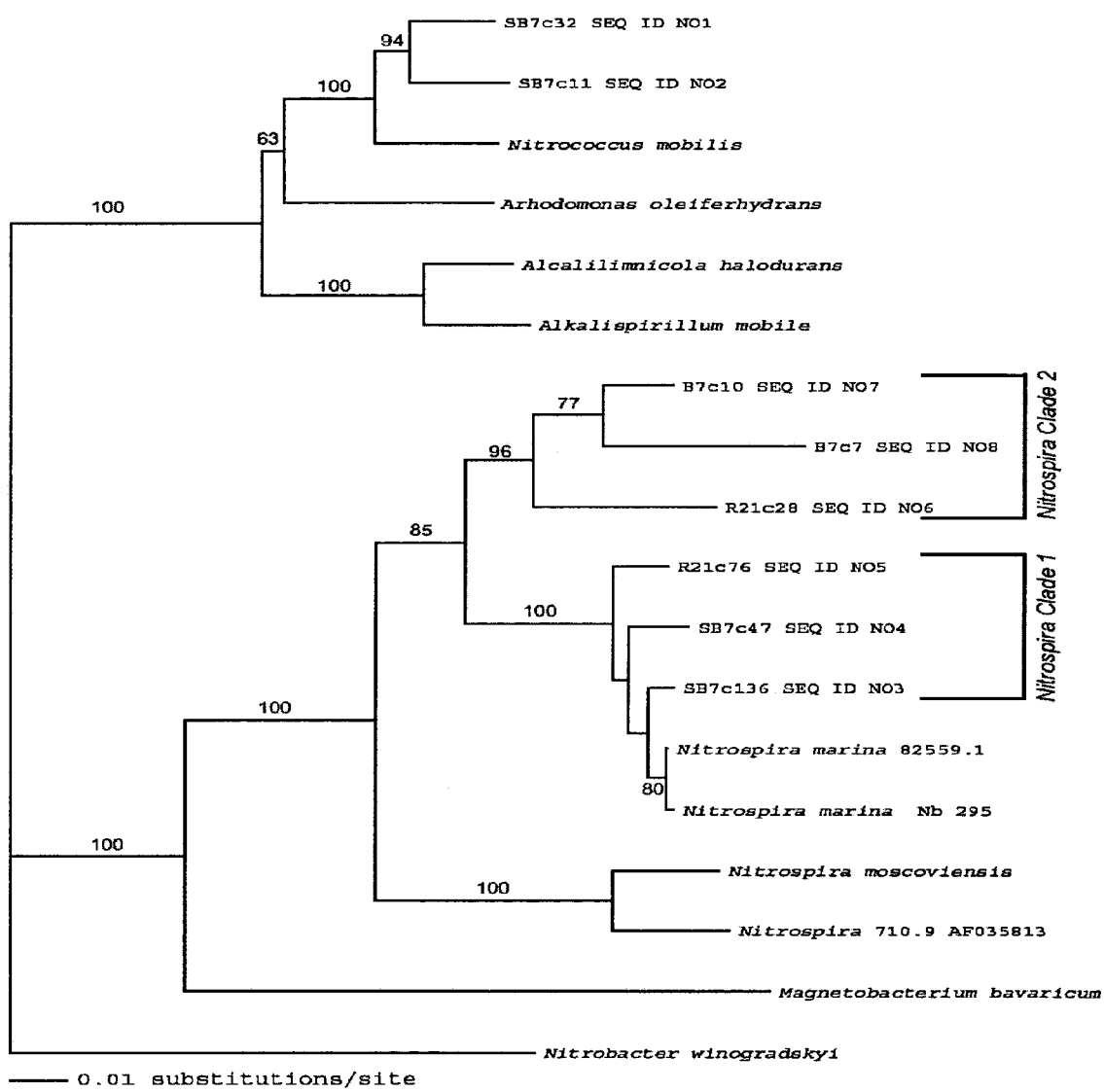
FIG. 1 illustrates the phylogenetic relationships of eight bacterial strains (i.e., those represented by SEQ ID NO:1, SEQ ID NO:2, SEQ ID NO:3, SEQ ID NO:4, SEQ ID NO:5, SEQ ID NO:6, SEQ ID NO:7, and SEQ ID NO:8) inferred from comparative analysis of 16S rDNA sequences in accordance with an embodiment of the present invention. The tree is based on neighbor-joining distance analysis of sequences containing a minimum of 1445 nucleotides.

The present invention is based upon the discovery of novel bacterial strains which are capable of nitrite oxidation in saltwater and/or freshwater environments and which can also survive and remain viable following a freezing or freeze-drying process. Embodiments of the present invention describe methods for using and detecting the bacterial strains.

The present invention provides an isolated bacterial strain or a biologically pure culture of a bacterial strain capable of oxidizing nitrite to nitrate, wherein the 16S rDNA of the bacterial strain includes the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 as shown in Tables 1 through 8.

TABLE 1

The sequence for the *Nitrococcus*-like nitrite-oxidizing bacterium represented by SB7c32.

| |  |
|---|---|
| TGATCATGGCTCAGATTGAACGCTGGCGGCATGCCTAACACATGCAAGTCGAGCGG | SEQ ID NO:1 |
| CAGCAGCGCCTTTCTTCGGAAAGGTGGCTGGCGAGCGGCGGACGGGTGAGTAACGC | |
| GTGGGAATCTACCTTCGGTGGGGGATAGCCCGGGGAAACTCGGATTAATACCGCAT | |
| ACGCCTACGGGGAAAGCGGGCCTCTGCTTGCAAGCTCGCACCGATGGATGAGCCC | |
| GCGTCCGATTAGCTAGTTGGTGGGGTAATGGCCTACCAAGGCGACGATCGGTAGCT | |
| GGTCTGAGAGGACGATCAGCCACACTGGGACTGAGACACGGCCCAGACTCCTACGG | |
| GAGGCAGCAGTGGGGAATATTGGACAATGGGCGCAAGCCTGATCCAGCAATGCCGC | |
| GTGGGTGAAGAAGGCCTGCGGGTTGTAAAGCCCTTTCAGTCGGGAGGAAAAGCATC | |
| GGGTTAATACCTCGGTGTCTTGACGTTACCGGCAGAAGAAGCACCGGCTAACTCCGT | |
| GCCAGCAGCCGCGGTAATACGGAGGGTGCAAGCGTTAATCGGAATTACTGGGCGTA | |
| AAGCGCATGTAGGCGGTCGGATAAGTCGGGTGTGAAAGCCCCGGGCTCAACCTGGG | |

TABLE 1-continued

The sequence for the *Nitrococcus*-like
nitrite-oxidizing bacterium represented by
SB7c32.

AATTGCATCCGATACTGTTTGGCTAGAGTCTGGTAGAGGGAGGCGGAATTCCCGGTG

TAGCGGTGAAATGCGTAGATATCGGGAGGAACACCAGTGGCGAAGGCGGTCTCCTG

GATCAAGACTGACGCTGAGGTGCGAAAGCGTGGGGAGCAAACAGGATTAGATACCC

TGGTAGTCCACGCCGTAAACGATGAGGACTAGCCGTTGGATTCATTAATGAGTCTAG

TGGCGCAGCTAACGCGTTAAGTCCTCCGCCTGGGGAGTACGGCCGCAAGGTTAAAA

CTCAAAGGAATTGACGGGGGCCCGCACAAGCGGTGGAGCATGTGGTTTAATTCGAT

GCAACGCGAAGAACCTTACCTGCTCTTGACATCTCCGGAACCTTACAGAGATGTGAG

GGTGCCTTCGGGAACCGGATGACAGGTGCTGCATGGCTGTCGTCAGCTCGTGTCGTG

AGATGTTGGGTTAAGTCCCGCAACGAGCGCAACCCTTGCCCCTAGTTACCAGCGGTT

CGGCCGGGGACTCTAGGGGACTGCCGGTGACAAACCGGAGGAAGGTGGGGATGA

CGTCAAGTCATCATGGCCCTTATGGGCAGGGCTACACACGTGCTACAATGGCCGGTA

CAAAGGGTTGCAAACCGTGGAGGGGAGCTAATCCCAAAAAGCCGGTCCCAGTCCGG

ATTGCAGTCTGCAACTCGACTGCATGAAGTCGGAATCGCTAGTAATCGCGGATCAGC

AATGCCGCGGTGAATACGTTCCCGGGCCTTGTACACACCGCCCGTCACACCATGGGA

GTCGGCTGCACCAGAAGTCGGTAGCCTAACCTTCTTAGGAAGGAGGGCGCTGCCCA

CGGTGTGGTCGATGACTGGGGTGAAGTCGTA.

TABLE 2

The sequence for the *Nitrococcus*-like
nitrite-oxidizing bacterium represented by
SB7c11.

| | |
|---|---|
| GATCATGGCTCAGATTGAACGCTGGCGGCATGCCTAACACATGCAAGTCGAGCGGC | SEQ ID NO:2 |

AGCAGCACCTCTCTTCGGAAAGGTGGCTGGCGAGCGGCGGACGGGTGAGTAACGCG

TGGGAATCTACCTTCGGTGGGGGATAGCCCGGGGAAACTCGGATTAATACCGCATA

CGCCTACGGGGGAAAGCGGGCCTCTGCTTGCAAGCTCGCACCGATGGATGAGCCCG

CGACCGATTAGCTAGTTGGTGGGGTAACGGCCTACCAAGGCGACGATCGGTAGCTG

GTCTGAGAGGACGATCAGCCACACTGGGACTGAGACACGGCCCAGACTCCTACGGG

AGGCAGCAGTGGGGAATATTGGACAATGGGCGCAAGCCTGATCCAGCAATGCCGCG

TGGGTGAAGAAGGCCTGCGGGTTGTAAAGCCCTTTCAGCCGGGAGGAAAAGCATCG

GGTTAATACCTCGATGTGTTGACGTTACCGGCAGAAGAAGCACCGGCTAACTCCGTG

CCAGCAGCCGCGGTAATACGGAGGGTGCAAGCGTTAATCGGAATTACTGGGCGTAA

AGCGCATGTAGGCGGTCGGATAAGTCGGGTGTGAAAGCCCCGGGCTCAACCTGGGA

ATTGCATCCGATACTGTTTGTCTAGAGTCTGGTAGAGGGAGGCGGAATTCCCGGTGT

AGCGGTGAAATGCGTAGATATCGGGAGGAACACCAGTGGCGAAGGCGGTCTCCTGG

ATCAAGACTGACGCTGAGGTGCGAAAGCGTGGGGAGCAAACAGGATTAGATACCCT

GGTAGTCCACGCCGTAAACGATGAGGACTAGCCGTTGGATTCATTAATGAGTCTAGT

GGCGCAGCTAACGCGTTAAGTCCTCCGCCTGGGGAGTACGGCCGCAAGGTTAAAAC

TCAAAGGAATTGACGGGGGCCCGCACAAGCGGTGGAGCATGTGGTTTAATTCGATG

TABLE 2-continued

The sequence for the *Nitrococcus*-like
nitrite-oxidizing bacterium represented by
SB7c11.

CAACGCGAAGAACCTTACCTGCTCTTGACATCTCCGGAACCTTGCAGAGATGTGAGG

GTGCCTTCGGGAACCGGATGACAGGTGCTGCATGGCTGTCGTCAGCTCGTGTCGTGA

GATGTTGGGTTAGGTCCCGCAACGAGCGCAACCCTTGCCCCTAGTTACCAGCGGTTC

GGCCGGGGACTCTAGGGGGACTGCCGGTGACAAACCGGAGGATGGTGGGGATGAC

GTCAAGTCATCATGGCCCTTATGAGCAGGGCTACACACGTGCTACAATGGCCGGTAC

AAAGGGTTGCAAACCGTGAGGGGGAGCTAATCCCAAAAAGCCGGTCCCAGTCCGGA

TTGCAGTCTGCAACTCGACTGCATGAAGTCGGAATCGCTAGTAATCGCGGATCAGCA

ATGCCGCGGTGAATACGTTCCCGGGCCTTGTACACACCGCCCGTCACACCATGGGAG

TCGGCTGCACCAGAAGTCGGTAGCCTAACCTTCTTAGGAAGG.

TABLE 3

The sequence for the *Nitrospira*-like
nitrite-oxidizing bacterium represented by
SB7c136.

| | |
|---|---|
| TGATCATGGCTCAGAACGAACGCTGGCGGCGCGCCTAACACATGCAAGTCGAACGA | SEQ ID NO:3 |

GAATCCGGGGCAACTCGGTAGTAAAGTGGCAAACGGGTGAGGAATACATGGGTAAC

CTGCCCTTGAGAAGGGAATAACCCGCCGAAAGGTGAGCTAATACCCTATACGCTAT

CATTTTTACGAAAAGATAGGAAAGCCAAGTCGAGGACTTGGTACTCAAGGAGGGG

CTCATGTCCTATCAGCTTGTTGGTGGGGTAACGGCCTACCAAGGCTACGACGGGTAG

CTGGTCTGAGAGGATGATCAGCCACACTGGCACTGAGATACGGGCCAGACTCCTAC

GGGAGGCAGCAGTGAGGAATATTGCGCAATGGGCGAAAGCCTGACGCAGCGACGC

CGCGTGGGGGATGAAGGTTTTCGGATTGTAAACCCCTTTCATGAGGAAAGATAAAG

TGGGTAACCACTTAGACGGTACCTCAAGAAGAAGCCACGGCTAACTTCGTGCCAGC

AGCCGCGGTAATACGAWGGTGGCGAGCGTTGTTCGGATTTACTGGGCGTAAAGAGC

ACGTAGGCGGTTGGGAAAGCCTTTTGGGAAATCTCCCGGCTTAACCGGGAAAGGTC

GAGAGGAACTACTCAGCTAGAGGACGGGAGAGGAGCGCGGAATTCCCGGTGTAGC

GGTGAAATGCGTAGATATCGGGAAGAAGGCCGGTGGCGAAGGCGGCGCTCTGGAAC

GTACCTGACGCTGAGGTGCGAAAGCGTGGGGAGCAAACAGGATTAGATACCCTGGT

AGTCCACGCCCTAAACGATGGGTACTAAGTGTCGGCGGTTTACCGTCGGTGCCGCAG

CTAACGCAGTAAGTACCCCGCCTGGGGAGTACGGCCGCAAGGTTGAAACTCAAAGG

AATTGACGGGGCCCGCACAAGCGGTGGAGCATGTGGTTTAATTCGACGCAACGCG

AGGAACCTTACCCAGGTTGGACATGCTCGTGGTACGAACCTGAAAGGGTGAGGACC

TCGAAAGGGGAGCGAGCTCAGGTGCTGCATGGCTGTCGTCAGCTCGTGCCGTGAGG

TGTTGGGTTAAGTCCCGCAACGAGCGTAACCCCTGTCTTCAGTTGCCATCGGGTCAT

GCCGAGCACTCTGAAGAGACTGCCCAGGATAACGGGGAGGAAGGTGGGGATGACG

TCAAGTCAGCATGGCCTTTATGCCTGGGGCTACACACGTGCTACAATGACCGGTACA

TABLE 3-continued

The sequence for the *Nitrospira*-like nitrite-oxidizing bacterium represented by SB7c136.

GAGGGTTGCAATCCCGCAAGGGGGAGCCAATCTCAAAAAACCGGCCTCAGTTCAGA

TTGGGGTCTGCAACTCGACCCCATGAAGGTGGAATCGCTAGTAATCGCGGATCAGC

ACGCCGCGGTGAATACGTTCCCGGGCCTTGTACACACCGCCCGTCACACCACGAAA

GTCAGCTGTACCAGAAGTCACTGGCGCCAACCTGCAAGGGAGGC.

TABLE 4

The sequence for the *Nitrospira*-like nitrite-oxidizing bacterium represented by SB7c47.

TGATCATGGCTCAGAACGAACGCTGGCGGCGCGCCTAACACATGCAAGTCGAACGA  SEQ ID NO:4

GAATCCGGGGCAACTCGGTAGTAAAGTGGCAAACGGGTGAGGAACACATGGGTAAC

CTGCCCTTGAGAAGGGAATAACCCGCCGAAAGGTGAGCTAATACCCTATACGCTAT

CATTTTTACGAAAAGATAGGAAAGCCAAGTCGAGGACTTGGTACTCAAGGAGGGG

CTCATGTCCTATCAGCTTGTTGGTGGGGTAACGGCCTACCAAGGCTACGACGGGTAG

CTGGTCTGAGAGGATGATCAGCCACACTGGCACTGAGATACGGGCCAGACTCCTAC

GGGAGGCAGCAGTGAGGAATATTGCGCAATGGGCGAAAGCCTGACGCAGCGACGC

CGCGTGGGGGATGAAGGTCTTCGGATTGTAAACCCCTTTCATGAGGAAAGATAAAG

TGGGTAACCACTTAGACGGTACCTCAAGAAGAAGCCACGGCTAACTTCGTGCCAGC

AGCCGCGGTAATACGAAGGTGGCGAGCGTTGTTCGGATTTACTGGGCGTAAAGAGC

ACGTAGGCGGTTGGGAAAGCCTTTTGGGAAATCTCCCGGCTTAACCGGGAAAGGTC

GAGAGGAACTACTCAGCTAGAGGACGGGAGAGGAGCGCGGAATTCCCGGTGTAGC

GGTGAAATGCGTAGATATCGGGAAGAAGGCCGGTGGCGAAGGCGGCGCTCTGGAAC

GTACCTGACGCTGAGGTGCGAAAGCGTGGGGAGCAAACAGGATTAGATACCCTGGT

AGTCCACGCCCTAAACGATGGGTACTAAGTGTCGGCGGTTTACCGTCGGTGCCGCAG

CTAACGCAGTAAGTACCCCGCCTGGGGAGTACGGCCGCAAGGTTGAAACTCAAAGG

AATTGACGGGGCCCGCACAAGCGGTGGAGCATGTGGTTTAATTCGACGCAACGCG

AAGAACCTTGCCCAGGTTGGACATGCTCGTGGTACGAACCTGAAAGGTGAGGACCT

CGAAAGGGGAGCGAGCTCAGGTGCTGCATGGCTGTCGTCAGCTCGTGCCGTGAGGT

GTTGGGTTAAGTCCCGCAACGAGCGTAACCCCTGTCTTCAGTTGCCATCGGGTCATG

CCGAGCACTCTGAAGAGACTGCCCAGGATAACGGGGAGGAAGGTGGGATGACGTC

AAGTCAGCATGGCCTTTATGCCTGGGGCTACACACGTGCTACAATGACCGGTACAGA

GGGTTGCAATCCCGCAAGGGGAGCCAATCTCAAAAAACCGGCCTCAGTTCAGATT

GGGGTCTGCAACTCGACCCCATGAAGGTGGAATCGCTAGTAATCGCGGATCAGCAC

GCCGCGGTGAATACGTTCCCGGGCCTTGTACACACCGCCCGTCACACCACGAAAGTC

AGCTGTACCAGAAGTCACTGGCGCCAACCTGCAAGGGAGGGCAGGTG.

TABLE 5

The sequence for the *Nitrospira*-like nitrite-oxidizing bacterium represented by R21c76.

| | |
|---|---|
| GAACGAACGCTGGCGGCGCGCCTAACACATGCAAGTCGAACGAGAATCCGGGGCA | SEQ ID NO:5 |

ACCCGGTAGTAAAGTGGCAAACGGGTGAGGAATGCATGGGCAACCTGCCCTTGAGA

AGGGAATAACCCGCCGAAAGGTGGGCTAATACCCTATACGCTATCTTCTTTTCGGAA

AAGATAGGAAAGCTTGGTCGAGGACTCGGCACTCAAGGAGGGGCTCATGTCCTATC

AGCTTGTTGGTGGGGTAACGGCCTACCAAGGCTACGACGGGTAGCTGGTCTGAGAG

GATGATCAGCCACACTGGCACTGAGATACGGGCCAGACTCCTACGGGAGGCAGCAG

TGAGGAATATTGCGCAATGGGCGAAAGCCTGACGCAGCGACGCCGCGTGGGGATG

AAGGTTTTCGGATTGTAAACCCCTTTCATGAGGAAAGATAAAGTGGGTAACCACTTA

GACGGTACCTCAAGAAGAAGCCACGGCTAACTTCGTGCCAGCAGCCGCGGTAATAC

GAAGGTGGCAAGCGTTGTTCGGATTTACTGGGCGTAAAGAGCACGTAGGCGGTTGG

GAAAGCCTCTTGGGAAATCTCCCGGCTTAACCGGGAAAGTTCGAGAGGTACTATTCA

GCTAGAGGACGGGAGAGGAGCGCGGAATTCCCGGTGTAGCGGTGAAATGCGTAGAT

ATCGGGAAGAAGGCCGGTGGCGAAGGCGGCGCTCTGGAACGTACCTGACGCTGAGG

TGCGAAAGCGTGGGGAGCAAACAGGATTAGATACCCTGGTAGTCCACGCCCTAAAC

GATGGGTACTAAGTGTCGGCGGTTTACCGTCGGTGCCGCAGCTAACGCAGTAAGTAC

CCCGCCTGGGGAGTACGGCCGCAAGGTTGAAACTCAAAGGAATTGACGGGGGCCCG

CACAAGCGGTGGAGCATGTGGTTTAATTCGACGCAACGCGAAGAACCTTACCCAGG

TTGGACATGCTCGTGGTACGAACCTGAAAGGGTGAGGACCTTGAAAGAGGAGCGAG

CTCAGGTGCTGCATGGCTGTCGTCAGCTCGTGCCGTGAGGTGTTGGGTTAAGTCCCG

CAACGAGCGTAACCCCTGTCTTCAGTTGCCATCGGGTCATGCCGAGCACTCTGAAGA

GACTGCCCAGGATAACGGGGAGGAAGGTGGGGATGACGTCAAGTCAGCATGGCCTT

TATGCCTGGGGCTACACACGTGCTACAATGACCGGTACAGAGGGTTGCAATCCCGC

AAGGGGGAGCCAATCTCAAAAAACCGGCCTCAGTTCAGATTGGGGTCTGCAACTCG

ACCCCATGAAGGTGGAATCGCTAGTAATCGCGGATCAGCACGCCGCGGTGAATACG

TTCCCGGGCCTTGTACACACCGCCCGTCACACCACGAAAGTCAGCTGTACCAGAAGT

CACTGGCGCCAACCCGCAAGGGGGGCAGGTGCCCAAGGTATGGTTGGTAATTGGGG

TGAAGTCGTAA.

TABLE 6

The sequence for the *Nitrospira*-like nitrite-oxidizing bacterium represented by R21c28.

| | |
|---|---|
| ATCCTGGCTCAGAACGAACGCTGCGGCGCGCCTAACACATGCAAGTCGAACGAGAA | SEQ ID NO:6 |

TCCGGGCAACCTGGTAGTAAAGTGGCGAACGGGTGAGGAATACATGGGTAACCTGC

CCTTGAGAATGGAATAACCTATCGAAAGATGGGCTAATACCATATACGCTTCCTGAT

TCGAGGATTGGGAAGGAAAGTCGTATCGAGGATACGGCGTTCAAGGAGGGGCTCAT

GGCCTATCAGCTTGTTGGTGGGGTAACGGCCTACCAAGGCAACGACGGGTAGCTGG

TCTGAGAGGATGATCAGCCACACTGGCACTGAGATACGGGCCAGACTCCTACGGGA

TABLE 6-continued

The sequence for the *Nitrospira*-like nitrite-oxidizing bacterium represented by R21c28.

GGCAGCAGTGAGGAATATTGCGCAATGGGCGAAAGCCTGACGCAGCGACGCCGCGT

GGGGGATGAAGGTTTTCGGATTGTAAACCCCTTTCAGGAGGAAAGATAAGGCAGGT

TACTGCCTGGACGGTACCTCCAGAAGAAGCCACGGCTAACTTCGTGCCAGCAGCCG

CGGTAATACGAAGGTGGCGAGCGTTGTTCGGATTTACTGGGCGTAAAGAGCGCGTA

GGCGGTTAGGTAAGCCTCTTGTGGAATCTCCGGCTTAACCGGGAATAGTCGAGGGTA

ACTGCTTAGCTAGAGGGCGGGAGAGGAGTGCGGAATTCCCGGTGTAGCGGTGAAAT

GCGTAGATATCGGGAAGAAGGCCGGTGGCGAAGGCGGCACTCTGGAACGCACCTGA

CGCTGAGGCGCGAAAGCGTGGGGAGCAAACAGGATTAGATACCCTGGTAGTCCACG

CCCTAAACGATGGGCACTAAGTGTCGGCGGTTTACCGCCGGTGCCGCAGCTAACGC

AGTAAGTGCCCCGCCTGGGGAGTACGGCCGCAAGGTTGAAACTCAAAGGAATTGAC

GGGGGCCCGCACAAGCGGTGGAGCATGTGGTTTAATTCGACGCAACGCGAAGAACC

TTACCCAGGTTGGACATGCAAGTAGTAAGAACCTGAAAGGGGGATGAGCCCGCAAG

GGCAGCTTGCTCAGGTGCTGCATGGCTGTCGTCAGCTCGTGCCGTGAGGTGTTGGTT

AAGTCCCGCAACGAGCGTAACCCCTGTCTTCAGTTGCCATCGGGTCATGCCGGGCAC

TCTGGAGAGACTGCCCAGGATAACGGGGAGGAAGGTGGGGATGACGTCAAGTCAGC

ATGGCCTTTATGCCTGGGGCTACACACGTGCTACAATGACCGGTACAAAGGGTTGCA

ATCCCGCAAGGGTGAGCTAATCTCAAAAAACCAGTCTCAGTTCGGATCGCAGTCTGC

AACTCGACTGCGTGAAGCTGGAATCGCTAGTAATCGGAGATCAGCACGCTCCGATG

AATACGTTCCCGGGCCTTGTACACACCGCCCGTCACACCATGGGAGTCGGCTGCTCC

AGAAGTAGTTATCTTAACCCGCAAGGAGGGAGGCTACCAAGGATCGGTCGGTGACT

GGGGTGAAGT.

TABLE 7

The sequence for the *Nitrospira*-like nitrite-oxidizing bacterium represented by B7c10.

CATGGCTCAGAACGAACGCTGCGGCGCGCCTAACACATGCAAGTCGAACGAGAATC    SEQ ID NO:7

CGGGGCAACTCGGTAGTAAAGTGGCGAACGGGTGAGGAATACATGGGTAACCTGCC

CTTGAAAGTGGAATAACCTATCGAAAGATGGGCTAATACCATATACGCTTCCTAGTT

TGCGGATTAGGAAGGAAAGTCGTATCGAGGATACGGTGTTCAAGGAGGGGCTCATG

GCCTATCAGCTTGTTGGTGGGGTAATGGCCTACCAAGGCAACGACGGGTAGCTGGTC

TGAGAGGATGATCAGCCACACTGGCACTGAGATACGGGCCAGACTCCTACGGGAGG

CAGCAGTGAGGAATATTGCGCAATGGGCGAAAGCCTGACGCAGCGACGCCGCGGG

GGGGATGAAGGTTTTCGGATTGTAAACCCCTTTCAGGAGGGAAGAAAAGCGGGTA

ACCGCCCGGACGGTACCTCCAGAAGAAGCCACGGCTAACTTCGTGCCAGCAGCCGC

GGTAATACGAAGGTGGCGAGCGTTGTTCGGATTTACTGGGCGTAAAGAGCGCGTAG

GCGGTTAGGTAAGCCTCTTGTGAAAGCTCCGGCTTAACCGGGAATGGTCGAGGGG

AACTACTTAGCTAGAGGGCGGGAGAGGAGTGCGGAATTCCCGGTGTAGCGGTGAAA

TABLE 7-continued

The sequence for the *Nitrospira*-like nitrite-oxidizing bacterium represented by B7c10.

TGCGTAGATATCGGGAAGAAGGCCGGTGGCGAAGGCGGCACTCTGGAACGCACCTG

ACGCTGAGGCGCGAAAGCGTGGGGAGCAAACAGGATTAGATACCCTGGTAGTCCAC

GCCCTAAACGATGGGCACTAAGTGTCGGCGGTTTACCGTCGGTGCCGCAGCTAACG

CAGTAAGTGCCCCGCCTGGGGAGTACGGCCGCAAGGTTGAAACTCAAAGGAATTGA

CGGGGGCCCGCACAAGCGGTGGAGCATGTGGTTTAATTCGACGCAACGCGAAGAAC

CTTACCCAGGTTGGACATGCAAGTAGTAAGAACCTGAAAGGGGATGAGCCCGCAAG

GAGCTTGCTCAGGTGCTGCATGGCTGTCGTCAGCTCGTGCCGTGAGGTGTTGGGTTA

AGTCCCGCAACGAGCGTAACCCCTGTCTTCAGTTGCCATCGGGTCATGCCGGGCACT

CTGGAGAGACTGCCCAGGATAACGGGAGGAAGGTGGGGATGACGTCAAGTCAGC

ATGGCCTTTATGCCTGGGGCTACACACGTGCTACAATGACCGGTACAAAGGGTTGCA

ATCCCGTAAGGGGGAGCTAATCTCAAAAAACCGGCCTCAGTTCAGATTGGGGTCTG

CAACTCGACCCCATGAAGGTGGAATCGCTAGTAATCGGGGATCAGCACGCCGCGGT

GAATACGTTCCCGGGCCTTGTACATATTGTdCGTCACAGCACGAAAGTCAGCTGTAC

CAGAAGTTGCTGGCGCTAACCCGTAAGGAGGCAGGTGCCCAAGGTATGGTTGGTAA

TTGGGGTGAAGTCGTAACAA.

TABLE 8

The sequence for the *Nitrospira*-like nitrite-oxidizing bacterium represented by B7c7.

| | |
|---|---|
| TTTGATCATGGCTCAGAACGAACGCTGGCGGCGCVVCTAACACATGCAAGTCGAAC | SEQ ID NO:8 |

GAGAATCCGGGGCAACTCGGTAGTAAAGTGGCGAACGGGTGAGGAATACATGGGTA

ACCTGCCCTTGAAAGTGGAATAACCTATCGAAAGATGGGCTAATACCATATACGCTT

CCTAGTTTGCGGATTAGGAAGGAAAGTCGTATCGAGGATACGGTGTTCAAGGAGGG

GCTCATGGCCTATCAGCTTGTTGGTGGGGTAATGGCCTACCAAGGCAACGACGGGTA

GCTGGTCTGAGAGGATGATCAGCCACACTGGCACTGAGATACGGGCCAGACTCCTA

CGGGAGGCAGCAGTGAGGAATATTGCGCAATGGGCGAAAGCCTGACGCAGCGACG

CCGCGTGGGGATGAAGGTTTTCGGATTGTAAACCCCTTTCAGGAGGGAAGAAAAA

GCGGGTAACCGCCCGGACGATACCTCCAGAAGAAGCCACAGCTAACTTCGTGCCAG

CAACCGCGGTAATACAAGGGTAGCGAACGTTGTTCAAATTTACTAGGCGTAAAGAG

CACATAGACAATTAGGTAAGCCTCTTGTGAAAGCTCCCGGCTTAACCGGGAATGGTC

GAGGGGAACTACTTAGCTAGAAAACAGGAGAAAAGTACGAAATTCCCAATATAACA

ATAAAATACATAAATATCAAAAAGAAGGCCGGTGGCGAAGGCGGCACTCTGGAACG

CACCTGACGCTGAGGCGCGAAAGCGTGGGGAGCAAACAGGATTAGATACCCTGGTA

GTCCACGCCCTAAACGATGGGCACTAAGTGTCGGCGGTTTACCGTCGGTGCCGCAGC

TAACGCAGTAAGTGCCCCGCCTGGGGAGTACGGCCGCAAGGTTGAAACTCAAAGGA

ATTGACGGGGGCCCGCACAAGCGGTGGAGCATGTGGTTTAATTCGACGCAACGCGA

AGAACCTTACCCAGGTTGGACATGCAAGTAGTAAGAACCTGAAAGGGGATGAGCCC

TABLE 8-continued

The sequence for the *Nitrospira*-like nitrite-oxidizing bacterium represented by B7c7.

```
GCAAGGAGCTTGCTCAGGTGCTGCATAGCTGTCGTCAACTCGTGCCATAAAGTGTTG

GGTTAAGTCCCACAACAAGCGTAACCCCTGTCTTCAGTTGCCATCGGGTCATGCCGG

GCACTCTGGAGAGACTGCCCAGGATAACGGGGAGGAAGGTGGGGATGACGTCAAGT

CAGCATGGCCTTTATGCCTGGGGCTACACACGTGCTACAATGACCGGTACAAAGGGT

TGCAATCCCGTAAGGGGAGCTAATCTCAAAAAACCGGCCTCAGTTCAGATTGGGG

TCTGCAACTCGACCCCATGAAGGTGGAATCGCTAGTAATCGCGGATCAGCACGCCG

CGGTGAATACGTTCCCGGGCCTTGTACACACCGCCCGTCACACCACGAAAGTCAGCT

GTACCAGAAGTCGCTGGCGCTAACCCGTAAGGAGGCAGGTGCCCAAGGTATGGTTG

GTAATTGGGGTGAAGTCGTAACAAGGT.
```

For the purposes of the present invention, an isolated bacterial strain is one that has undergone some degree of purification from its natural environment. A culture of a bacterium is considered to be biologically pure if at least 20% of the bacteria are from one bacterial strain. However, it is preferable if the culture is at least 33% pure, more preferable if the culture is at least 45% pure and most preferable if the culture is at least 90% pure.

The bacterial strains of the present invention may also be combined with each other, other species of bacteria, nutrients and/or other components to provide a composition for maintaining or purifying aqueous media. It may be desirable, for example, to combine the bacteria of the present invention with bacteria capable of removing other pollutants or undesirable compounds from aqueous media. Examples of such bacteria include ammonia-oxidizing bacteria (chemolithoautotrophic bacteria which oxidize ammonia to nitrite), heterotrophic bacteria (which mineralize organic material into ammonia and other substances) and other bacteria which will be known to those of skill in the art. Ammonia-oxidizing bacteria are known from the beta and gamma subdivisions of the *Proteobacteria*. Examples include species of the genera *Nitrosomonas, Nitrosospira, Nitrosolobus* and *Nitrosococcus*. Nitrate-reducing bacteria are known from the genera *Azoarcus, Pseudomonas* and *Alcaligenes*. Heterotrophic bacteria are known from the genera *Bacillus, Pseudomonas* and *Alcaligenes*. Other groups of bacteria that may be combined with the bacterial strains of the present invention include members of the *Planctomyces*. Such are available from known sources (e.g., American Type Culture Collection, 10801 University Blvd., Manassas Va. 20100, USA) or may be isolated directly from aquaria biofilters.

For example, the bacterial strains of the present invention may be combined with ammonia-oxidizing bacteria such that ammonia present in the water system would be oxidized to nitrite and the nitrite oxidized to nitrate. The added ammonia-oxidizing bacteria may be any ammonia-oxidizing bacteria known to the art or may be exemplified by, but are not in any way limited to, those ammonia-oxidizing bacteria disclosed in the following commonly assigned patent applications: U.S. patent application Ser. No. 10/659,983, filed Sep. 10, 2003, now U.S. Pat. No. 7,267,816, U.S. patent application Ser. No. 10/659,980, filed Sep. 10, 2003, now U.S. Pat. No. 7,270,957, U.S. patent application Ser. No. 10/659,948, filed Sep. 10, 2003, and U.S. patent application Ser. No. 10/659,965, filed Sep. 10, 2003, now abandoned, the contents of each of which is hereby incorporated by reference in its entirety as if fully set forth.

Another example would be to combine the bacterial strains of the present invention with aerobic or anaerobic denitrifying bacteria. In this case, the nitrate which is produced by the interaction of the bacterial strains of the present invention with denitrifying bacteria would be reduced to dinitrogen or other nitrogen based products. A third example would be to combine the bacterial strains of the present invention with heterotrophic bacteria which mineralize organic matter into simpler inorganic substances which, subsequently, can be utilized as substrates by the bacterial strains of the present invention.

In several embodiments, compositions for maintaining or purifying aqueous media are provided that comprise nitrite-oxidizing bacteria and ammonia-oxidizing bacteria. In one embodiment, a composition is provided for the maintenance of home aquaria, said composition comprising saltwater NOB of the present invention along with saltwater AOB. In one embodiment, 0.5-1.5 mL, but preferably approximately 1 mL of concentrated saltwater NOB of the present invention is mixed with 2.25-3.25 mL, but preferably approximately 2.75 mL of concentrated saltwater AOB. That concentrated mixture is then diluted to 2.5-3.5 fluid ounces, but preferably approximately 3 fluid ounces (88.7 mL) with artificial seawater, a volume designed to treat 50-60 gallons, but preferably approximately 55 gallons of aquarium water. The composition may include several strains of saltwater NOB of the present invention, wherein the 16S rDNA of the bacterial strains has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In one embodiment, the composition comprises all of the saltwater NOB strains of the present invention, with the majority of the composition being comprised of the bacterial stains represented by SEQ ID NO:6, SEQ ID NO:7 and SEQ ID NO:8 (as used here, the term "majority" means at least 50%).

In another embodiment, a composition is provided for the maintenance of public aquaria and aquaculture facilities, said composition comprising saltwater NOB of the present invention along with saltwater AOB. In one embodiment, 40-50 mL, but preferably approximately 45 mL of concentrated saltwater NOB of the present invention is mixed with 118-128 mL, but preferably approximately 123 mL of concentrated saltwater AOB. That concentrated mixture is then diluted to 0.9-1.1 gallons, but preferably approximately 1 gallon (3.79 L) with de-chlorinated, filtered water, a volume designed to treat 2410-2510 gallons, but preferably approximately 2460 gallons of aquarium or aquaculture facility water. The composition may include several strains of saltwater NOB of the present invention, wherein the 16S rDNA of the bacterial strains has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In one embodiment, the composition comprises all of the saltwater NOB strains of the present invention, with the majority of the composition being comprised of the bacterial stains represented by SEQ ID NO:6, SEQ ID NO:7 and SEQ ID NO:8 (as used here, the term "majority" means at least 50%).

The present invention also provides a mixture comprising a concentrated bacterial strain capable of oxidizing nitrite to nitrate, wherein the 16S rDNA of the bacteria has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:5, SEQ ID NO:6, SEQ ID NO:7 or SEQ ID NO:8. According to this embodiment of the invention, the bacterial strain is considered to be concentrated if the bacterial strain occurs in a concentration which is higher than its concentration occurred in nature. In general, the concentration of the bacterial strain will be at least 20% of the total cells in the sample as determined by standard techniques such as molecular probing using fluorescent in situ hybridization (FISH) techniques, which will be known to those skilled in the art, using appropriate controls and enumeration methods. More preferably, the concentration of the bacterial strain would be 33% or greater of the total cells, even more preferably 45%, and most preferably 90% or greater of the total cells. However, it may be preferable to have more than one of the bacteria which have a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 in the mixture. In this case, the percentages stated above relate to percentage of total NOBs in the mixture with the understanding that the balance of cell population might be comprised of ammonia-oxidizing bacteria or other types of bacteria.

In particular, while not wishing to be bound by any theory, of the various bacterial strains discussed in connection with the present invention, those strains represented by SEQ ID NO:1, SEQ ID NO:2, SEQ ID NO:3, SEQ ID NO:4, SEQ ID NO:5, SEQ ID NO:6, SEQ ID NO:7, and SEQ ID NO:8 are believed to be especially tolerant of saltwater environments; although these strains may be utilized in freshwater environments, as well, and are believed to function effectively therein. Bacterial strains and mixtures incorporating strains other than those strains represented by SEQ ID NO:1, SEQ ID NO:2, SEQ ID NO:3, SEQ ID NO:4, SEQ ID NO:5, SEQ ID NO:6, SEQ ID NO:7, and SEQ ID NO:8 may also tolerate saltwater environments to an appreciable degree, yet in a preferred embodiment of the present invention, it is those strains represented by SEQ ID NO:1, SEQ ID NO:2, SEQ ID NO:3, SEQ ID NO:4, SEQ ID NO:5, SEQ ID NO:6, SEQ ID NO:7 or SEQ ID NO:8 that are included in a saltwater environment to oxidize nitrite to nitrate.

Furthermore, while any of the bacterial strains discussed in connection with the present invention may be freeze-dried, those strains represented by SEQ ID NO:1, SEQ ID NO:2, SEQ ID NO:3, SEQ ID NO:4, SEQ ID NO:5, SEQ ID NO:6, SEQ ID NO:7, and SEQ ID NO:8 are believed to be particularly tolerant of the freeze-drying process, as evidenced by their ability to remain viable after such a process, and to oxidize nitrite to nitrate following such a process. Thus, in an embodiment of the present invention, those bacterial strains represented by SEQ ID NO:1, SEQ ID NO:2, SEQ ID NO:3, SEQ ID NO:4, SEQ ID NO:5, SEQ ID NO:6, SEQ ID NO:7 or SEQ ID NO:8 may be freeze-dried and thereafter used to oxidize nitrite to nitrate in saltwater environments.

In another embodiment, methods of freeze-drying the bacteria or bacterial strains disclosed herein are provided. The methods comprise treating the bacteria or bacterial strains with a cryoprotectant, placing them in a freezer and drying the bacteria or bacterial strains under vacuum pressure. The freeze-drying methods of the present invention produce freeze-dried NOB that can be stored in freeze-dried form while maintaining their viability and ability to oxidize nitrite to nitrate after thawing.

In several embodiments, the methods of freeze-drying the bacteria or bacterial strains of the present invention comprise particular freeze-drying conditions. In one embodiment, NOB strains of the present invention are grown in a medium with a salinity of 30 ppt. The NOB are then treated with trehalose as a cryoprotectant, with 40-60 g, but preferably approximately 50 g of trehalose being mixed with 900-1100 mL, but preferably approximately 1000 mL of NOB for an approximately 5% solution. The NOB solutions are stored at approximately 4° C. until processing, whereupon they are poured onto pre-refrigerated trays and frozen at approximately −40° C. for approximately 3 hours. The frozen solutions are then placed in a drier at a mild primary sublimination rate for approximately 12 hours with a finishing temperature of approximately 27° C. with a total drying time of approximately 35 hours. In another embodiment, the freeze-drying conditions are identical, except for the fact that the frozen solutions are placed in a drier at an aggressive primary sublimination rate for approximately 2 hours with a finishing temperature of approximately 27° C. with a total drying time of approximately 28 hours.

In another embodiment, NOB strains of the present invention are grown in a medium with a salinity of 30 ppt. The NOB are then treated with trehalose as a cryoprotectant, with 90-110 g, but preferably approximately 100 g of trehalose being mixed with 900-1100 mL, but preferably approximately 1000 mL of NOB for an approximately 10% solution. The NOB solutions are stored at approximately 4° C. until processing, whereupon they are poured onto pre-refrigerated trays and frozen at approximately −40° C. for approximately 3 hours. The frozen solutions are then placed in a drier at a mild primary sublimination rate for approximately 12 hours with a finishing temperature of approximately 27° C. In another embodiment, the freeze-drying conditions are identical, except for the fact that the frozen solutions are placed in a drier at an aggressive primary sublimination rate for approximately 2 hours with a finishing temperature of approximately 27° C.

It is understood that the bacterial strains, mixtures and compositions of the present invention can be in the form of powder, liquid, a frozen form, a freeze-dried form or any other suitable form, which may be readily recognized by one of skill in the art. These are commonly referred to as "commercial additives," and may include, but are in no way limited to:

(1) a liquid form, wherein one or more of the strains, mixtures or compositions are in a liquid solution containing inorganic salts or organic compounds such that the viability of the cells is not destroyed during the course of storage;

(2) a frozen form, wherein one or more of the strains, mixtures or compositions are in a liquid mixture as above, optionally including cryoprotectant compounds to prevent cell lysis, which is frozen and stored at a temperature at or below 32° F.; and (3) a powder form, which has been produced by freeze-drying or other means, wherein the dehydrated form of one or more of the strains, mixtures or compositions can be stored at normal room temperature without loss of viability.

Obtaining a proper form of the bacterial strains and the mixtures of the present invention is well within the skill in the art in view of the instant disclosure. It is also understood that the bacterial strains and the mixtures of the present invention can be used alone, or in combination with other components. Examples of such components include, but are not limited to, ammonia-oxidizing bacteria, heterotrophic nitrite-oxidizing bacteria, heterotrophic ammonia-oxidizing bacteria and the like. All of the forms of the biologically pure bacterial strains may also contain nutrients, amino acids, vitamins and other compounds which serve to preserve and promote the growth of the bacterial strains. The bacterial strains and the mixtures and compositions of the present invention can be used in freshwater aquaria, seawater aquaria and wastewater to alleviate the accumulation of nitrite. They can also be used in a bioremediation process to reduce the level of pollution caused by the nitrite. A bioremediation process, also called bioaugmentation, includes, but is not limited to, the supplemental addition of microorganisms to a system (e.g. a site where biological or chemical contamination has occurred) for the purposes of promoting or establishing biological and/or chemical processes that result in the change of one or more forms of chemical compounds present in the original system.

Accordingly, one aspect of the present invention provides a method of alleviating the accumulation of nitrite in a medium. The method includes a step of placing into the medium a sufficient amount of one or more bacterial strains of the present invention capable of oxidizing nitrite to nitrate to alleviate the accumulation of nitrite in the medium, wherein the 16S rDNA of the bacterial strain(s) has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:5, SEQ ID NO:6, SEQ ID NO:7 or SEQ ID NO:8. The amount of the bacterial strain(s) is sufficient if the added bacteria can alleviate or prevent the accumulation of nitrite in the medium. In general, the addition of one or more of the bacterial strains of the invention to a freshwater or saltwater aquarium is expected to reduce the maximum nitrite concentration by at least 50% when compared to the level which would be attained in the absence of the bacterial strain(s).

In another embodiment of the invention, a method of alleviating the accumulation of nitrite in a medium includes placing into the medium a sufficient amount of a composition, as disclosed herein, for alleviating the accumulation of nitrite in a medium. The composition may comprise one or more bacterial strains of the present invention capable of oxidizing nitrite to nitrate wherein the 16S rDNA of the bacterial strain or strains has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

In various embodiments, methods of maintaining or purifying aqueous media are provided that include placing into the medium a sufficient amount of a composition, as disclosed herein, for maintaining or purifying a aqueous medium. In said compositions, the bacterial strains of the present invention may be combined with ammonia-oxidizing bacteria such that ammonia present in the water system would be oxidized to nitrite and the nitrite oxidized to nitrate. Another example would be to combine the bacterial strains of the present invention with aerobic or anaerobic denitrifying bacteria. In this case, the nitrate which is produced by the interaction of the bacterial strains of the present invention with denitrifying bacteria would be reduced to dinitrogen or other nitrogen based products. A third example would be to combine the bacterial strains of the present invention with heterotrophic bacteria which mineralize organic matter into simpler inorganic substances which, subsequently, can be utilized as substrates by the bacterial strains of the present invention.

In several embodiments, methods of maintaining or purifying aqueous media are provided that comprise placing into the medium a sufficient amount of a composition that comprises nitrite-oxidizing bacteria and ammonia-oxidizing bacteria. In one embodiment, a method of maintaining home aquaria is provided that comprises placing into the aquaria a sufficient amount of a composition, said composition comprising saltwater NOB of the present invention along with saltwater AOB. In one embodiment, the composition is formed by mixing 0.5-1.5 mL, but preferably approximately 1 mL of concentrated saltwater NOB of the present invention is mixed with 2.25-3.25 mL, but preferably approximately 2.75 mL of concentrated saltwater AOB. That concentrated mixture is then diluted to 2.5-3.5 fluid ounces, but preferably approximately 3 fluid ounces (88.7 mL) with artificial seawater, a volume designed to treat 50-60 gallons, but preferably approximately 55 gallons of aquarium water. The composition may include several strains of saltwater NOB of the present invention, wherein the 16S rDNA of the bacterial strains has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In one embodiment, the composition comprises all of the saltwater NOB strains of the present invention, with the majority of the composition being comprised of the bacterial strains represented by SEQ ID NO:6, SEQ ID NO:7 and SEQ ID NO:8 (as used here, the term "majority" means at least 50%).

In another embodiment, a method of maintaining public aquaria and aquaculture facilities is provided that comprises placing into the aquaria or aquaculture facility a sufficient amount of a composition, said composition comprising saltwater NOB of the present invention along with saltwater AOB. In one embodiment, the composition is formed by mixing 40-50 mL, but preferably approximately 45 mL of concentrated saltwater NOB of the present invention is mixed with 118-128 mL, but preferably approximately 123 mL of concentrated saltwater AOB. That concentrated mixture is then diluted to 0.9-1.1 gallons, but preferably approximately 1 gallon (3.79 L) with de-chlorinated, filtered water, a volume designed to treat 2410-2510 gallons, but preferably approximately 2460 gallons of aquarium or aquaculture facility water. The composition may include several strains of saltwater NOB of the present invention, wherein the 16S rDNA of the bacterial strains has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In one embodiment, the composition comprises all of the saltwater NOB strains of the present invention, with the majority of the composition being comprised of the bacterial stains represented by SEQ ID NO:6, SEQ ID NO:7 and SEQ ID NO:8 (as used here, the term "majority" means at least 50%).

It will be appreciated that the actual levels achieved in a given setting will be a function of the size and contents of the systems (i.e., the number of fish, plants, etc.). In a newly set-up 37 liter aquarium with ten fish, the nitrite concentration may reach 14 mg/L or higher without addition of the bacterial strain, whereas the maximum level can be reduced to about 5 mg/L by addition of one or more of the bacterial strains. In general, the maximum nitrite concentration would not be expected to exceed 3 mg/L if one or more of the bacterial strains of the invention is added to such a system. When the system reaches a steady state, the nitrite levels drop back to below 0.5 mg/L, a process which occurs more rapidly when one or more of the bacterial strains of the invention is present.

In one embodiment of the present invention, the bacterial strains and compositions of the present invention are placed directly into a medium such as, but not limited to, freshwater aquaria, seawater aquaria and wastewater. In another embodiment of the present invention, the bacterial strains and compositions may be grown on a rotating biological contactor and then placed in the medium. In a different embodiment, the bacterial strains and compositions of the present invention can be placed on a biofilter unit contained in the medium. In another embodiment the bacterial strains and compositions of the present invention may be immobilized in an immobilizing polymer, such as, but not limited to, acrylamide, alginate or carrageenan. This bacterial-laced polymer material may then be placed in a filter or may itself be placed in the filter stream of a suitable facility.

As used herein, the term "aquarium" is intended to mean a container which may be made of, in combination or in its entirety, but not limited to, glass, plastic, or wood that holds water and in which living aquatic organisms (such as fish, plants, bacteria and invertebrates) are placed, and the contents thereof. An aquarium may be for the purposes of displaying aquatic organisms, for their short or long-term holding, for scientific study, for transportation and other purposes. A freshwater aquarium is generally an aquarium in which the liquid medium has a salinity of less than 15 parts per thousand. A saltwater aquarium is generally an aquarium in which the liquid medium has a salinity of more than 15 parts per thousand. The term "aquarium water" is used to refer to the medium which is contained within the aquarium, and its associated filter systems, in which the aquatic organisms reside. Aquarium water may contain a wide range of inorganic or organic chemical substances and, therefore, may have a wide range of parameters such as concentration of salts, pH, total dissolved solids and temperature, to name a few.

As used herein, "wastewater" generally refers to a liquid medium which is the product of an industrial or human process. It may require treatment by one or more filtration methods to render it less harmful to the environment such that it conforms to discharge standards as determined by a governmental agency. Wastewater may also be recycled such that it is not discharged to the environment.

As used herein, a "biological filter," also called a "biofilter," generally refers to a filter type whose purpose is to promote the growth of microorganisms, or to provide a substrate for the attachment and growth of microorganisms. A biofilter may be part of an aquarium filtration system or a wastewater filtration system. As used herein, the term "rotating biological contactor" generally refers to a type of biofilter which rotates in the water or medium. It may be completely or partially submerged in the water or medium. Persons skilled in the art will recognize rotating biological contactors as embodied in U.S. Pat. Nos. 2,085,217; 2,172,067; 5,423,978; 5,419,831; 5,679,253; 5,779,885 and all continuations, improvements and foreign counterparts; each of which is incorporated herein by reference as if fully set forth.

As used herein, "filter floss" refers to irregularly shaped natural or synthetic multi-stranded material which may serve as a biofilter, a mechanical filter or a combination of these.

As used herein, "aquarium gravel" refers to a substrate commonly placed inside, on the bottom, of an aquarium. It may be composed of irregular or regular shaped pieces of rock, coral, plastic or other material. It may serve as a biofilter, a mechanical filter, for decorative purposes or a combination of these.

As used herein, the term "filter sponge" refers to a natural or synthetic material which when used in an aquarium or as part of an aquarium filtration system may serve as a mechanical filter, a biofilter or both.

As used herein, "plastic filter media" refers to a man-made material which serves as a biofilter, a mechanical filter or both. It may be plastic molded or injection molded.

In another embodiment, nucleic acid sequences and bacteria with sequences which have the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:5, SEQ ID NO:6, SEQ ID NO:7 or SEQ ID NO:8 are also provided.

In another embodiment, oligonucleotide probes are provided for detecting and measuring the amount of bacteria of the present invention which are present in a medium. The probes have the nucleotide sequences set forth in SEQ ID NO:14, SEQ ID NO:15, SEQ ID NO:16 and SEQ ID NO:18. The oligonucleotide probes of the present invention can be synthesized by methods which are known in the art.

The oligonucleotide probes of the present invention can be labeled by any labels that are detectable. Examples of suitable labels include, but are in no way limited to, radioactive labels, fluorescent labels, and the like. Suitable labeling materials are commercially available and would be known to those of ordinary skill in the art. The methods of labeling an oligonucleotide or a polynucleotide are also known to those of ordinary skill in the art (See, for e.g., Sambrook, J., E. F. Fritsch, and T. Maniatis. Molecular Cloning—A Laboratory Manual, second edition, 1989, Cold Spring Harbor Press).

The oligonucleotide probes of the present invention are able to hybridize with 16S rDNA of the bacterial strain of the present invention. Accordingly, the oligonucleotide probes of the present invention are well suited for use in a method for detecting and determining the quantity of bacteria of the present invention.

In one aspect of the present invention, a method is provided for detecting and determining the quantity of bacteria capable of oxidizing nitrite to nitrate in a medium, wherein the 16S rDNA of the bacteria has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. The method may include:
  (a) providing a detectably labeled probe of the present invention with a nucleotide sequence set forth in SEQ ID NO:14, SEQ ID NO:15, SEQ ID NO:16 or SEQ ID NO:18;

(b) isolating total DNA from a medium;
(c) exposing the isolated total DNA to the detectably labeled probe under conditions under which the probe hybridizes to only the nucleic acid of the bacteria, wherein the 16S rDNA of the bacteria has a nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8; and
(d) detecting and measuring the hybridized probe for detecting and measuring the quantity of the bacteria.

The probes of the present invention are represented by SEQ ID NO:14, SEQ ID NO:15, SEQ ID NO:16 and SEQ ID NO:18. A sequence that is at least 96% similar over the entire length of any of the aforementioned probes may also be used to detect the bacteria of the present invention. These probes are further described in the ensuing examples.

The medium can be aquarium water, wherein the DNA is isolated therefrom. The medium can also contain a material such as aquarium gravel, sponge filter material, filter floss, or plastic filter media, but is not considered to be limited to these. Accordingly, the DNA can be isolated from the above and other sources where such bacteria may be expected to be found.

The method of the present invention can be performed in conjunction with a DNA chip, or similar tools known to those of skill in the art. A DNA chip may include a solid carrier and a group of nucleotide derivatives or their analogues fixed to the solid carrier via covalent bonding. Detection of a nucleic acid fragment with a DNA chip is generally performed using a probe oligonucleotide which is complementary to the nucleic acid fragment to be detected, by way of hybridization. The probe oligonucleotide is generally fixed onto the solid carrier (e.g., solid substrate). In the detection process, a nucleic acid fragment in a sample liquid may be provided with a fluorescent label or a radioisotope label, and then the sample liquid may be brought into contact with the probe oligonucleotide of the DNA chip. If the labeled nucleic acid fragment in the sample liquid is complementary to the probe oligonucleotide, the labeled nucleic acid fragment is combined with the probe oligonucleotide by hybridization. The labeled nucleic acid fragment fixed to the DNA chip by hybridization with the probe oligonucleotide may then be detected by an appropriate detection method such as, by way of example, fluorometry or autoradiography, although other methods for detection may be utilized.

The method may alternatively be performed in conjunction with a wide variety of automated processes, which will readily recognized by those of skill in the art, and implemented by routine experimentation. By way of example, the method of the present invention may be performed with DNA or protein microarrays, biosensors, bioprobes, capillary electrophoresis, and real-time PCR to name some common methodologies; although it will be readily appreciated by one of skill in the art that this list in not all-inclusive.

The detection method of the present invention provides an effective tool for one to monitor and detect the occurrence of bacteria capable of oxidizing nitrite to nitrate in a medium. The method also provides a tool for one to check the commercial additives to determine the effectiveness of the additives, by measuring the occurrence or the amount of the bacteria of the present invention.

In another embodiment, PCR primers are provided that may be used to detect the bacteria and nucleic acid sequences of the present invention. The PCR primer pairs are represented by SEQ ID NO:19 and SEQ ID NO:20 and SEQ ID NO:21 and SEQ ID NO:22. A sequence that is at least 96% similar over the entire length of any of the aforementioned PCR primers may also be used to detect the bacteria of the present invention. These PCR primers are further described in the ensuing examples.

It would be readily apparent to one skilled in the art that variants of the aforementioned oligonucleotide probes and PCR primers that still may be used to detect the bacteria and nucleic acid sequences of the present invention are within the scope of the present invention. For example, a variant of any of the oligonucleotide probes or primers that differs from SEQ ID NO:14, SEQ ID NO:15, SEQ ID NO:16, SEQ ID NO:18, SEQ ID NO:19, SEQ ID NO:20, SEQ ID NO:21 or SEQ ID NO:22 due to one or more nucleotide additions, deletions or substitutions, but still may be used to detect the bacteria and nucleic acid sequences of the present invention, is encompassed by the present invention.

The present invention includes isolated bacteria, isolated bacterial strains, bacterial cultures and nucleotide sequences comprising the sequences identified herein as SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or variants of those sequences. Particularly preferred variants are those in which there is a high degree of similarity to SEQ ID NO:1, SEQ ID NO:2, SEQ ID NO:3, SEQ ID NO:4, SEQ ID NO:5, SEQ ID NO:6, SEQ ID NO:7 or SEQ ID NO:8. The present invention includes variants that are at least 96% similar, at least 97% similar, at least 98% similar or at least 99% similar to SEQ ID NO:1, SEQ ID NO:2, SEQ ID NO:3, SEQ ID NO:4, SEQ ID NO:5, SEQ ID NO:6, SEQ ID NO:7 or SEQ ID NO:8. It is appreciated in the art that disclosures teaching those skilled in the art how to make and use a reference sequence (such as SEQ ID NO:1, SEQ ID NO:2, SEQ ID NO:3, SEQ ID NO:4, SEQ ID NO:5, SEQ ID NO:6, SEQ ID NO:7 or SEQ ID NO:8) will also be sufficient to teach such an individual to make and use the described variants.

Three commonly-assigned patents describing nitrite-oxidizing bacteria, methods of using the bacteria and methods of detecting the bacteria issued in the United States (see U.S. Pat. Nos. 6,207,440, 6,265,206 and 6,268,154). All three patents describe a nucleotide sequence and any variants that have greater than 96.1% homology to that sequence. The issuance of these patents demonstrates that specifications setting forth particular sequences and describing particular variants enable one skilled in the art to make and use the sequence and its described variants. In addition, it is common in the art that patents disclosing nucleotide sequences also disclose and claim variants of those sequences (see, e.g. U.S. Pat. Nos. 6,465,621, 6,509,170 and 6,573,066).

Variants of particular nucleotide sequences may be naturally-occurring polymorphisms or synthetic sequence alterations (see, e.g. U.S. Pat. No. 6,485,938). A great diversity of modifications to nucleotide sequences, both natural and synthetic, are common and well known in the art, along with methods for making the synthetic variants (see, e.g. U.S. Pat. Nos. 6,448,044 and 6,509,170). Methods for comparing the similarity of two or more nucleotide sequences are well known in the art. Similar sequences are often identified using computer programs such as BESTFIT and BLAST (see, e.g., U.S. Pat. No. 6,461,836). Further, hybridization may be used to detect the similarity between variant sequences and a reference sequence (see, e.g., U.S. Pat. No. 6,573,066). Thus, one skilled in the art would be able to easily synthesize and identify nucleotide sequences that are variants of a reference sequence by using known techniques. Therefore, a specification that describes a nucleotide sequence and its variants allows one skilled in the art to make and use that sequence and its variants.

EXAMPLES

A series of assays and experiments were conducted to isolate, identify and show the efficacy of the bacterial strains reported herein. They involved a variety of bacterial culturing techniques, molecular biological analyses of DNA extracted from samples of the cultures, molecular biological analysis of the bacterial strains, and the application of concentrated cultures of the bacterial strains in liquid and freeze-dried form to aquaria to measure their ability to control nitrite concentrations.

Example 1

Bacteria Culturing

Bacterial culturing vessels (termed reactors) were constructed and seeded with bacterial biomass gathered from operating aquaria. Each reactor received 4.95 L of a mineral salt solution (made up in distilled water) containing 50 g $KH_2PO_4$, 50 g $K_2HPO_4$, 18.75 g $MgSO_4.7H_2O$, 1.25 g $CaCl_2.2H_2O$ and 1 g $FeSO_4.7H_2O$. Air was provided such that the dissolved oxygen was equal to or greater than 7.5 mg/L, stirring was provided, and the reactors were kept in a darkened cabinet at approximately 28° C.

For the isolation and culturing of strains of NOB of the present invention in saltwater environments, synthetic sea salts (INSTANT OCEAN, Aquarium Systems Inc., Mentor, Ohio) were added to reach a salt concentration of between 28 and 33 ppt.

The ammonia and nitrite concentrations were measured daily using flow injection analysis (FIA, Tecator FIASTAR 5010 system) while pH was determined with an electrode (Denver Instruments Model 225 pH/ISE meter and associated pH/ATC electrode). Salinity was measured with a YSI Model 30 Salinity, Temperature, Conductivity probe. Nitrate was measured periodically and the data were used to determine when water changes were required. Bacterial biomass was retained in the reactors during water changes because the biomass is very floccular in nature. Thus prior to decanting 50% of the reactor's volume through the appropriate sampling port, the biomass was settled by turning off both the air and the stirring mechanism for one hour. Additionally, reactors were periodically scrubbed to remove the biomass from the surfaces and thereby return the biomass to suspension. Microbiological samples were taken routinely for DNA extraction (for PCR) and cell fixation (for FISH) for further analysis.

Example 2

Nucleic Acid Sampling and Extraction

For DNA extraction, samples of appropriate biological filtration media were taken and resuspended in cell lysis buffer (40 mM EDTA. 50 mM Tris-HCl, pH 8.3). Samples were stored at −20° C. or −74° C. until extraction. For processing, lysozyme was added to the samples to a final concentration of 10 mg/ml. After incubation at 37° C. for 90 minutes, 20% sodium dodecyl sulfate (SDS) was added to a final concentration of 1%. Then the samples were subjected to four freeze/thaw cycles followed by the addition of proteinase K (stock concentration, 10 mg/ml) to a final concentration of 2 mg/ml and incubated at 70° C. for 35 minutes. In some cases, additional proteinase K and SDS were added and the sample was incubated at 55° C. for another 30 minutes.

After cell lysis, DNA was extracted using EASY DNA extraction kit (Qiagen Inc., Santa Clarita, Calif.; hereinafter "Qiagen"). DNA was eluted to a 50 µl volume and quantified by Hoechst type 33258 dye binding and fluorometry (DY-NAQUANT 200, Hoefer Pharmacia Biotech Inc., San Francisco, Calif.).

Example 3

Clone Libraries of PCR Amplified rRNA Genes

Clone libraries were derived from DNA extracts from biomass samples taken from reactors and aquaria. Bacterial ribosomal RNA gene fragments from bacteria represented by the sequences SEQ ID NO:1, SEQ ID NO:2, SEQ ID NO:3, SEQ ID NO:4, SEQ ID NO:5, SEQ ID NO:6, SEQ ID NO:7, and SEQ ID NO:8 were amplified with the primers S-D-Bact-0011-a-S-17 (8f; GTT TGA TCC TGG CTC AG) (SEQ ID NO:9) and 1492r (eubacterial; GGT TAC CTT GTT ACG ACT T) (SEQ ID NO:10). PCR conditions, cycle parameters, and reaction components were as previously described (De-Long, E. F. 1992. Archaea in coastal marine environments. Proc. Natl. Acad. Sci. USA 89: 5685-5689.) PCR products were evaluated by agarose gel electrophoresis. PCR fragments were cloned with a TA Cloning kit (Invitrogen, Carlsbad, Calif.), as described in the manufacturer's directions, after rinsing with TE buffer and concentrating to 30 µl with a CENTRICON concentrator (Amicon, Inc. Beverly, Mass.).

Example 4

Sequencing and Phylogenetic Analysis

The 16S rDNA inserts from each clone that comprised the clone library were screened by restriction enzyme analysis (REA) using the restriction enzyme Hae III in order to ensure that the 16S rDNA insert was amplifiable and determine whether the 16S rDNA possessed a unique REA pattern when digested with the Hae III enzyme. If a clone was amplifiable and possessed a unique REA pattern, then the clone's plasmid containing the 16S rDNA insert of interest was partially sequenced. The amplified PCR 16S rDNA template of each clone selected for sequencing was cleaned using the PCR Purification Kit Catalog No. 28142 (Qiagen). Sequencing was performed using a LICOR 4000L automated DNA sequencer on template cycle-sequenced with fluorescently labeled primers and SEQUITHERM EXCEL II DNA Sequencing kits (Epicentre Technologies, Madison, Wis.).

Up to two or three clones of the same REA pattern were partially sequenced to ensure that they were identical. Many clones were fully sequenced and phylogenetically analyzed by PAUP (Phylogenetic Analysis Using Parsimony ver 4.0b2a, D. L. Swofford) (bootstrap values and distance analysis), ARB (A Software Environment for Sequence Date, W. Ludwig and O. Strunk) (phylogenetic tree) and Phylip (Phylogeny Inference Package J. Felsentein) (similarity matrix). Primers and probes for the clone of interest from the clone libraries were developed using ARB probe design and probe match programs as well as after manual alignment. Primers and probes were double checked with BLAST (S. F. Altschul et al. 1990. Basic local alignment tool. J. Mol. Biol. 215:403-410). The specificity of the primers was determined by using them on DNA extracted from clones and pure cultures of known bacteria. The specificity of the probes was tested using pure cultures of known bacteria and samples from the reactors.

Example 5

DGGE Analysis and Profiling

For general eubacterial DGGE analysis, rDNA fragments were amplified using the forward 358f (eubacterial; CCT ACG GGA GGC AGC AG) (SEQ ID No:11) with a 40-bp GC-clamp on the 5' end as described by Murray et al. (A. Murray et al. 1996. Phylogenetic compositions of bacterioplankton from two California estuaries compared by denaturing gradient gel electrophoresis of 16S rDNA fragments. Appl. Environ. Microbiol. 62:2676-2680), and the reverse primer S-*-Univ-0519-a-A-18 (519r: GWA TTA CCG CGG CKG CTG) (SEQ ID NO:12). For specific NOB DGGE, the forward primer of 358f (SEQ ID No:11) with a 40-bp GC-clamp on the 5' end was used with the reverse primer NSP685 (NSP685: CAC CGG GAA TTC CGC GCT CCT C) (SEQ ID NO:13). The PCR conditions were the same and were performed on a ROBOCYCLER GRADIENT 96 (Stratagene, La Jolla, Calif.) using the TAQ PCR core kit (Qiagen). PCR conditions included a hot start (80° C.) and a touchdown procedure. Initial denaturation at 94° C. for 3 min. was followed by a denaturation at 94° C. for 1 min., a touchdown annealing from 65° C. to 55° C. for 1 min. 29 sec. (the annealing time during the touchdown increased by 1.4 sec. per cycle) and primer extension at 72° C. for 56 sec. (the extension time was increased 1.4 sec. per cycle). The final temperature series of the above thermal cycle was repeated for 20 total cycles, followed by a final extension at 72° C. for 5 min. Amplicons were examined by agarose gel electrophoresis.

DGGE was performed with a Bio-Rad D-GENE System (Bio-Rad Laboratories, Hercules, Calif.; hereinafter "Bio-Rad"). Gels were 8.5% acrylamide/Bis using Bio-Rad reagents (D GENE Electrophoresis Reagent Kit, Bio-Rad). Gel gradients were poured using Bio-Rad reagents (D GENE Electrophoresis Reagent Kit, Bio-Rad) with a denaturing gradient of 25% to 55% (where 100% denaturant is a mixture of 40% deionized formamide and 7 M urea) and the Bio-Rad gradient delivery system (Model 475, Bio-Rad) unless otherwise noted. All gels were run at 200 volts for 6 hours. For documentation purposes some gels were stained in Vistra Green (diluted 1:10,000) (Molecular Dynamics, Sunnyvale, Calif.; hereinafter "Molecular Dynamics") for 20 min., followed by a 20 min. wash in 1×TAE buffer, and then scanned using a FLUORIMAGER SI (Molecular Dynamics).

Individual bands were excised from the DGGE gels using alcohol-sterilized scalpels. Extraction of DNA from the gel followed the methods of Ferris et al. (M. J. Ferris et al. 1996. Denaturing gradient gel electrophoresis profiles of 16S rRNA-defined population inhabiting a hot spring microbial mat community. Appl.Environ. Microbiol. 62: 340-346.). The excised band was placed in a sterile 2 ml screw cap tube with 500 µl sterile deionized water. The tubes were half-filled with glass beads (cat. no.11079-101, Biospec Products Inc., Bartlesville, Okla.; hereinafter "Biospec") and placed in a mechanical bead beater (MINI-BEADBEATER-8, Biospec) for 3 min. at the highest setting. The processed DNA remained in the tubes at 4° C. overnight. After overnight storage, the tubes were centrifuged at 3,200×g for 8 minutes at 4° C. to concentrate the gel fragments. The supernatant was transferred to a clean eppendorf tube.

To check the extraction efficiency, the supernatant was sometimes re-amplified with the DGGE primers and re-analyzed by DGGE. An extraction was considered acceptable if it yielded a single band in DGGE analysis which co-migrated with the original DGGE band in the mixed population sample. The nucleotide sequence of the excised band was sequenced by the previously described methods using fluorescently labeled primers.

Example 6

Oligonucleotide Probe Development

Oligonucleotide probes labeled with fluorescent dyes were designed that specifically hybridize with the 16S rRNA gene sequence isolated from closely related bacteria from reactors in this study. One probe, SNOBTP (GTT GCC CCG GAT TCT CGT TC) (SEQ ID NO:14), targets all *Nitrospira*-like bacteria found in this study, which are represented by the sequences of SEQ ID NO:3, SEQ ID NO:4, SEQ ID NO:5, SEQ ID NO:6, SEQ ID NO:7 and SEQ ID NO:8 to the exclusion of other nitrite-oxidizers represented by the sequences of SEQ ID NO:1 and SEQ ID NO:2 (the *Nitrococcus*-like bacteria), and also to the exclusion of the alpha subdivision proteobacteria nitrite-oxidizers represented by *Nitrobacter winogradskyi*. This probe has been used successfully with either Cy-3 or fluorescein-ON (Qiagen Inc., USA) dyes with a formamide percentage of 20%.

A second probe, NSP685 (CAC CGG GAA TTC CGC GCT CCT C) (SEQ ID NO:15), can be used to target a specific clade of *Nitrospira*-like bacteria (designated Clade 1) which is represented by the sequences of SEQ ID NO:3, SEQ ID NO:4 and SEQ ID NO:5. Probe NSP685 (SEQ ID NO:15) is labeled with the fluorescent dye Cy-3 and during the hybridization procedure two additional probes are added to the reaction. These two additional probes are SNTSP2 (CAC CGG GAA TTC CGC ACT CCT C) (SEQ ID NO:16) which is labeled with fluorescein-ON (Qiagen Inc., USA) and EUBAC338 (GCT GCC TCC CGT AGG AGT) (SEQ ID NO:17) which is also labeled with fluorescein-ON. The percentage formamide is 55%. In this manner the Clade 1 *Nitrospira*-like nitrite oxidizing bacteria are the only organisms visible in the field of view of the microscope.

A third probe combination can be used to target another specific clade of *Nitrospira*-like bacteria (designated Clade 2) which is represented by the sequences of SEQ ID NO:6, SEQ ID NO:7 and SEQ ID NO:8. This involves using probe SNTSP2 (SEQ ID NO:16) which is labeled with fluorescein-ON in combination with two other probes: NSP685 (SEQ ID NO:15), labeled with Cy-3, and EUBAC338 (SEQ ID NO:17), which is also labeled with Cy-3. The percentage formamide is 55. In this manner the Clade 2 *Nitrospira*-like nitrite oxidizing bacteria are the only organisms visible in the field of view of the microscope.

A fourth probe, MOBP (CTC GCC AGC CAC CTT TCC GAA) (SEQ ID NO:18), targets *Nitrococcus*-like nitrite-oxidizing organisms, which are represented by SEQ ID NO:1 and SEQ ID NO:2, to the exclusion of all *Nitrospira*-like nitrite-oxidizing organisms and also to the exclusion of the alpha subdivision proteobacteria nitrite-oxidizers represented by *Nitrobacter winogradskyi*. The percentage formamide is 20 with this probe and the dye employed is Cy-3.

Probe matches were initially screened using BLAST (S. F. Altschul et al. 1990. Basic local alignment tool. J. Mol. Biol. 215:403-410) and CHECK_PROBE (B. L. Maidak et al. 1994. The ribosomal database project. Nucleic Acids Res. 22:3485-3487.). Probes were synthesized by Operon Tech, Inc. (Alameda, Calif.). The nucleotide sequences of the probes are shown in Table 9.

TABLE 9

The nucleotide sequences and positions of oligonucleotide probes and PCR primer sets for nitrite-oxidizing bacteria.

| Probe | Base Sequence (5' to 3') | % forma-mide | Annealing Temp (° C.) | Target Group |
|---|---|---|---|---|
| SNOBTP SEQ ID NO: 14 | GTT GCC CCG GAT TCT CGT TC | 20 | — | SEQ ID NO:3, SEQ ID NO:4, SEQ ID NO:5, SEQ ID NO:6, SEQ ID NO:7 & SEQ ID NO:8 |
| NSP685 SEQ ID NO: 15 | CAC CGG GAA TTC CGC GCT CCT C | 55 | — | SEQ ID NO:3 SEQ ID NO:4 & SEQ ID NO:5 |
| SNTSP2 SEQ ID NO: 16 | CAC CGG GAA TTC CGC ACT CCT C | 55 | — | SEQ ID NO:6 SEQ ID NO:7 & SEQ ID NO:8 |
| MOBP SEQ ID NO: 18 | CTC GCC AGC CAC CTT TCC GAA | 20 | — | SEQ ID NO:1 & SEQ ID NO:2 |
| SNTSPTf Forward primer SEQ ID NO: 19 | TCC GGG GCA ACC YGG TA | — | 49 | SEQ ID NO:3, SEQ ID NO:4, SEQ ID NO:5, |
| SNTSPTr Reverse primer SEQ ID NO: 20 | TCM CCC TTT CAG GTT C | — | | SEQ ID NO:6, SEQ ID NO:7 & SEQ ID NO:8 |
| NitroMf Forward primer SEQ ID NO: 21 | TTC GGA AAG GTG GCT GGC GAG | — | 60 | SEQ ID NO:1 & SEQ ID NO:2 |
| NitroMr Reverse primer SEQ ID NO: 22 | ATC TCT GYA AGG TTC CGG AG | — | | |

The stringency for the probes (SEQ ID NO:14, SEQ ID NO:15, SEQ ID NO:16 and SEQ ID NO:18) was determined though a series of FISH experiments at differing formamide concentrations using the reactor biomass as a positive control for the bacterial sequences herein (SEQ ID NO:1, SEQ ID NO:2, SEQ ID NO:3, SEQ ID NO:4, SEQ ID NO:5, SEQ ID NO:6, SEQ ID NO:7, or SEQ ID NO:8). In situ hybridization of the fixed, immobilized cells was carried out in a hybridization solution consisting of 0.9 M NaCl, 20 mM Tris/HCl (pH 7.4), 0.01% sodium dodecyl sulphate (SDS), 25 ng of oligonucleotide probe, and varying amounts of formamide. Slides were incubated in an equilibrated humidity chamber at 46° C. for 90 to 120 min. The hybridization solution was rinsed off with a pre-warmed (48° C.) wash solution. The slides were then incubated in the wash solution for 15 min. at 48° C. To achieve the same stringency during the washing step, as in the hybridization step, the wash solution contained 20 mM Tris/HCl (pH 7.4), 0.01% SDS, 5 mM EDTA, and NaCl. The concentration of NaCl varied according to the percent formamide used in the solution. For 20% formamide the NaCl concentration was 215 mM, for 30% it was 120 mM, and for 40% the NaCl concentration was 46 mM. Cells were detected using an AXIOSKOP 2 epifluorescence microscope (Carl Zeiss, Jena, Germany) fitted with filter sets for FITC/FLUO3 and HQ CY3. The optimum stringency was determined to be 20% formamide for the SNOBTP probe (SEQ ID NO:14). For the NSP685 and SNTSP2 tri-labeled probes (SEQ ID NO:15, SEQ ID NO:16, respectively) the optimum stringency was determined to be 55% formamide for each. The optimum stringency was determined to be 20% formamide for the MOBP probe represented by SEQ ID NO:18.

Example 7

PCR Primer Development

A set of PCR primers (SEQ ID NO:19 and SEQ ID NO:20) was developed which specifically detects *Nitrospira*-like bacteria of the sequences of the present invention (Table 9). A second set of PCR primers (SEQ ID NO:21 and SEQ ID NO:22) was developed which specifically detects *Nitrococcus*-like bacteria of the sequences of the present invention (Table 9). One set (SEQ ID NO:19 and SEQ ID NO:20) specifically detects *Nitrospira*-like bacteria including the 16S rDNA sequence set forth in SEQ ID NO:3, SEQ ID NO:4, SEQ ID NO:5, SEQ ID NO:6, SEQ ID NO:7, and SEQ ID NO:8 to the exclusion of other nitrite-oxidizing bacteria (Table 10). The second set (SEQ ID NO:21 and SEQ ID NO:22) specifically detects the *Nitrococcus*-like bacteria including the 16S rDNA sequence set forth in SEQ ID NO:1 and SEQ ID NO:2 to the exclusion of other nitrite-oxidizing bacteria (Table 10). PCR conditions were as previously described in Example 5, except the annealing temperature was modified as described in Table 10.

TABLE 10

Results of the PCR primer development specificity testing and annealing temperature experiments.

| Clone No. Or Tank No. | *Nitrococcus*-like NOB SEQ ID NO: 1 AND SEQ ID NO: 2 | | | | | *Nitrospira*-like NOB SEQ ID NO: 3, SEQ ID NO: 4 SEQ ID NO: 5 SEQ ID NO: 6, SEQ ID NO: 7 AND SEQ ID NO: 8 | | | | |
|---|---|---|---|---|---|---|---|---|---|---|
| Annealing Temp(° C.) | 56 | 58 | 60 | 62 | 64 | 43 | 45 | 47 | 49 | 51 |
| SB10 NOB Tank | + | + | + | + | +/− | +/− | +/− | +/− | +/− | + |
| SB2 NOB Tank | + | + | + | + | +/− | +/− | +/− | +/− | +/− | + |
| SB7 AOB Tank | + | + | + | + | +/− | − | − | +/− | +/− | + |
| SB4 AOB Tank | + | + | + | + | +/− | − | − | − | − | − |
| SB7c32 SEQ ID NO: 1 | + | + | + | + | +/− | − | − | − | − | − |
| SB7c11 SEQ ID NO: 2 | + | + | + | + | +/− | − | − | − | − | − |
| SB7c136 SEQ ID NO: 3 | − | − | − | − | − | + | + | + | + | + |

TABLE 10-continued

Results of the PCR primer development specificity testing
and annealing temperature experiments.

| Clone No. Or Tank No. | Nitrococcus-like NOB SEQ ID NO: 1 AND SEQ ID NO: 2 | | | | | Nitrospira-like NOB SEQ ID NO: 3, SEQ ID NO: 4 SEQ ID NO: 5 SEQ ID NO: 6, SEQ ID NO: 7 AND SEQ ID NO: 8 | | | | |
|---|---|---|---|---|---|---|---|---|---|---|
| Annealing Temp(° C.) | 56 | 58 | 60 | 62 | 64 | 43 | 45 | 47 | 49 | 51 |
| SB7c47 SEQ ID NO: 4 | − | − | − | − | − | + | + | + | + | + |
| R21c76 SEQ ID NO: 5 | − | − | − | − | − | + | + | + | + | + |
| R21c28 SEQ ID NO: 6 | − | − | − | − | − | + | + | + | + | + |
| B7c10 SEQ ID NO: 7 | − | − | − | − | − | + | + | + | + | + |
| B7c7 SEQ ID NO: 8 | − | − | − | − | − | + | + | + | + | |

"+" strong signal,
"−" no signal,
"+/−" weak signal

The specificity of each primer set was optimized by conducting a PCR experiment with each primer set using the temperature gradient mode of the Stratagene ROBOCYCLER. In this mode one can run a single experiment of all the reactions at up to 12 different annealing temperatures. Typically, the experiments were conducted at 4 to 6 different temperatures with 2° C. increasing interval. Each PCR primer set was tested against clone product with a nucleotide sequence of SEQ ID NO: 1, SEQ ID NO:2, SEQ ID NO:3, SEQ ID NO:4, SEQ ID NO: 5, SEQ ID NO:6, SEQ ID NO:7 or SEQ ID NO:8. Table 9 presents the PCR primer sets, and the optimal annealing temperature results are shown in Table 10.

Example 8

Similarity Analysis

Three clone libraries were constructed from saltwater nitrifying biomasses in order to determine the identity of the nitrite oxidizer(s) responsible for oxidation of nitrite to nitrate. Details about the biomasses are presented in Table 11.

TABLE 11

Details regarding the reactors and aquaria from which biomass
was extracted and clone libraries were constructed.

| Clone library | Details of Nitrifying Biomass |
|---|---|
| P4 | This reactor was seeded with 20 liter of material from the sump of biofarm 15 which was a saltwater biomass whose salinity was maintained at between 30 and 35 ppt. This reactor was fed at 5 mg/L ammonia-nitrogen. |

TABLE 11-continued

Details regarding the reactors and aquaria from which biomass
was extracted and clone libraries were constructed.

| Clone library | Details of Nitrifying Biomass |
|---|---|
| SB7 | This reactor was seeded with material from the sumps of biofarm 5 and 15 which were saltwater biomasses whose salinity was maintained at between 30 and 35 ppt. This reactor was fed at 5 mg/L ammonia-nitrogen. |
| B7 | This reactor was seeded with material from the sumps of biofarm 5 and 15 which were saltwater biomasses whose salinity was maintained at between 30 and 35 ppt. This reactor was fed at 5 mg/L ammonia-nitrogen. |

The clone library data show that there are two groups of nitrite-oxidizing bacteria that exist in the test ammonia fed reactors. The two types of nitrite-oxidizing bacteria are the *Nitrospira*-like organisms and the *Nitrococcus*-like microorganisms (Table 12). However, only the *Nitrospira*-like NOB are found in all three clones libraries. The percentage of clones identified as *Nitrospira*-like NOB ranged from 3.11 to 33.33 of the total clones screened. *Nitrococcus*-like NOB were found in two of three clones libraries at a percentage of 2.56 and 8.70 of the total clones screened (Table 12).

TABLE 12

Number of clones which fell into different phylogenetic
groups within the three clone libraries developed for
nitrite-oxidizing bacteria.

| Clone Library | P4 | B7 | SB7 |
|---|---|---|---|
| No. Clones Screened | 84 | 156 | 161 |
| No. Clones partially or fully sequenced | 37 | 103 | 95 |
| *Nitrosomonas* sp | 26 (30.95) | 14 (8.97) | 28 (17.39) |
| *Nitrospira*-like NOB | 28 (33.33) | 17 (10.90) | 5 (3.11) |
| *Nitrococcus*-like NOB | 0 | 4 (2.56) | 14 (8.70) |
| Alpha proteobacteria | + | + | + |
| Beta proteobacteria | + | + | + |
| Gamma proteobacteria | + | + | + |
| OP11 group | — | + | — |
| *Planctomyces* | — | + | + |
| *Actinobacterium* | — | + | — |
| *Acidobacterium* | — | + | — |

"+" present;
"—" not present.
Percent of total clones screened given in parentheses.

A similarity ranking was conducted for the eight clonal sequences described herein (SEQ ID NO:1, SEQ ID NO:2, SEQ ID NO:3, SEQ ID NO:4, SEQ ID NO:5, SEQ ID NO:6, SEQ ID NO:7 and SEQ ID NO:8) using RDP (Maidak, B. L., J. R. Cole, C. T. Parker, Jr, G. M. Garrity, N. Larsen, B. Li, T. G. Lilbum, M. J. McCaughey, G. J. Olsen, R. Overbeek, S. Pramanik, T. M. Schmidt, J. M. Tiedje and C. R. Woese. A new version of the RDP (Ribosomal Database Project). Nucleic Acids Res. 27:171-173 (1999)) (Table 13).

TABLE 13

Similarity ranking for nitrite-oxidizing clones isolated fr m reactors and aquaria
% Similarity to rDNA of:

| rDNA source | SB7c32 Nitrococcus- like | SB7c11 Nitrococcus- like | SB7c136 Nitrospira- like | SB7c47 Nitrospira- like | R21c76 Nitrospira- like | R21c28 Nitrospira- like |
|---|---|---|---|---|---|---|
| SB7c32 *Nitrococcus*-like SEQ ID NO: 1 | — | | | | | |

TABLE 13-continued

Similarity ranking for nitrite-oxidizing clones isolated from reactors and aquaria % Similarity to rDNA of:

| | | | | | | |
|---|---|---|---|---|---|---|
| SB7c11 Nitrococcus-like SEQ ID NO: 2 | 0.992 | — | | | | |
| SB7c136 Nitrospira-like SEQ ID NO: 3 | 0.795 | 0.792 | — | | | |
| SB7c47 Nitrospira-like SEQ ID NO: 4 | 0.796 | 0.794 | .997 | — | | |
| R21c76 Nitrospira-like SEQ ID NO: 5 | 0.801 | .798 | .985 | .984 | — | |
| R21c28 Nitrospira-like SEQ ID NO: 6 | 0.796 | .793 | .922 | .920 | .923 | — |
| B7c10 Nitrospira-like SEQ ID NO: 7 | 0.792 | .787 | .940 | .939 | .940 | .959 |
| B7c7 Nitrospira-like SEQ ID NO: 8 | 0.769 | .765 | .917 | .915 | .916 | .931 |
| Nitrococcus mobilis | 0.989 | 0.989 | .795 | .795 | .802 | .797 |
| Nitrospira marina (82559.1) | 0.797 | 0.796 | .992 | .992 | .987 | .922 |
| Nitrospira-like (AF035813) | 0.791 | 0.790 | .897 | .897 | .898 | .882 |
| Nitrospira moscoviensis | 0.793 | 0.793 | .894 | .894 | .894 | .885 |

| rDNA source | B7c10 Nitrospira-like | B7c7 Nitrospira-like | Nitrococcus mobilis | Nitrospira marina (82559.1) | Nitrospira-like (AF035813) | Nitrospira moscoviensis |
|---|---|---|---|---|---|---|
| SB7c32 Nitrococcus-like SEQ ID NO: 1 | | | | | | |
| SB7c11 Nitrococcus-like SEQ ID NO: 2 | | | | | | |
| SB7c136 Nitrospira-like SEQ ID NO: 3 | | | | | | |
| SB7c47 Nitrospira-like SEQ ID NO: 4 | | | | | | |
| R21c76 Nitrospira-like SEQ ID NO: 5 | | | | | | |
| R21c28 Nitrospira-like SEQ ID NO: 6 | | | | | | |
| B7c10 Nitrospira-like SEQ ID NO: 7 | — | | | | | |
| B7c7 Nitrospira-like SEQ ID NO: 8 | .963 | — | | | | |
| Nitrococcus mobilis | .766 | .789 | — | | | |
| Nitrospira marina (82559.1) | .916 | .940 | .799 | — | | |
| Nitrospira-like (AF035813) | .867 | .893 | .794 | .898 | — | |
| Nitrospira moscoviensis | .895 | .870 | .797 | .897 | .963 | — |

The similarity analysis revealed one group of clones (represented by SEQ ID NO:1 and SEQ ID NO:2) to be 98.9% similar to *Nitrococcus mobilis* (Table 13).

The similarity analysis revealed that there are two clades of *Nitrospira*-like NOB of the present invention (represented by SEQ ID NO:3, SEQ ID NO:4, SEQ ID NO:5, SEQ ID NO:6, SEQ ID NO:7 and SEQ ID NO:8). Clade 1 includes NOB represented SEQ ID NO:3, SEQ ID NO:4 and SEQ ID NO:5. Within Clade 1, the NOB represented by SEQ ID NO:3 and SEQ ID NO:4 are 99.2% similar to *Nitrospira marina* and the NOB represented by SEQ ID NO:5 are 98.7% similar to *Nitrospira marina*. Clade 2 includes NOB represented by SEQ ID NO:6, SEQ ID NO:7 and SEQ ID NO:8. Within Clade 2, the NOB represented by SEQ ID NO:6 are 92.2% similar to *Nitrospira marina*, the NOB represented by SEQ ID NO:7 are 91.6% similar to *Nitrospira marina* and the NOB represented by SEQ ID NO:8 are 94.0% similar to *Nitrospira marina*.

Phylogenetic analysis of the sequences by construction of tree using neighbor joining distance analysis and bootstrap analysis supports the results of the similarity analysis (FIG. 1). The phylogenetic results show a very high probability of SEQ ID NO:1 and SEQ ID NO:2 being similar to each other with the closest known relative being *Nitrococcus mobilis*. However, the results also demonstrate that of SEQ ID NO:1 and SEQ ID NO:2 are not *Nitrococcus mobilis*.

The phylogenetic results also support the conclusion that there are two separate clades of saltwater *Nitrospira*-like NOB which are distinct from known *Nitrospira* bacteria (FIG. 1). Clade 1, represented by SEQ ID NO:3, SEQ ID NO:4 and SEQ ID NO:5 are clearly distinct from the clade 2, represented by SEQ ID NO:6, SEQ ID NO:7 and SEQ ID NO:8. The clade 1 saltwater *Nitrospira*-like NOB have *Nitrospira marina* as a closest relative.

As an example, there is no question that the Clade 2 saltwater *Nitrospira*-like NOB (SEQ ID NO:6, SEQ ID NO:7 and SEQ ID NO:8) are at least one new species of bacteria. The similarity analysis shows their closest relative (*Nitrospira marina*) to be at most 94.0% similar (in the case of SEQ ID NO:8). The phylogenetic analysis shows these 3 sequences to be clearly distinct from all known *Nitrospira* bacteria (FIG. 1). BLAST analysis shows that *Nitrospira marina* is the closest bacteria in the database to these sequences, but the sequence of *Nitrospira marina* is clearly different than the sequences represented by SEQ ID NO:6, SEQ ID NO:7 and SEQ ID NO:8, as evidenced by the similarity and phylogenetic analyses.

The similarity rankings given in Table 13 are a guide to determining the uniqueness of the bacterial strains. There are no hard and fast rules for defining a new bacterial species. However, as examples, the ammonia-oxidizing bacteria *Nitrosolobus multiformis* and *Nitrosovibrio tenuis*, which have a similarity ranking of 0.989, are recognized by all microbiological authorities as distinct species, as are *Nitrosolobus multiformis* and *Nitrososphira briensis* (similarity ranking of 0.980). The bacterial strains represented by SEQ ID NO:3 and SEQ ID NO:4 have a similarity ranking of 0.992 when compared to *Nitrospira marina*. This similarity ranking is slightly higher than the 0.989 discussed above, but SEQ ID NO:3 and SEQ ID NO:4 are still sufficiently distinct from *Nitrospira marina* to constitute novel and unique species.

Therefore, the totality of the clone data, the PCR results, the phylogenetic analysis, the DGGE data and similarity ranking demonstrate that the bacterial strains reported herein are unique and distinct from known nitrite-oxidizing bacteria.

Example 9

Analysis of Bacteria and Experimental Results

Clonal members of *Nitrospira*-like NOB were found in all three of the saltwater enrichments for which clone libraries were developed (Table 12). The *Nitrospira*-like NOB represent a significant portion of the total clones identified, ranging from just over 3% (SB7) to greater than 33% (P4) of the total clones.

The *Nitrococcus*-like NOB were found in only 2 of the 3 clone libraries (Table 12) and at lower number than the *Nitrospira*-like NOB. In sample B7 less than 3% of the clones were identified as *Nitrococcus*-like NOB while in sample SB7 the percentage was 14. No *Nitrococcus*-like NOB were found in sample P4 (Table 12).

Example 10

Denaturing Gradient Gel Electrophoresis Survey of Clones and Reactors

Figure 2:
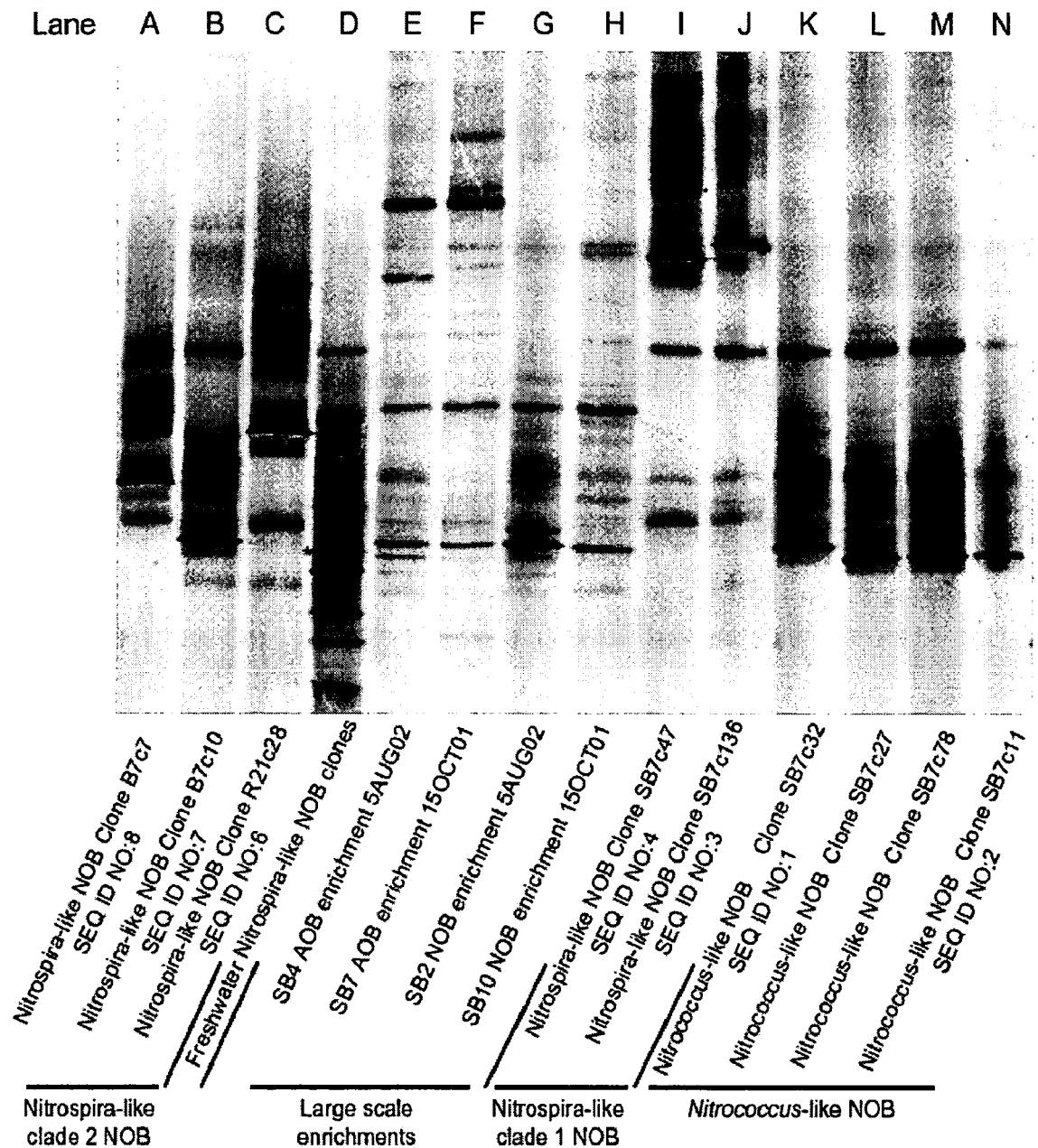
FIG. 2 illustrates a denaturing gradient gel electrophoresis (DGGE) of biomasses from selected enrichments and nitrite-oxidizing bacteria represented by SEQ ID NO:1, SEQ ID NO:2, SEQ ID NO:3, SEQ ID NO:4, SEQ ID NO:6, SEQ ID NO:7, and SEQ ID NO:8, in accordance with an embodiment of the present invention.

The novelty of various bacterial strains reported herein is further demonstrated by the results of the denaturing gradient gel electrophoresis (DGGE) testing. FIG. 2 shows the DGGE results for clone representatives for the *Nitrococcus*-like NOB (SEQ ID NO:1 and SEQ ID NO:2) and both clade 1 (SEQ ID NO:3, SEQ ID NO:4 and SEQ ID NO:5) and clade 2 (SEQ ID NO:6, SEQ ID NO:7 and SEQ ID NO:8) of the *Nitrospira*-like NOB along with enrichments of ammonia- and nitrite-oxidizing bacteria. The results show that there is a slight difference in the migration distance in the gel between SEQ ID NO:1 and SEQ ID NO:2 (*Nitrococcus*-like NOB). The band locations for the three clade 2 *Nitrospira*-like clones (SEQ ID NO:6, SEQ ID NO:7 and SEQ ID NO:8) are also different, which is expected since there are slight sequence differences in the 16S rRNA gene (Tables 6-8). Furthermore, when comparing the band locations of the four enrichments on FIG. 2, (Lanes E, F, G and H) it is difficult to distinguish whether the bands in the gel for these enrichments line up with SEQ ID NO:1 (*Nitrococcus*-like NOB) or SEQ ID NO:7 (*Nitrospira*-like NOB).

Figure 3:
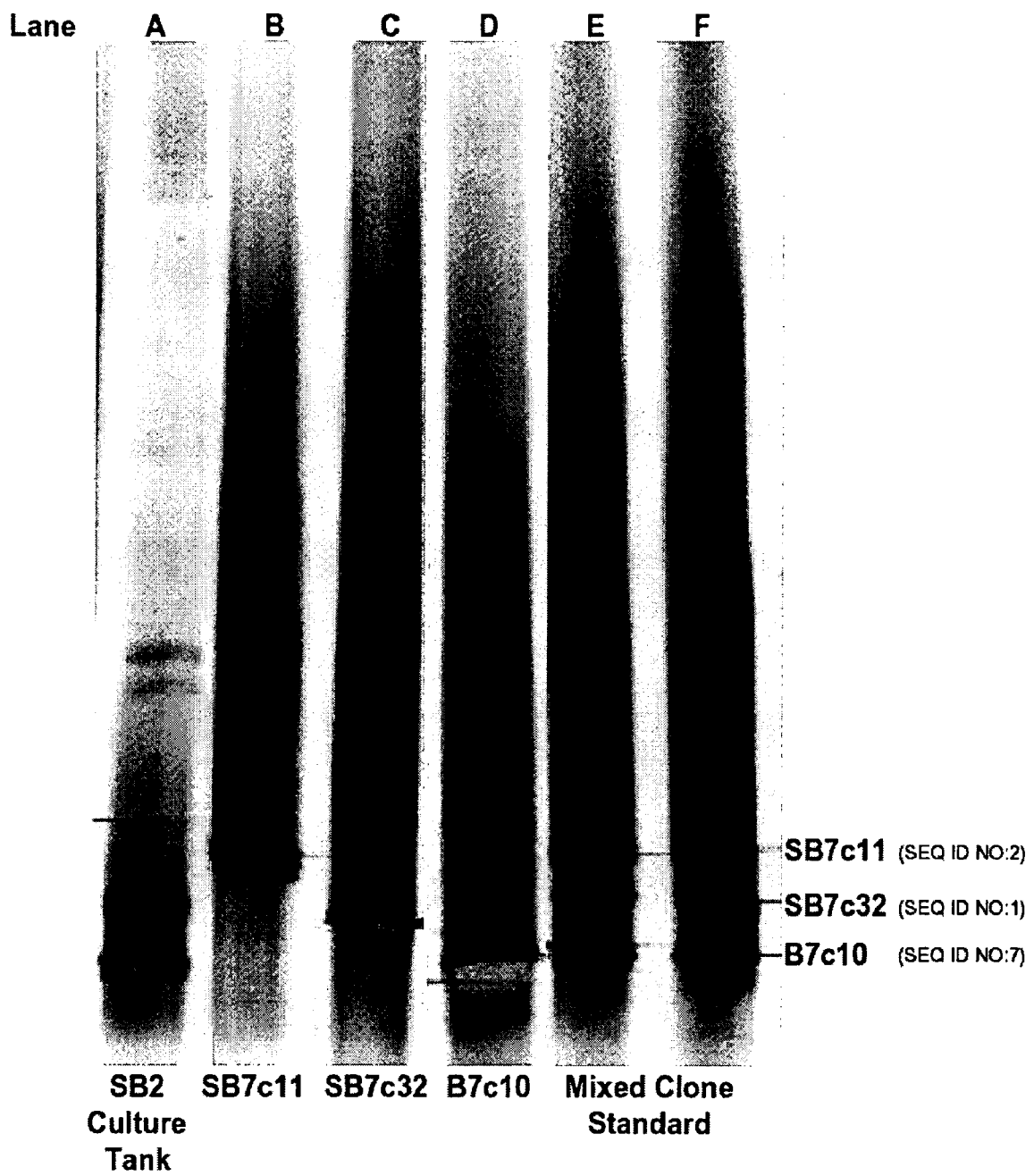
FIG. 3 illustrates a denaturing gradient gel electrophoresis (DGGE) of biomasses from selected enrichments and nitrite-oxidizing bacteria represented by SEQ ID NO:1, SEQ ID NO:2, and SEQ ID NO:7, in accordance with an embodiment of the present invention.

Therefore, a second type of DGGE analysis was set-up. For this DGGE analysis, the gradient was changed from the standard of 25 to 55% to a gradient of 30 to 60% for a run time of 360 minutes at 200 volts. FIG. 3 shows the band migration pattern for a set of mixed clone standards comprised of SEQ ID NO:1, SEQ ID NO:2 (both *Nitrococcus*-like NOB) and SEQ ID NO:7 (*Nitrospira*-like NOB) along with these same clones run individually and an NOB enrichment (Lane A). The results show that we were clearly able to separate the bands of these three clones with this DGGE. In addition, both bands in the enrichment (Lane A) were excised, processed as previously described and sequenced. The upper band aligns to clone SB7c32 (SEQ ID NO:1) and the lower band aligns with clone B7c10 (SEQ ID NO:7) further confirming the validity of our methods and results.

Figure 4:
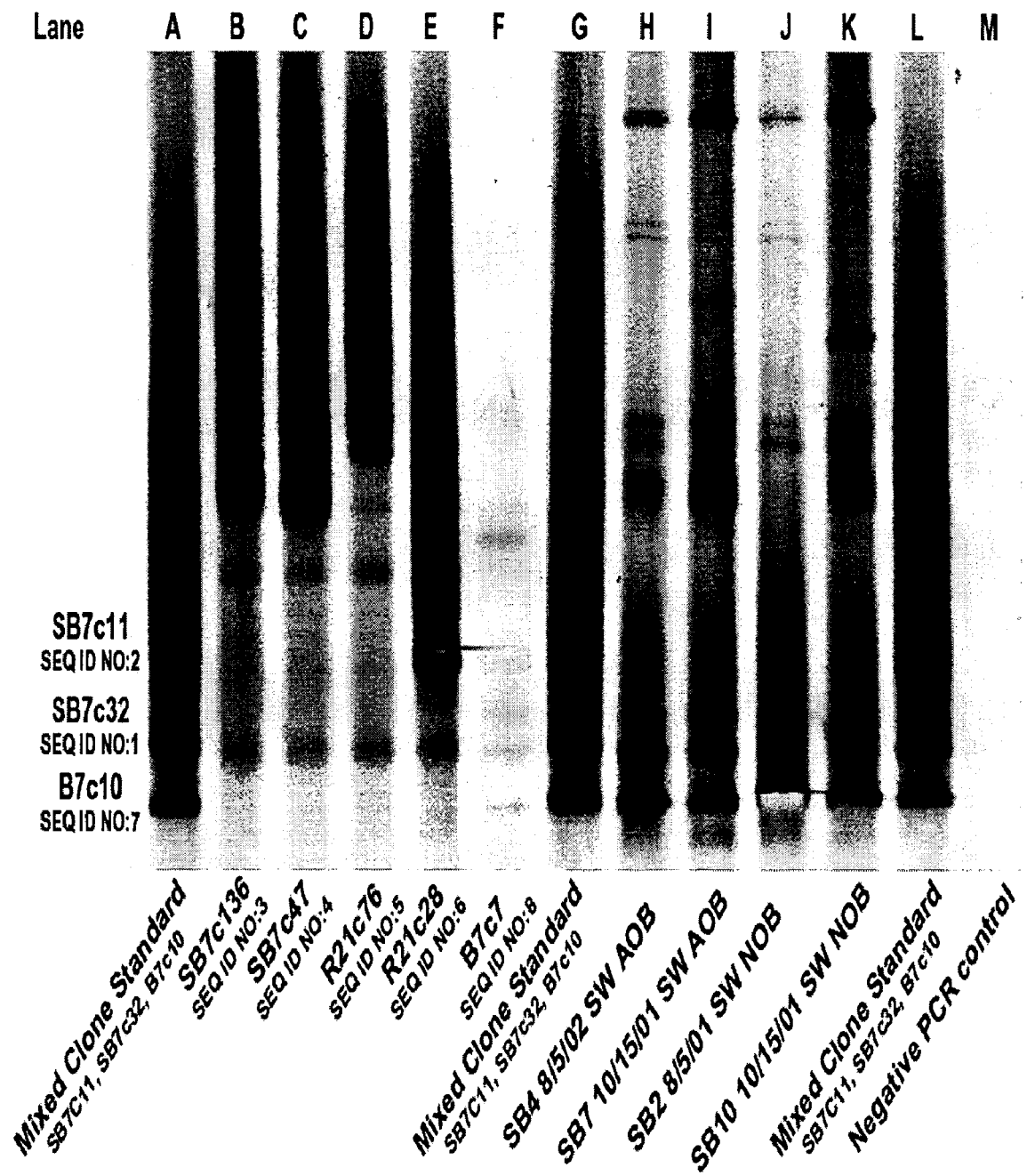
FIG. 4 illustrates a denaturing gradient gel electrophoresis (DGGE) of biomasses from selected enrichments and nitrite-oxidizing bacteria represented by SEQ ID NO:1, SEQ ID NO:2, SEQ ID NO:3, SEQ ID NO:4, SEQ ID NO:5, SEQ ID NO:6, SEQ ID NO:7, and SEQ ID NO:8, in accordance with an embodiment of the present invention.

FIG. 4 represents another DGGE analysis which shows the same enrichment samples as in FIG. 2 but at a greater resolution due to the changed gel conditions (see above). The results clearly show that we are able to distinguish between the *Nitrospira*-like NOB and the *Nitrococcus*-like NOB (Lanes G-K) in environmental samples.

Example 11

Bacterial Additive Tests

A series of experiments were conducted to determine the efficacy of various bacterial mixtures containing the bacterial strains of the present invention as compared to: (1) control aquaria that did not receive a mixture, (2) aquaria that were inoculated with bacterial mixtures for use in tropical fish aquaria, and (3) preserved or stored bacterial mixtures of the bacterial strains of the present invention.

Effectiveness of a mixture is demonstrated by showing that the nitrite-oxidizing bacterial strains of the present invention oxidize nitrite in aquaria and, further, that when combined with other bacterial strains (e.g., ammonia-oxidizing bacteria), the bacteria accelerate the establishment of nitrification in aquaria. Establishment of nitrification can be measured in at least three different ways. The first is by counting the number days it takes after setting-up a new aquarium for the ammonia and nitrite concentrations in the aquarium water to reach a near 0 mg/L concentration. In a newly set-up saltwater aquarium, it typically takes about 14 days for the ammonia concentration to reach 0 mg/L and about 30 to 35 days for nitrite to reach 0 mg/L.

A second way to measure the beneficial action of adding nitrifying bacterial strains to aquaria is to compare the maximum concentration of ammonia or nitrite reached before the concentration drops to 0 mg/L. If the maximum concentration of ammonia or nitrite reached in aquaria in which nitrifying bacteria were added is significantly less than the maximum concentration reached in control aquaria, then a degree of effectiveness is demonstrated.

Example 12

Bacterial Additive Test

The goal of this test was to evaluate the ability of various mixtures of NOB strains of the present invention to oxidize nitrite to nitrate, as they may be implemented in a "real world" setting. The performance of the mixtures of the present invention was compared to commercially available bacterial mixtures that claim they are suitable for use in either freshwater or saltwater aquaria.

For this test, fifteen 10-gallon aquaria and fifteen Penguin 170B (Marineland Aquarium Products) hang-on-the-back style power filters were sterilized, thoroughly rinsed and allowed to air dry. On the following day each tank was filled with 10 lbs. of rinsed Tideline Crushed Coral #5 and equipped with a sterilized power filter (PF 0170B) and rinsed carbon cartridge. Each tank was filled with 35 L of artificial seawater. The seawater was a combination of Tropic Marine salt mix and post GAC water to a salinity of 30 ppt. The filters were allowed to run overnight prior to the addition of bacterial additives and fish.

The next morning the tanks were topped off with ultrapure water to compensate for evaporation and water samples taken. Each tank was dosed with one bacterial treatment, however no bacterial mixture was added to the control group.

There were four treatments for this test: Reactors 21 and 29, which both included all strains of *Nitrospira*-like NOB of the present invention represented by SEQ ID NO:3, SEQ ID NO:4, SEQ ID NO:5, SEQ ID NO:6, SEQ ID NO:7 or SEQ ID NO:8, CYCLE (a commercially available bacterial mixture for use in freshwater or saltwater); and STRESS ZYME (another commercially available bacterial mixture for use in freshwater or saltwater). Each treatment had three replicates. Aquaria receiving the Reactor 21 and Reactor 29 treatments were dosed with 100 ml of either mixture one time on the first day of the test. Aquaria receiving the CYCLE or STRESS ZYME treatments were dosed with 10 ml of either treatment on the first day of the test, an additional 10 ml on day 7 of the test and an additional 5 ml every 7 days after that for the duration of the test. Four assorted damsels (*Pomacentrus* spp.) were added to each tank on the first day of the test and fed twice a day.

Water samples were collected and analyzed daily for pH, ammonia, nitrite and conductivity. On Monday, Wednesday and Friday the water was tested for nitrate and turbidity. Measurements for pH were made with a Denver Instruments Model 225 pH/Ion meter equipped with a Denver Instruments pH combination electrode. A Tecator FIASTAR 5010 Analyzer was used to measure ammonia, nitrite and nitrate (as nitrogen) using methods described in the Tecator Application Notes. Salinity was measured directly in each tank daily using a YSI Model 30 hand-held salinity, conductivity and temperature system. Turbidity data was determined with a DRT-100 turbidity meter (HF Scientific).

Figure 5:
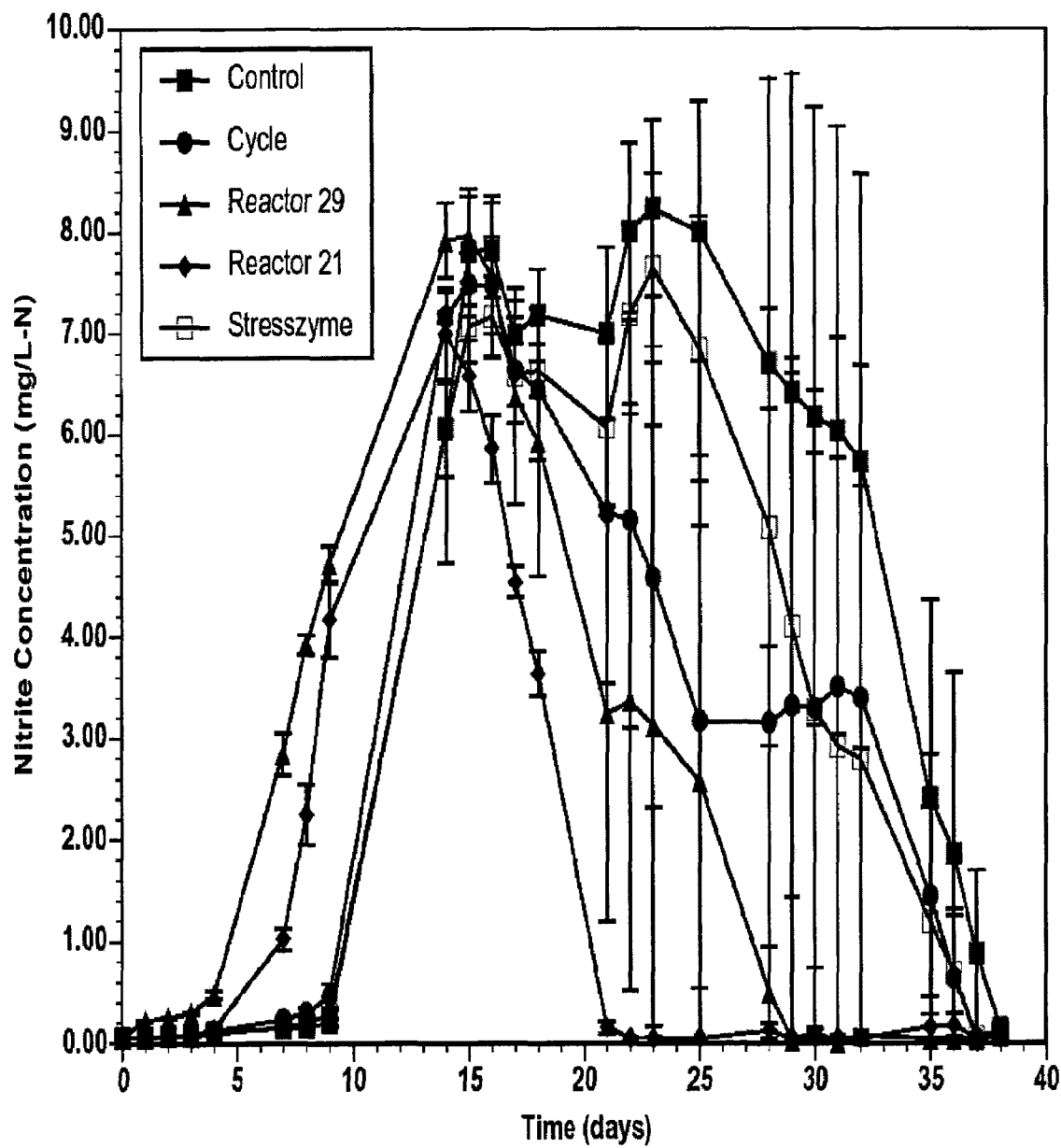
FIG. 5 illustrates mean nitrite concentration trends for a Bacterial Additives Test for saltwater bacterial strains and two commercial additives.

The mean nitrite concentrations for the four treatments and control are depicted in FIG. 5. Treatment Reactors 21 and 29, which comprised strains of NOB represented by SEQ ID NO:3, SEQ ID NO:4, SEQ ID NO:5, SEQ ID NO:6, SEQ ID NO:7 and SEQ ID NO:8 oxidized nitrite much more quickly than the other treatments. The nitrite concentration in the Reactor treatments peaked and fell back to 0 mg/L much sooner than in the case of the other treatments (FIG. 5). Reactor 21 reached 0 mg/L on day 21, Reactor 29 reached 0 mg/L on day 29 while the control and commercial additives did not fall back to 0 mg/L until day 37 or later (FIG. 5).

These results demonstrate that (1) the strains of NOB of the present invention accelerate nitrite oxidation in newly set-up saltwater aquaria and (2) the commercial additives which reportedly contain the NOB *Nitrobacter winogradskyi* are not effective at controlling nitrite during the start-up of new seawater aquaria.

Example 13

Bacterial Additive Test

The goal of this test was to evaluate the ability of various mixtures of NOB strains of the present invention to oxidize nitrite to nitrate, as they may be implemented in a "real world" setting. Material from reactor SB7 (which contained both *Nitrospira*-like NOB and *Nitrococcus*-like NOB strains of the present invention) was placed in aquaria and the performance of this system was compared to aquaria that did not receive a bacterial inoculation.

For this test, eight 10-gallon aquaria and eight Penguin 170B (Marineland Aquarium Products) hang-on-the-back style power filters were sterilized, thoroughly rinsed and allowed to air dry. On the following day each tank was filled with 10 lbs. of rinsed Tideline Crushed Coral #5 and equipped with a sterilized power filter (PF 0170B) and rinsed carbon cartridge. Each tank was filled with 35 L of artificial seawater. Artificial seawater was made by adding INSTANT OCEAN SeaSalts (Aquarium Systems, Mentor, Ohio) to carbon filtered city water until the salinity was 30 ppt. The aquaria were filled with the seawater and the filters were allowed to run overnight prior to the addition of bacterial additives and fish.

The next morning the tanks were topped off with ultrapure water to compensate for evaporation and water samples taken. Then four tanks were dosed with 150 ml of SB7 reactor bacterial mixture. The other four tanks were not dosed with a bacterial mixture. The SB7 reactor mixture consisted of strains of *Nitrococcus*-like NOB and *Nitrospira*-like NOB of the present invention, represented by SEQ ID NO:1, SEQ ID NO:2, SEQ ID NO:3, SEQ ID NO:4, SEQ ID NO:5, SEQ ID NO:6, SEQ ID NO:7 and SEQ ID NO:8. Six clownfish (*Amphiprion ocellaris*) were added to each tank on the first day of the test and fed twice a day. The fish feed was a mixture of frozen brine shrimp and *Spirulina* fish flakes. On Day 3 of the test, four additional clownfish (*Amphiprion ocellaris*) were added to each aquarium.

Water samples were collected and tested daily for pH, ammonia, nitrite and conductivity. On Monday, Wednesday and Friday the water was tested for nitrate and turbidity. Measurements for pH were made with a Denver Instruments Model 225 pH/Ion meter equipped with a Denver Instruments pH combination electrode. A Tecator FIASTAR 5010 Analyzer was used to measure ammonia, nitrite and nitrate (as nitrogen) using methods described in Tecator Application Notes. Salinity was measured directly in each tank daily using a YSI Model 30 hand-held salinity, conductivity and temperature system. Turbidity data was determined with a DRT-100 turbidity meter (HF Scientific).

Figure 6:
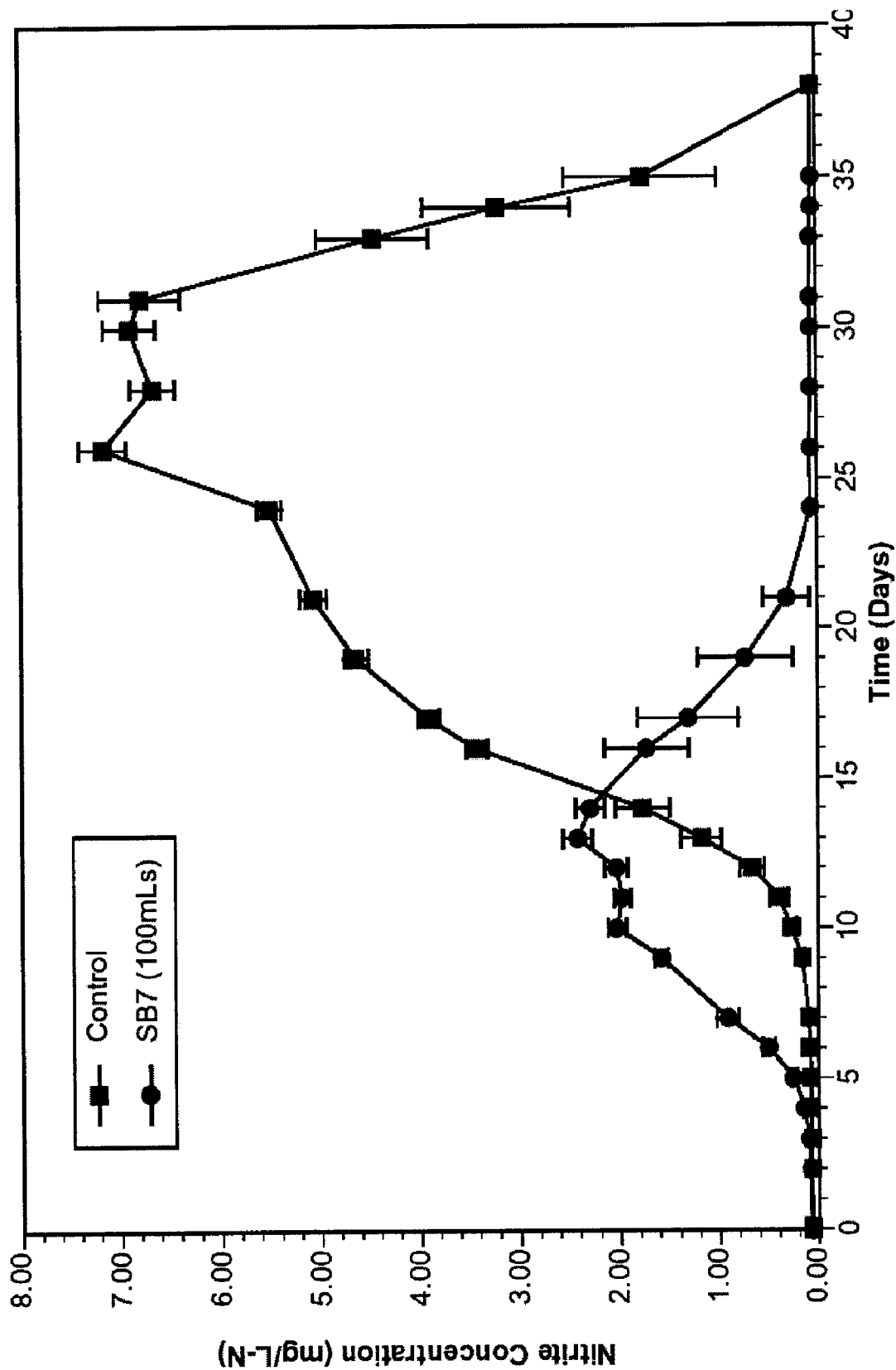
FIG. 6 illustrates mean nitrite concentration trends for a Bacterial Additives Test for saltwater bacterial strains against an non-inoculated control.

The mean nitrite concentrations for the SB7 treatment and control are presented in FIG. 6. The SB7 treatment oxidized nitrite significantly faster than did the control. The mean nitrite concentration reached 0 mg/L on day 24 in tanks receiving the SB7 treatment, while 38 days elapsed in the control aquaria before nitrite values reached the same level of 0 mg/L. Furthermore, the mean maximum nitrite concentration of the SB7 treatment (about 2.4 mg/L-N) was significantly lower than the mean maximum nitrite concentration of the control treatment (7.2 mg/L-N) (FIG. 6).

The results demonstrate that the strains of NOB of the present invention are effective at accelerating nitrite oxidation in newly set-up seawater aquaria and maintaining nitrite below toxic concentrations during this time period.

Example 14

Bacterial Additive Test

The goal of this test was to assess the viability of freeze-dried saltwater nitrite-oxidizing bacteria that had been stored for 5.5 months. The goal of this test was also to test the effectiveness of various compositions, as described herein, for maintaining aqueous media.

Methods: Preparation of Bacteria

600 L of NOB from Reactor SB1 and 600 L of NOB from Reactor SB2 were mixed together and settled in a Harvest Only Tank (HOT) overnight. Both Reactor SB1 and Reactor SB2 contained all of the strains of NOB of the present invention (represented by SEQ ID NO:1, SEQ ID NO:2, SEQ ID NO:3, SEQ ID NO:4, SEQ ID NO:5, SEQ ID NO:6, SEQ ID NO:7 and SEQ ID NO:8) and both were maintained at a salinity of 30 ppt. The following day, as much supernatant as possible was removed from the tank. A second concentration was carried out in smaller containers until as much supernatant as possible was removed. The remaining bacteria were collected and placed in a 5 L container to settle for 4-5 more hours. Again, as much supernatant as possible was removed and the solution was split to two parts. At this point, trehalose was added to the bacterial solutions as a cryoprotectant in varying amounts. In one solution, 50 g of trehalose was mixed with 1,000 mL of NOB for a 5% trehalose solution and in the other solution, 100 g of trehalose was mixed with 1,000 mL of NOB for a 10% trehalose solution (Table 14). AOB from two saltwater reactors were similarly prepared for freeze-drying. Samples were stored at 4° C. prior to further processing. Excess amounts of NOB and AOB, with no cryopreservative, were stored at 4° C. to be used as positive controls.

TABLE 14

Experimental set-up of bacteria for freeze-drying

| Bacteria type | SB1 and SB2 NOB | AOB |
|---|---|---|
| Salinity | 30 ppt | 30 ppt |
| cryoprotectant | 5%, 10% Trehalose | 5%, 10% Trehalose |
| process | Dry | Dry |
| Freeze rate | −40° C. for dry | −40° C. for dry |
| Primary Sublimation Rate | mild, aggressive | mild, aggressive |

For freeze-drying, the samples were split in order to test two primary sublimation rates (PSR): mild and aggressive. All samples were poured onto pre-refrigerated trays and placed in a freezer. The freezer was cooled to −40° C. Samples were frozen for 3 hours and subsequently placed in a drier. The samples were dried at either the mild or aggressive PSR. The freeze-dried samples were stored in lyophilized form for 5.5 months at 4° C.

Test set-up: Twenty-eight five-gallon aquaria and filters were disinfected with Sanaqua, rinsed, and allowed to air-dry. Aquaria were filled with 19 liters of freshly prepared artificial seawater, made by dissolving INSTANT OCEAN Sea Salts in post-GAC to a salinity of 29 ppt.

A Penguin 125 power filter, equipped with a freshly rinsed, carbon cartridge, and a new BIOWHEEL was placed on each aquarium, plugged in, and allowed to run over-night. Using the Access Test Database, aquaria were randomly assigned a particular treatment consisting of four replicates each (Table 15).

TABLE 15

Bacterial Additive Test 48 Set-Up

| Sample Numbers | Cryopreservative | Primary Sublimation Rate | | Amount of material per tank | Estimate of liquid equivalent |
|---|---|---|---|---|---|
| 7, 15, 20, 24 | 5% Trehalose | Fast | 1x | 0.4 g AOB + 0.2 g NOB | 2 mL AOB + 1 mL NOB |
| 4, 6, 13, 21 | 5% Trehalose | Fast | 5x | 2 g AOB + 1.0 g NOB | 10 mL AOB + 5 mL NOB |
| 1, 9, 10, 22 | 10% Trehalose | Slow | 1x | 0.5 g AOB + 0.25 g NOB | 2 mL AOB + 1 mL NOB |
| 3, 8, 19, 23 | 10% Trehalose | Fast | 1x | 0.5 g AOB + 0.25 g NOB | 2 mL AOB + 1 mL NOB |

TABLE 15-continued

Bacterial Additive Test 48 Set-Up

| Sample Numbers | Cryopreservative | Primary Sublimation Rate | Amount of material per tank | | Estimate of liquid equivalent |
|---|---|---|---|---|---|
| 5, 17, 18, 27 | 4° C. | | 1x | 1 mL AOB + 0.5 mL NOB | |
| 2, 16, 25, 26 | Positive | | 1x | 1 mL AOB + 0.5 mL NOB | |
| 11, 12, 14, 28 | Negative | | | | |

At the start of the test, the aquaria were topped off with deionized water, to make up for water lost to evaporation, and a baseline sample was taken. The bacteria were added at 11 a.m. and left to circulate for 30 minutes before taking the second baseline samples. At 12:30 p.m., 9 domino damsels were added to each aquarium. Every morning the aquaria were topped off with deionized water and then sampled.

The samples were analyzed daily for pH, ammonia, nitrite, and turbidity. Nitrate was measured intermittently throughout the test. Ammonia and nitrite were measured on a Foss FIA-STAR 5000 using methods described in the Foss Application Notes. A Tecator FIASTAR 5010 was used to measure nitrate (as nitrogen) using methods described in the Tecator Application Notes. Turbidity data was determined using the HF Scientific Micro 100 Turbidimeter.

Results: Table 16 reports the initial wet weight of the freeze-dried bacteria and trehalose mixture for each treatment that was freeze-dried and the dry weight yield, post lyophilization.

TABLE 16

Initial wet weights and dry weight yields of the various freeze-dried bacteria treatments

| Bacteria | % Cryo | PSR | Initial Volume (L) | Wet wt (g) | Dry wt (g) |
|---|---|---|---|---|---|
| AOB | 5% | Mild | 1000 | 1047.2 | 200.5 |
| AOB | 5% | Aggressive | 1000 | 1046.6 | 201.2 |
| AOB | 10% | Mild | 1000 | 1082.4 | 248.4 |
| AOB | 10% | Aggressive | 1000 | 1082.2 | 249.1 |
| NOB | 5% | Mild | 500 | 539.7 | 102.4 |
| NOB | 5% | Aggressive | 500 | 537.8 | 103.7 |
| NOB | 10% | Mild | 500 | 549.0 | 122.0 |
| NOB | 10% | Aggressive | 500 | 548.2 | 121.7 |

During the freeze-drying process the following was noted: the mild PSR took about 35 hours, finishing at a temperature of 27° C. The aggressive PSR took about 28 hours, finishing at a temperature of 27° C. The NOB dried faster than the AOB. The 10% trehalose solutions left a thin sugar layer on the dried product. No internal boiling was noted.

Figure 7:
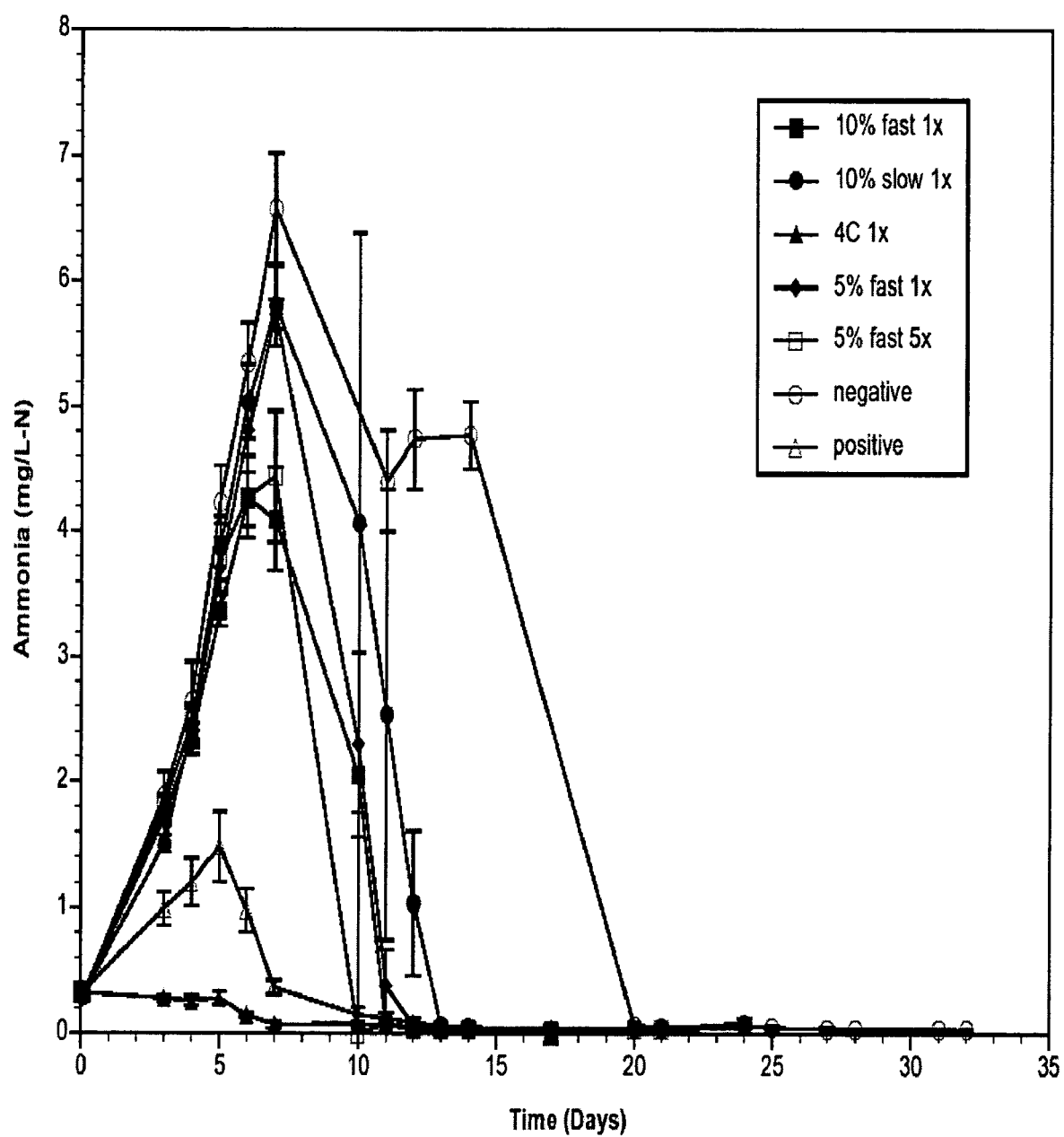
FIG. 7 illustrates mean ammonia concentration trends for a Bacterial Additives Test for assessing the viability of freeze-dried saltwater bacterial strains that had been stored for 5.5 months.

FIG. 7 shows the mean ammonia values (N=4) for the various treatments in this test. The negative control (no addition of bacteria) took 20 days to reach a 0 mg/L concentration of ammonia. The ammonia in this treatment peaked on day 7 at a value of nearly 7 mg/L. In contrast to these values, all the treatments, whether they received a liquid (positive control) or freeze-dried form of the nitrifying bacteria, reach a 0 mg/L concentration of ammonia significantly faster (FIG. 7).

The mean ammonia concentration values for the freeze-dried treatments fell between those of the positive and negative controls (FIG. 7). In general, the aquaria receiving the freeze-dried treatments reached a maximum ammonia concentration of about 4-6 mg/L and reached 0 mg/L between days 10 and 13.

Figure 8:
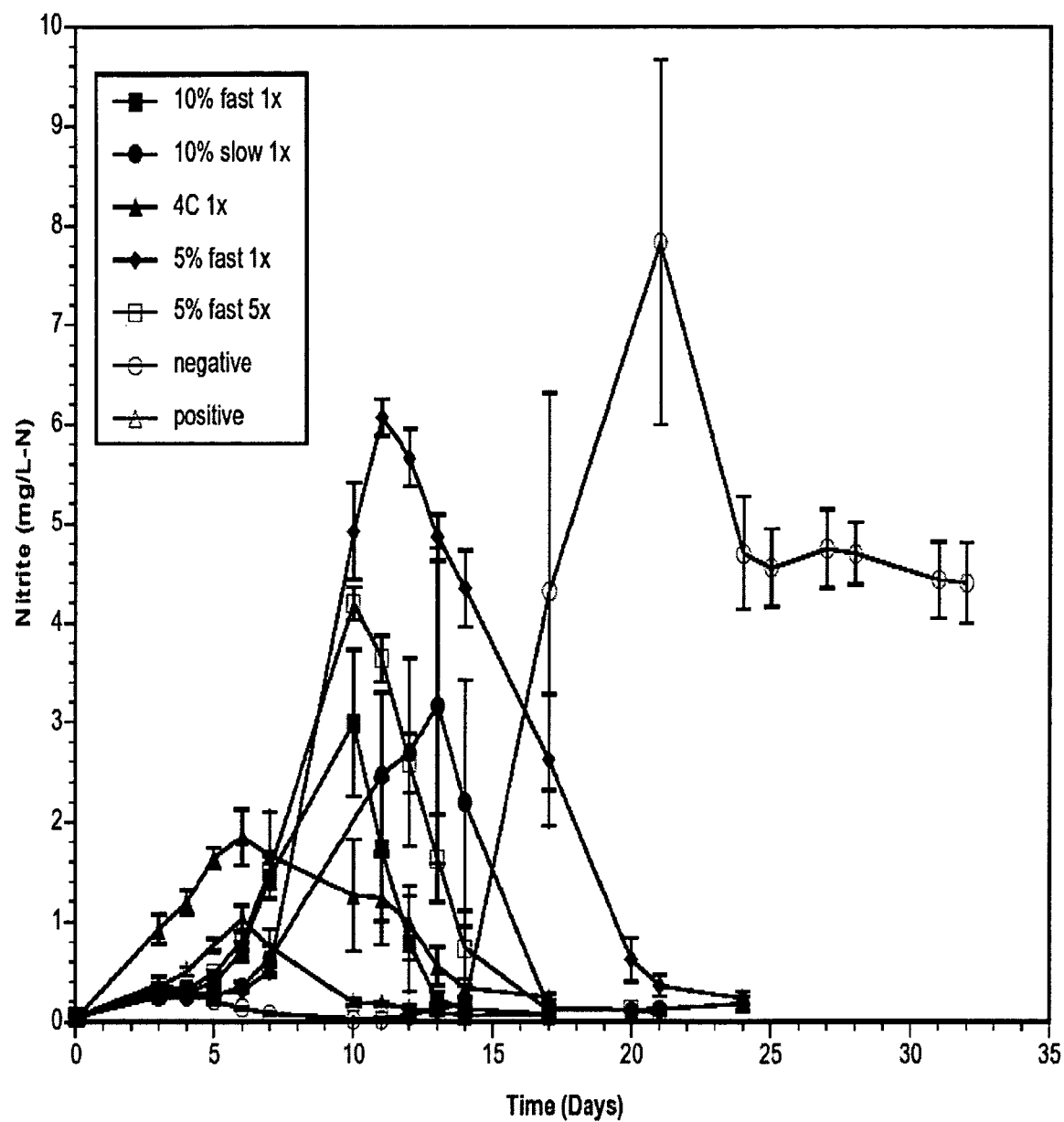
FIG. 8 illustrates mean nitrite concentration trends for a Bacterial Additives Test for assessing the viability of freeze-dried saltwater bacterial strains that had been stored for 5.5 months.

The mean nitrite concentrations for the various treatments of this test are presented in FIG. 8. These results mirror those for the ammonia data. All the aquaria which received a bacterial inoculation, whether the positive control or freeze-dried, exhibited nitrification significantly faster than those aquaria that received the negative (FIG. 8).

Figure 9:
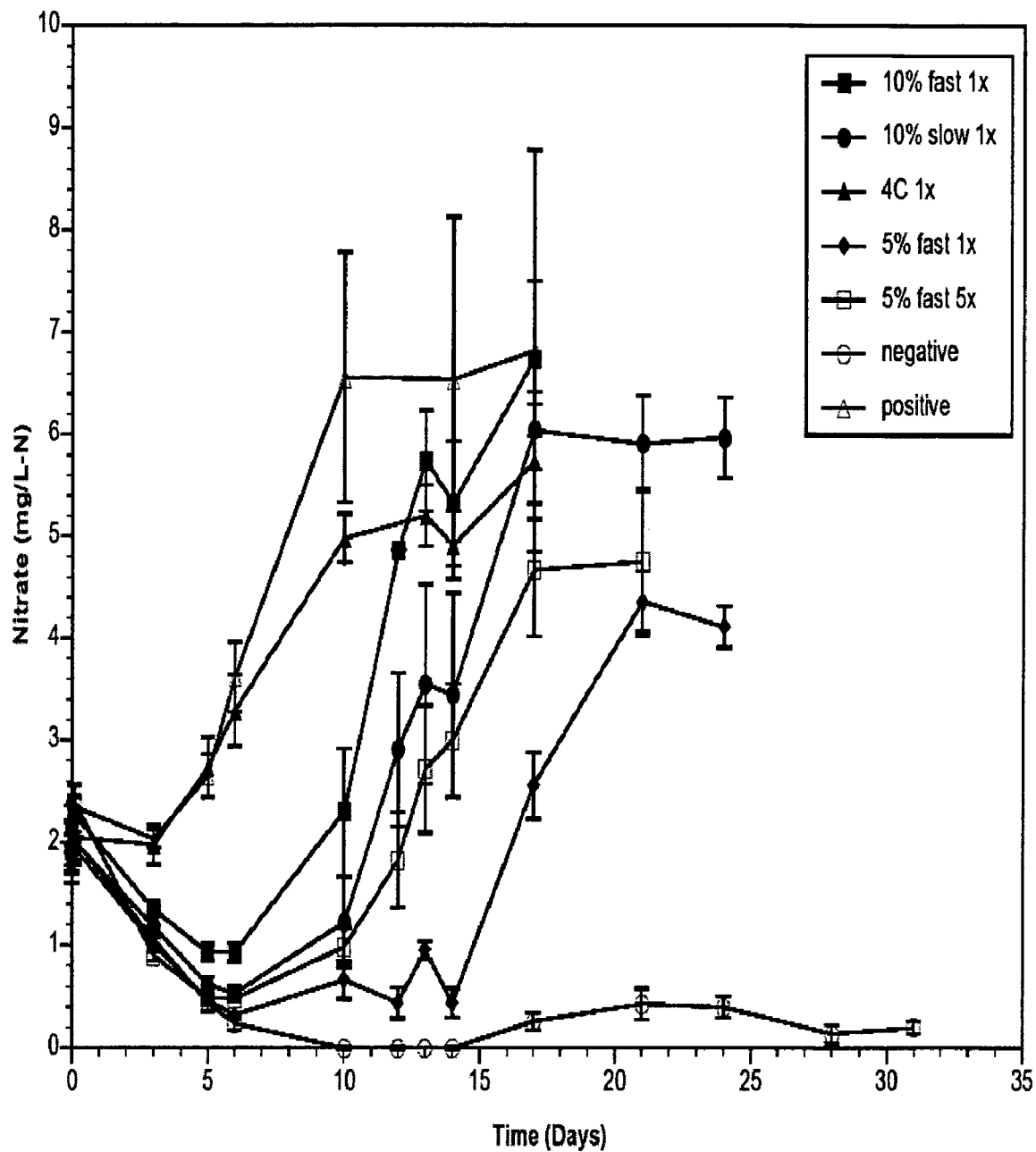
FIG. 9 illustrates mean nitrate concentration trends for a Bacterial Additives Test for assessing the viability of freeze-dried saltwater bacterial strains that had been stored for 5.5 months.

FIG. 9 confirms that the disappearance of ammonia and nitrite were due to oxidation of those compounds to nitrate. The figure clearly shows that all treatments produced an increase in nitrate concentration over time. The positive control treatment started to produce nitrate almost immediately after the test began. The freeze-dried treatments started generating nitrate by about day 10-15. This confirms that nitrification was established more quickly in aquaria inoculated with the bacterial strains of the present invention than in non-inoculated aquaria.

The results of this test demonstrate that freeze-dried preparations of the bacterial strains of the present invention maintain their viability and their ability to oxidize nitrite to nitrate after extensive storage in freeze-dried form. The results of this test also demonstrate that liquid and freeze-dried preparations of the bacterial strains of the present invention can establish nitrification in newly set-up aquaria much faster than non-inoculated aquaria. The results of this test also demonstrate that compositions for the maintenance of aqueous media, as described herein, are capable of oxidizing ammonia to nitrite and nitrate to nitrate in said aqueous media.

Example 15

Bacterial Additive Test

The goal of this test was to assess the viability of freeze-dried saltwater nitrite-oxidizing bacteria that had been stored for 11 months and to determine the optimal dose of saltwater nitrite oxidizing bacteria for the purpose of reducing the concentration of nitrite in a aqueous medium. The goal of this test was also to test the effectiveness of various compositions, as described herein, for maintaining aqueous media.

Methods: Preparation of Bacteria

600 L of NOB from Reactor SB1 and 600 L of NOB from Reactor SB2 were mixed together and settled in a Harvest Only Tank (HOT) overnight. Both Reactor SB1 and Reactor SB2 contained all of the strains of NOB of the present invention (represented by SEQ ID NO:1, SEQ ID NO:2, SEQ ID NO:3, SEQ ID NO:4, SEQ ID NO:5, SEQ ID NO:6, SEQ ID NO:7 and SEQ ID NO:8) and both were maintained at a salinity of 30 ppt. The following day, as much supernatant as possible was removed from the tank. A second concentration was carried out in smaller containers until as much supernatant as possible was removed. The remaining bacteria were collected and placed in a 5 L container to settle for 4-5 more hours. Again, as much supernatant as possible was removed and the solution was split to two parts. At this point, trehalose was added to the bacterial solutions as a cryoprotectant in varying amounts. In one solution, 50 g of trehalose was mixed with 1,000 mL of NOB for a 5% trehalose solution and in the other solution, 100 g of trehalose was mixed with 1,000 mL of NOB for a 10% trehalose solution (Table 17). AOB from two saltwater reactors were similarly prepared for freeze-drying. Samples were stored at 4° C. prior to further processing. Excess amounts of NOB and AOB, with no cryopreservative, were stored at 4° C. to be used as positive controls.

TABLE 17

Experimental set-up of bacteria for freeze-drying

| Bacteria type | SB1 and SB2 NOB | AOB |
|---|---|---|
| Salinity | 30 ppt | 30 ppt |
| cryoprotectant | 5%, 10% Trehalose | 5%, 10% Trehalose |
| process | Dry | Dry |
| Freeze rate | −40° C. for dry | −40° C. for dry |
| Primary Sublimation Rate | mild, aggressive | mild, aggressive |

For freeze-drying, the samples were split in order to test two primary sublimation rates (PSR): mild and aggressive. All samples were poured onto pre-refrigerated trays and placed in a freezer. The freezer was cooled to −40° C. Samples were frozen for 3 hours and subsequently placed in a drier. The samples were dried at either the mild or aggressive PSR. The freeze-dried samples were stored in lyophilized form for 11 months at 4° C.

2 L of fresh cells for comparative testing was taken from both saltwater NOB reactors (SB 1 and SB2) and 5 L of fresh cells were taken from the two saltwater AOB reactors. The NOB were combined separately and left to settle overnight. The next day the supernatant was drawn off and the remaining samples were placed in an Imhoff settling cone to determine the density. Based on the density, a dilution was made to reach the high dose concentration (Table 18) with freshly made saltwater mixed with INSTANT OCEAN Sea Salts and deionized water to a salinity of 28 ppt. Serial dilutions of this stock were made with saltwater to obtain the medium and low dosage used in this test (Table 18).

Test set-up: Thirty-two ten-gallon aquaria and filters were disinfected with Sanaqua, rinsed, and allowed to air-dry. Aquaria were filled with 37 liters of freshly prepared artificial seawater, made by dissolving INSTANT OCEAN Sea Salt in post-GAC to a salinity of 29 ppt. A Penguin 125 power filter, equipped with a freshly rinsed, carbon cartridge, and a new BIOWHEEL was placed on each aquarium, plugged in, and allowed to run over-night. Using the Access Test Database, aquaria were randomly assigned a particular treatment consisting of four replicates each (Table 18).

TABLE 18

Bacterial Additive Test 54 Set-Up

| Sample Numbers | Cryopreservative | Primary Sublimation Rate | | Amount of material per tank | Estimate of liquid equivalent |
|---|---|---|---|---|---|
| 4, 27, 29, 30 | 5% Trehalose | Fast | 1x | 0.4 g AOB + 0.2 g NOB | 2 mL AOB + 1 mL NOB |
| 12, 19, 28, 31 | 5% Trehalose | Fast | 5x | 2 g AOB + 1.0 g NOB | 10 mL AOB + 5 mL NOB |
| 14, 15, 17, 22 | 10% Trehalose | Fast | 1x | 0.5 g AOB + 0.25 g NOB | 2 mL AOB + 1 mL NOB |
| 6, 7, 18, 23 | 4° C. | — | 1x | 1 mL AOB + 0.5 mL NOB | — |

| | Fresh Cells | Amount of cells per tank | | [AOB] and dose | [NOB] and dose |
|---|---|---|---|---|---|
| 1, 3, 20, 32 | High Dose | 1 mL AOB + 0.5 mL NOB | 4x | 5 mL/L 200 mL/tank | 2.5 mL/L 200 mL/tank |
| 5, 8, 9, 21 | Middle Dose | 0.5 mL AOB + 0.25 mL NOB | 2x | 2.5 mL/L 200 mL/tank | 1.25 mL/L 200 mL/tank |
| 2, 10, 25, 26 | Low Dose | 0.25 mL AOB + 0.125 mL NOB | 1x | 1.25 mL/L 200 mL/tank | 0.625 mL/L 200 mL/tank |
| 11, 13, 16, 24 | Negative | — | — | 0 | 0 |

At the start of the test, the aquaria were topped off with deionized water, to make up for water lost to evaporation, and a baseline sample was taken. The bacteria were added at 10 a.m. and left to circulate for 30 minutes before taking the second baseline samples. Every morning the aquaria were topped off with deionized water and then sampled. Ammonia (0.5 mg/L) was added manually to the aquaria each day, post sampling, to simulate fish excretion.

The samples were analyzed daily for pH, ammonia, nitrite, and turbidity. Nitrate was measured intermittently throughout the test. Ammonia and nitrite were measured on a Foss FIA-STAR 5000 using methods described in the Foss Application Notes. A Tecator FIASTAR 5010 was used to measure nitrate (as nitrogen) using methods described in the Tecator Application Notes. Turbidity data was determined using the HF Scientific Micro 100 Turbidimeter.

Results: Table 19 reports the initial wet weight of the freeze-dried bacteria and trehalose mixture for each treatment that was freeze-dried and the dry weight yield, post lyophilization.

TABLE 19

Initial wet weights and dry weight yields of the various freeze-dried bacteria treatments

| Bacteria | % Cryo | PSR | Initial Volume (L) | Wet wt (g) | Dry wt (g) |
|---|---|---|---|---|---|
| AOB | 5% | Mild | 1000 | 1047.2 | 200.5 |
| AOB | 5% | Aggressive | 1000 | 1046.6 | 201.2 |
| AOB | 10% | Mild | 1000 | 1082.4 | 248.4 |
| AOB | 10% | Aggressive | 1000 | 1082.2 | 249.1 |
| NOB | 5% | Mild | 500 | 539.7 | 102.4 |
| NOB | 5% | Aggressive | 500 | 537.8 | 103.7 |
| NOB | 10% | Mild | 500 | 549.0 | 122.0 |
| NOB | 10% | Aggressive | 500 | 548.2 | 121.7 |

During the freeze-drying process the following was noted: the mild PSR took about 35 hours, finishing at a temperature of 27° C. The aggressive PSR took about 28 hours, finishing at a temperature of 27° C. The NOB dried faster than the AOB. The 10% trehalose solutions left a thin sugar layer on the dried product. No internal boiling was noted.

Figure 10:
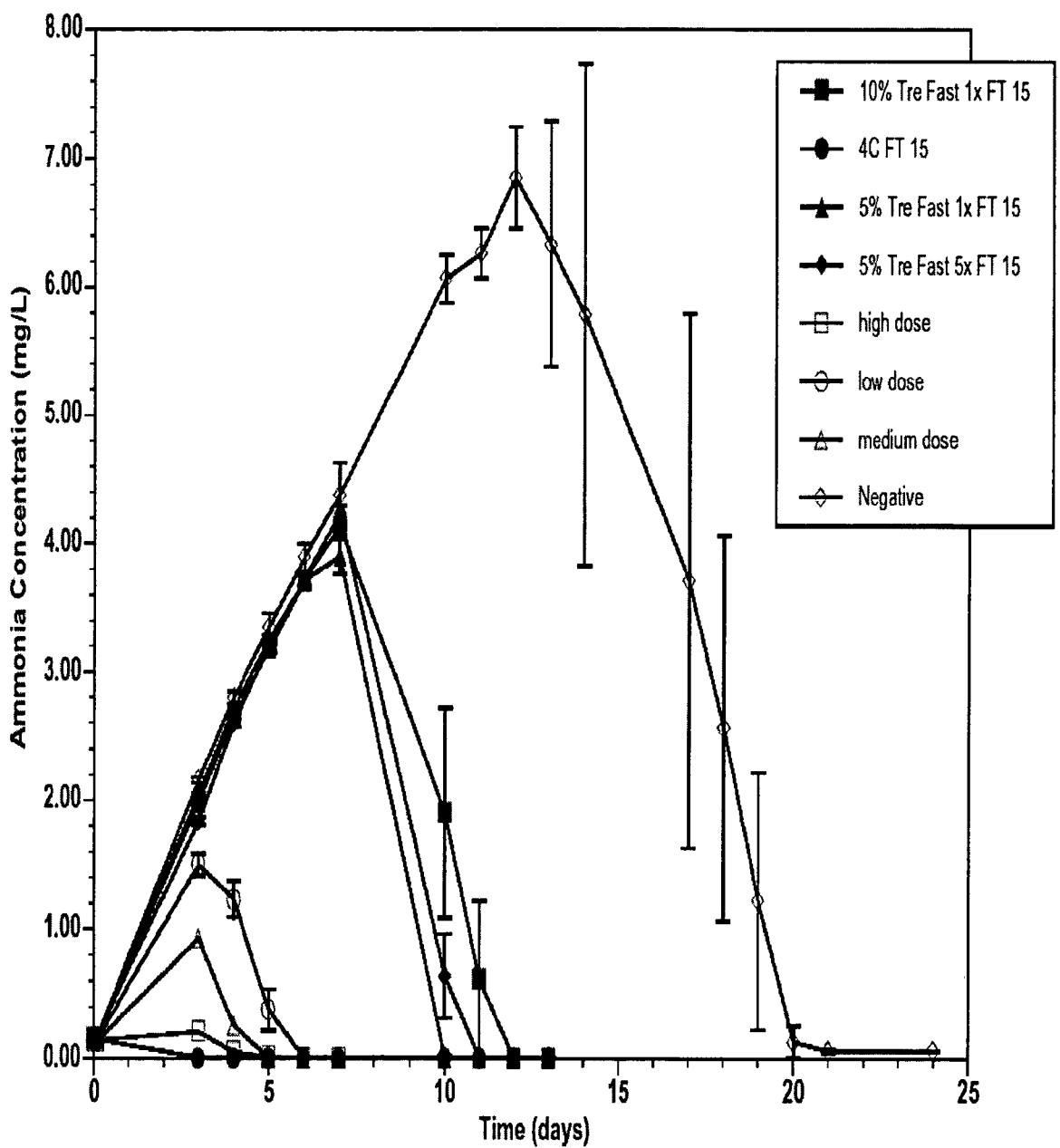
FIG. 10 illustrates mean ammonia concentration trends for a Bacterial Additives Test for assessing the viability of freeze-dried saltwater bacterial strains that had been stored for 11 months.

FIG. 10 shows the mean ammonia values (N=4) for the various treatments in this test. The control (no addition of bacteria) took 20 days to reach a 0 mg/L concentration of ammonia. The ammonia in this treatment peaked on day 12 at a value of nearly 7 mg/L. In contrast to these values, all the treatments, whether they received a liquid or freeze-dried form of the nitrifying bacteria, reach a 0 mg/L concentration of ammonia significantly faster (FIG. 10).

For the liquid from there was a clear trend of a higher dosage establishing nitrification faster. The mean ammonia value in the high dose treatment did not exceed 0.3 mg/L and the aquaria reached 0 mg/L NH3-N by day 4. For the medium dosage treatment, the mean ammonia concentration reached a maximum value of about 1 mg/L and reached 0 mg/L by day 5 (FIG. 10). For the low dose treatment, the mean ammonia concentration reached a maximum value of 1.5 mg/L and reached 0 mg/mL by day 6.

The mean ammonia concentration values for the freeze-dried treatments were very close to each other and fell between those of the liquid treatments and the controls (FIG. 10). In general, the aquaria receiving the freeze-dried treatments reached a maximum ammonia concentration of about 4 mg/L and reached 0 mg/L between days 10 and 12.

Figure 11:
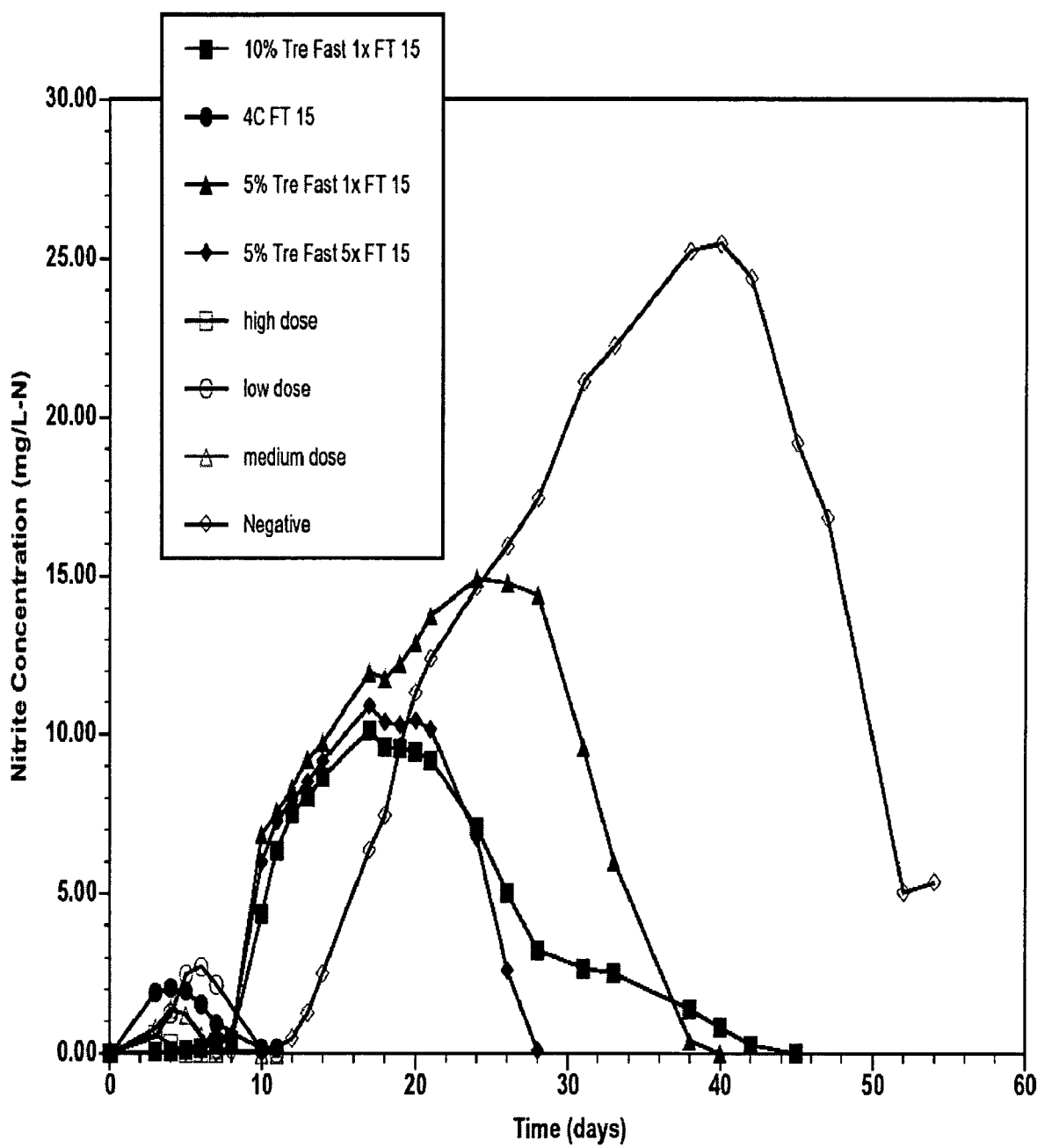
FIG. 11 illustrates mean nitrite concentration trends for a Bacterial Additives Test for assessing the viability of freeze-dried saltwater bacterial strains that had been stored for 11 months.

The mean nitrite concentrations for the various treatments of this test are presented in FIG. 11. These results mirror those for the ammonia data. The non-inoculated aquaria took, on average, over 50 days to reach 0 mg/L NO2-N after reaching a maximum concentration of nearly 26 mg/L NO2-N. All the aquaria which received a bacterial inoculation, whether liquid or freeze-dried, exhibited nitrification significantly faster than those aquaria that received no inoculation (FIG. 11).

Figure 12:
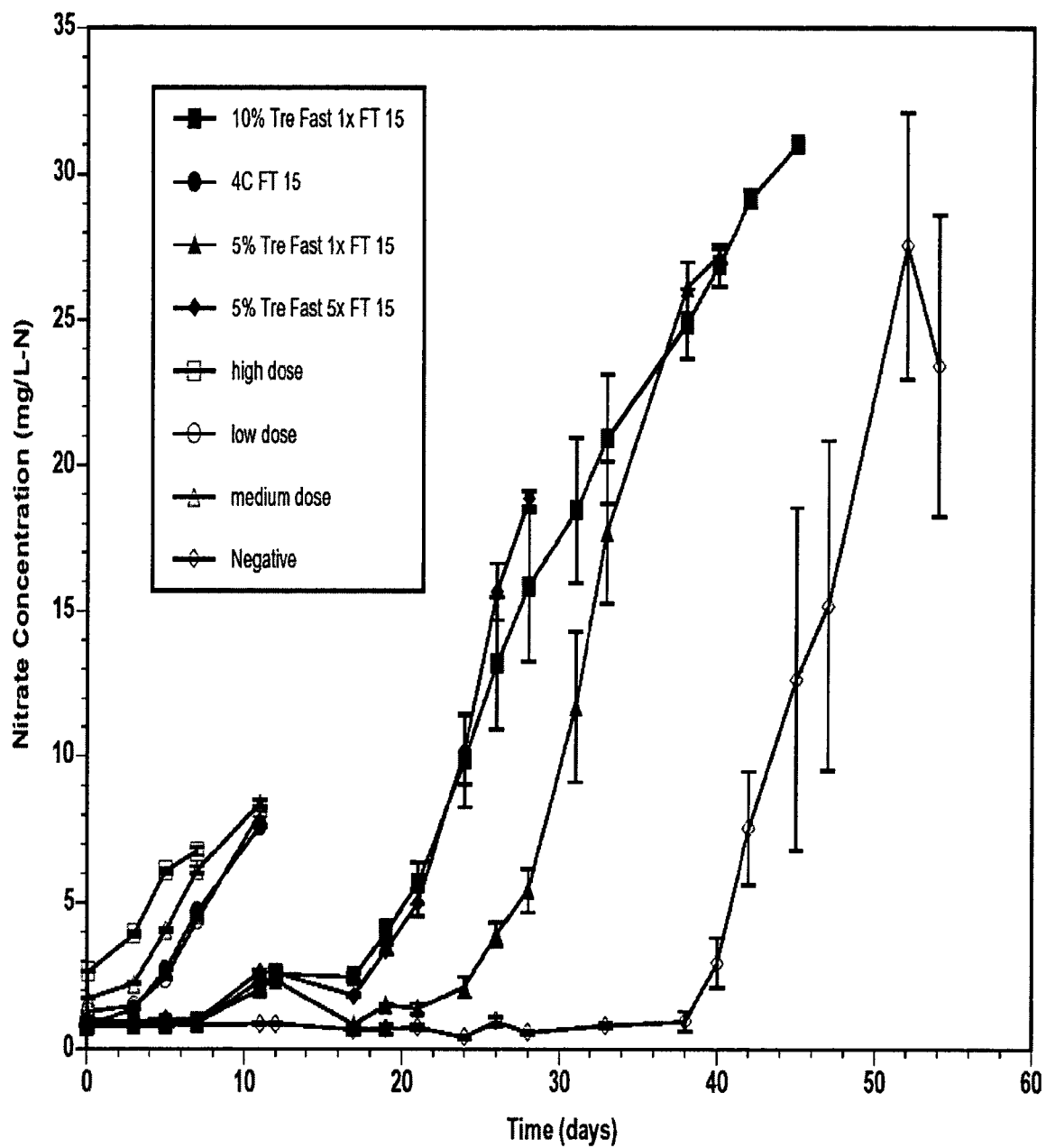
FIG. 12 illustrates mean nitrate concentration trends for a Bacterial Additives Test for assessing the viability of freeze-dried saltwater bacterial strains that had been stored for 11 months.

FIG. 12 confirms that the disappearance of ammonia and nitrite were due to oxidation of those compounds to nitrate. The figure clearly shows that all treatments produced an increase in nitrate concentration over time. The liquid treatments started to produce nitrate almost immediately after the test began. The freeze-dried treatments started generating nitrate by about day 17 while the non-inoculated aquaria did not start producing nitrate until about day 40. This confirms that nitrification was established more quickly in aquaria inoculated with the bacterial strains of the present invention than in non-inoculated aquaria.

The results of this test demonstrate that freeze-dried preparations of the bacterial strains of the present invention maintain their viability and their ability to oxidize nitrite to nitrate after extensive storage in freeze-dried form. The results of this test also demonstrate that liquid and freeze-dried preparations of the bacterial strains of the present invention can establish nitrification in newly set-up aquaria much faster than non-inoculated aquaria. The results of this test also demonstrate that compositions for the maintenance of aqueous media, as described herein, are capable of oxidizing ammonia to nitrite and nitrate to nitrate in said aqueous media.

Example 16

Bacterial Additive Test

The goal of this test was to assess the viability of frozen saltwater nitrite-oxidizing bacteria that had been stored for 5 months and to assess the viability of bacteria stored in a liquid at different temperatures for 14 months. The goal of this test was also to test the effectiveness of various compositions, as described herein, for maintaining aqueous media.

Methods: Preparation of Bacteria

Saltwater NOB from Reactors SB1 and SB2 were harvested for the present test. Both Reactor SB1 and Reactor SB2 contained all of the strains of NOB of the present invention (represented by SEQ ID NO:1, SEQ ID NO:2, SEQ ID NO:3, SEQ ID NO:4, SEQ ID NO:5, SEQ ID NO:6, SEQ ID NO:7 and SEQ ID NO:8) and both were maintained at a salinity of 30 ppt. AOB from two saltwater reactors were also harvested for the present test. 3 stock solutions of AOB and NOB were made, each incorporating 0%, 5% and 10% trehalose as a cryoprotectant. Samples were then placed at 4° C. for one hour and then at −80° C. for 72 hours. Finally, the samples were divided into thirds and placed at three different storage temperatures: −15° C., −20° C. and −80° C. The samples were stored at these temperatures for 5 months.

Approximately 11 months earlier, saltwater NOB from Reactors SB1 and SB2 and AOB from AOB reactors were stored at 3 different temperatures: 4° C., room temperature and 37° C. These liquid samples were stored for 14 months. At the end of the storage period, each storage condition produced different cell densities. Thus, dilutions were carried out so that each sample contained an equal amount of cells (Table 20). Finally, positive NOB and AOB controls were selected by harvesting bacterial samples from Reactors SB1 and SB2 and from AOB reactors immediately prior to setting up the Bacterial Additives 51 test.

TABLE 20

Preparation of Liquid Samples

| Cell Type | Temperature | Density | Dilution | Yield |
|---|---|---|---|---|
| AOB | 4° C. | 11 ml/L | 450 mL + 50 mL water | 5 ml/L |
| AOB | Room temp | 5 ml/L | 500 mL + 0 mL water | 5 ml/L |
| AOB | 37° | 7.5 ml/L | 666 mL added to NOB | 5 ml/L |
| NOB | 4° C. | 2.5 ml/L | 400 mL + 100 mL water | 1 ml/L |
| NOB | Room temp | 1 ml/L | Use all cells | 1 ml/L |
| NOB | 37° | 3 ml/L | 333 mL added to AOB | 1 Ml/L |

Test set-up: Thirty-six five-gallon aquaria and filters were disinfected with Sanaqua, rinsed, and allowed to air-dry. Aquaria were filled with 19 liters of freshly prepared artificial seawater, made by dissolving INSTANT OCEAN Sea Salt in post-GAC to a salinity of 30 ppt. A Penguin 170 power filter, equipped with a freshly rinsed, carbon cartridge, and a new BIOWHEEL was placed on each aquarium, plugged in, and allowed to run over-night. Using the Access Test Database, aquaria were randomly assigned a particular treatment consisting of four replicates each (Table 21). Treatment conditions for the test were selected from the larger group of bacterial storage conditions (frozen bacteria at −80° C., −20° C. and −15° C. with various concentrations of trehalose and liquid bacteria at 4° C., room temperature and 37° C.) on the basis of initial viability tests performed on the various stored frozen and liquid bacteria.

TABLE 21

Test Set-Up for Bacterial Additive Test

| Treatment | Storage Time | Tank Number | % trehalose | Volume Added AOB/NOB (mL) | Cells Added AOB/NOB(mL) |
|---|---|---|---|---|---|
| FT 17 10° C. | 5 months | 12, 14, 16, 18 | 5% | 2 mL/0.4 mL | 2 mL/0.4 mL |
| FT 17-15° C. | 5 months | 3, 7, 15, 22 | 10% | 2 mL/0.4 mL | 2 mL/0.4 mL |
| FT 17-20° C. | 5 months | 1, 2, 5, 28 | 10% | 2 mL/0.4 mL | 2 mL/0.4 mL |
| FT 17-80° C. | 5 months | 8, 11, 13, 23 | 10% | 2 mL/0.4 mL | 2 mL/0.4 mL |
| Negative | | 4, 9, 10, 32 | | No bacteria | |
| Positive | | 24, 31, 35, 36 | 0% | 25 mL total | 2.5 mL/1.8 mL |
| Liquid Room Temp | 14 months | 17, 20, 21, 25 | 0% | 100 mL/100 mL | 1 mL/0.2 mL |
| Liquid 37° C. | 14 months | 19, 26, 27, 33 | 0% | 100 mL/100 mL | 1 mL/0.2 mL |
| Liquid 4° C. | 14 months | 6, 29, 30, 34 | 0% | 100 mL/100 mL | 1 mL/0.2 mL |

At the start of the test, the aquaria were topped off with deionized water, to make up for water lost to evaporation, and a baseline sample was taken. The bacteria were added and left to circulate for 30 minutes before taking the second baseline samples. Every morning the aquaria were topped off with deionized water and then sampled. Ammonia (0.5 mg/L) was added manually to the aquaria each day, post sampling, to simulate fish excretion.

The samples were analyzed daily for pH, ammonia, nitrite, and turbidity. Nitrate was measured intermittently throughout the test. Ammonia and nitrite were measured on a Foss FIA-STAR 5000 using methods described in the Foss Application Notes. A Tecator FIASTAR 5010 was used to measure nitrate (as nitrogen) using methods described in the Tecator Application Notes. Turbidity data was determined using the HF Scientific Micro 100 Turbidimeter.

Figure 13:
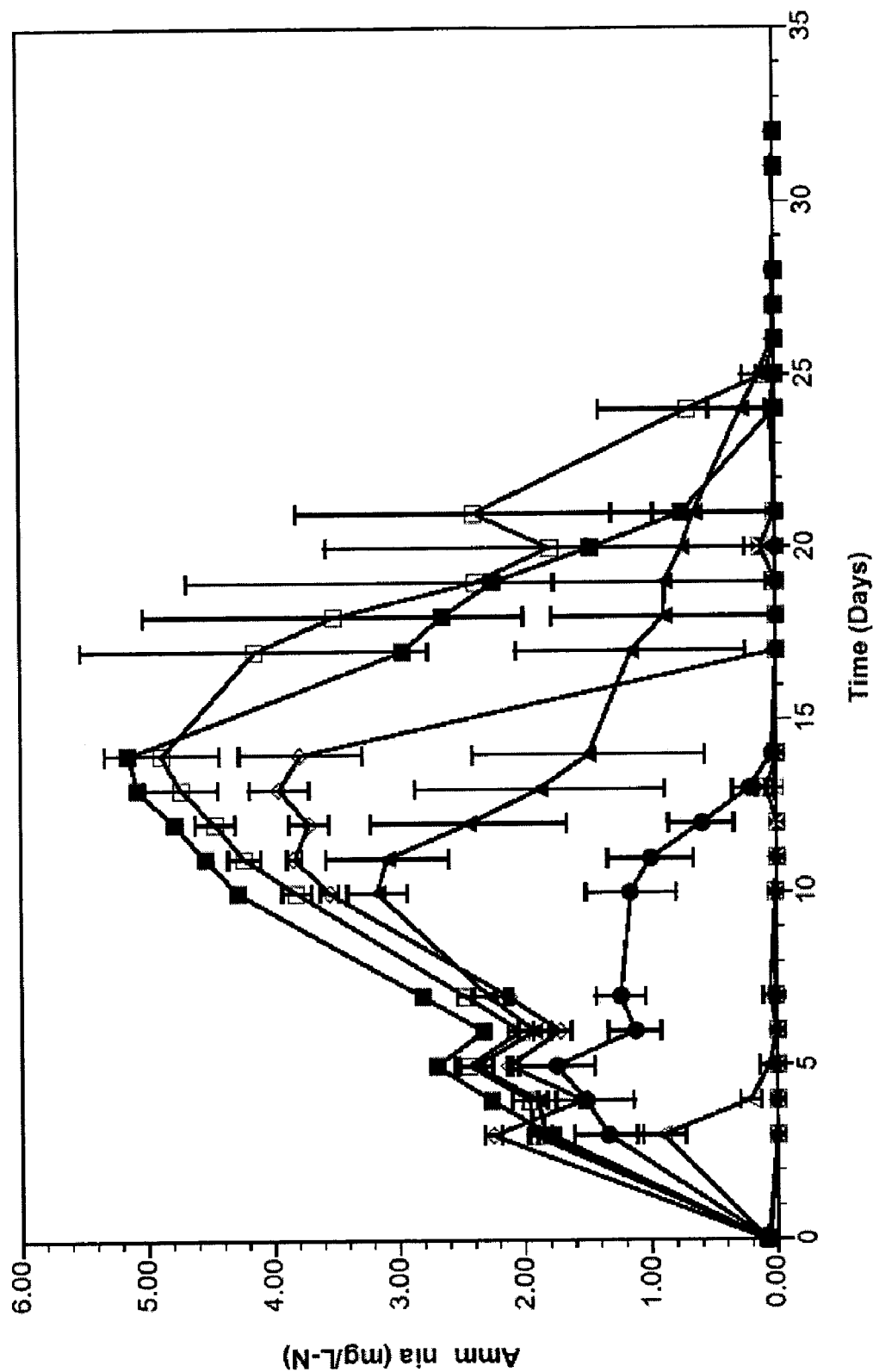
FIG. 13 illustrates mean ammonia concentration trends for a Bacterial Additives Test for assessing the viability of frozen saltwater bacterial strains that had been stored for 5 months and for assessing the viability of saltwater bacterial strains that had been stored in a liquid for 14 months.

FIG. 13 shows the mean ammonia values (N=4) for the various treatments in this test. The negative control (no addition of bacteria) took 25 days to reach a 0 mg/L concentration of ammonia. The ammonia in this treatment peaked on day 14 at a value of nearly 7 mg/L. In contrast to these values, all of the experimental aquaria, whether they received a frozen or liquid treatment, reach a 0 mg/L concentration of ammonia significantly faster (FIG. 13).

Figure 14:
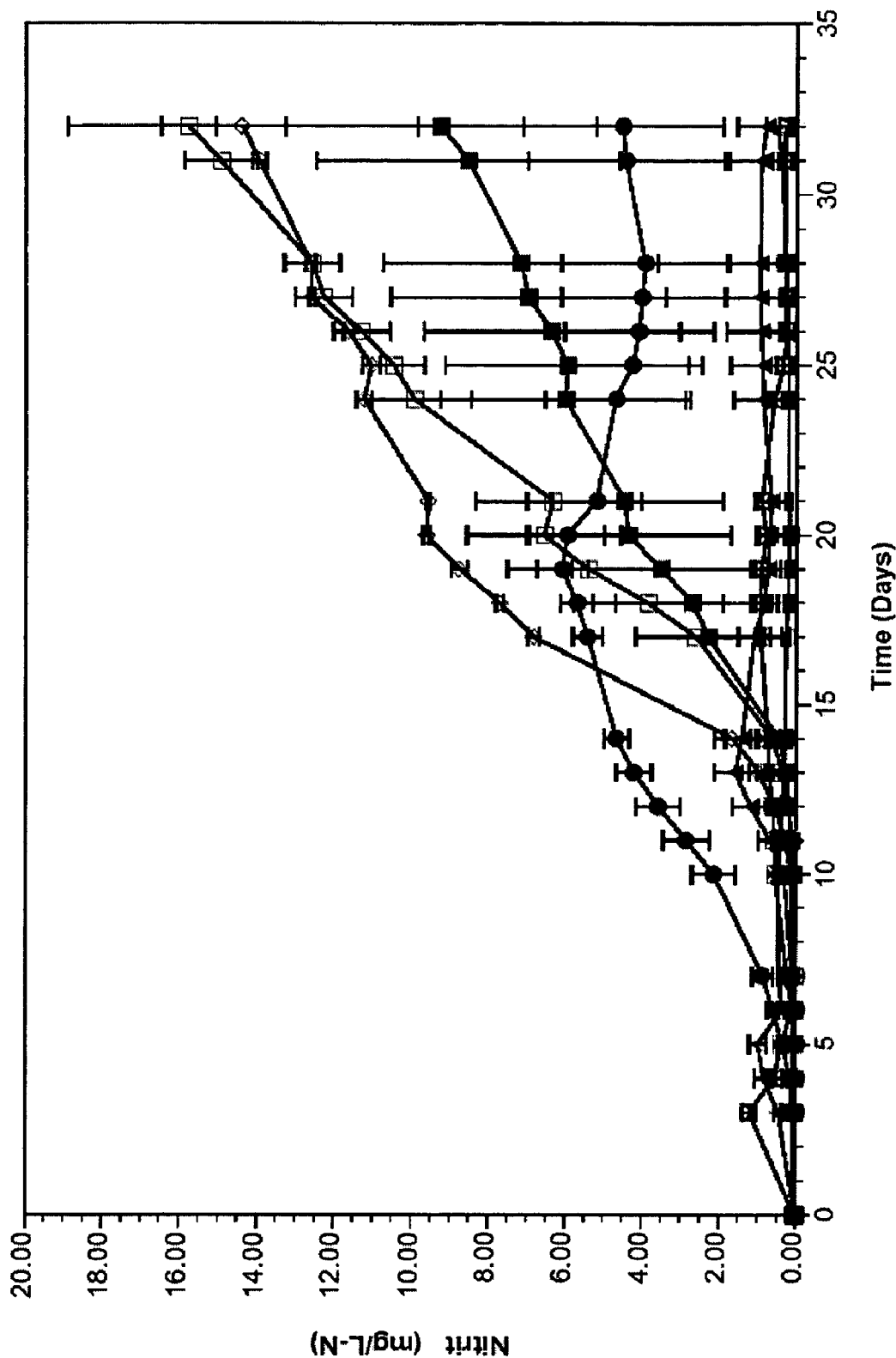
FIG. 14 illustrates mean nitrite concentration trends for a Bacterial Additives Test for assessing the viability of frozen saltwater bacterial strains that had been stored for 5 months and for assessing the viability of saltwater bacterial strains that had been stored in a liquid for 14 months.

FIG. 14 shows the mean nitrite values (N=4) for the various treatments in this test. Aquaria receiving the negative control and the treatment of liquid bacteria stored at 37° C. exhibited elevated nitrite levels that did not abate after more than 30 days. In contrast to these values, the remainder of the experimental aquaria, whether they received a frozen or liquid treatment, exhibited a reduction in nitrite concentration (FIG. 14).

Figure 15:
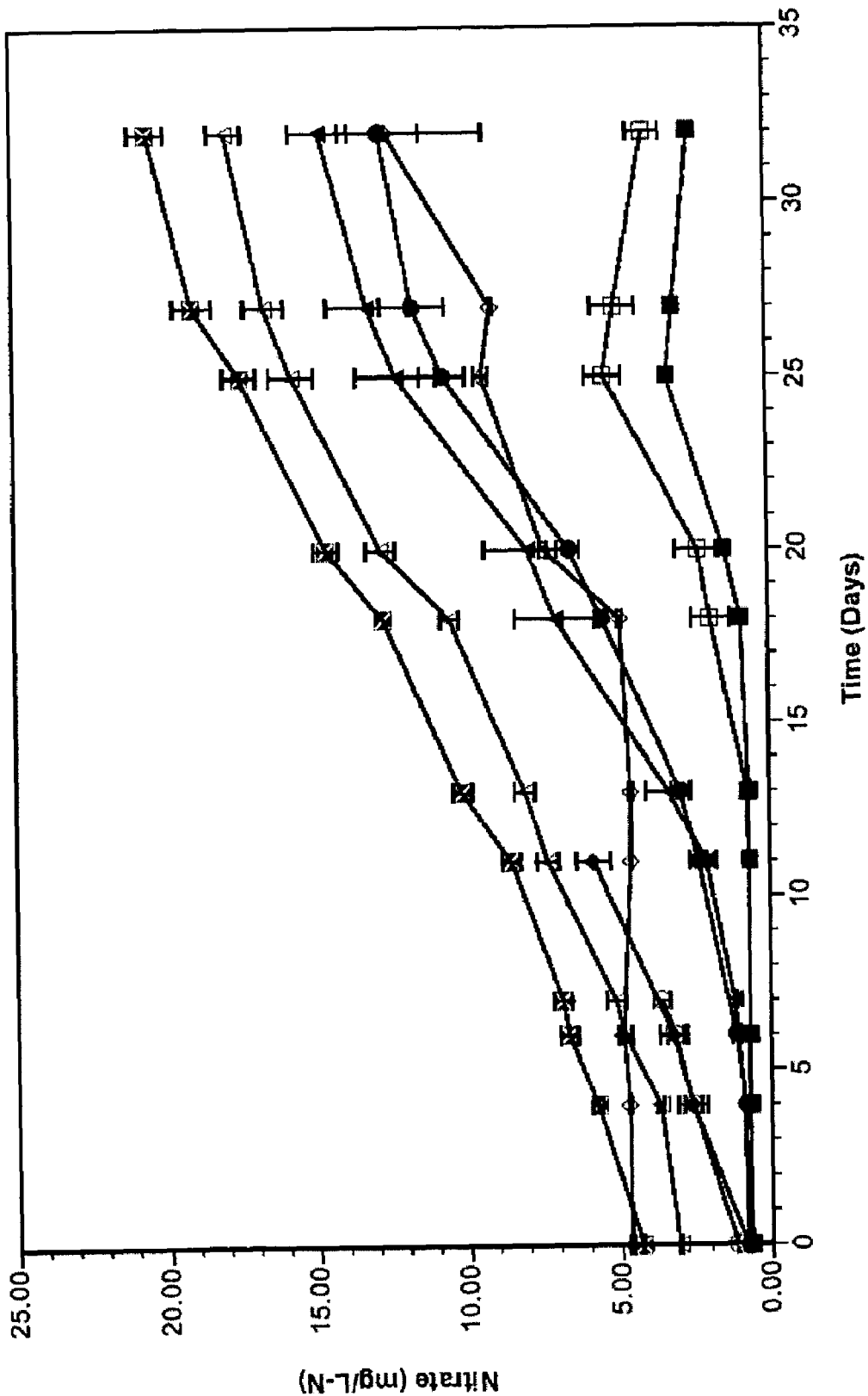
FIG. 15 illustrates mean nitrate concentration trends for a Bacterial Additives Test for assessing the viability of frozen saltwater bacterial strains that had been stored for 5 months and for assessing the viability of saltwater bacterial strains that had been stored in a liquid for 14 months.

FIG. 15 shows the mean nitrate values (N=4) for the various treatments in this test. All of the aquaria exhibited some increase in nitrate concentration over the course of the test. With the exception of the liquid cells stored at 37° C., aquaria receiving all of the frozen and liquid treatments showed a consistent, upward trend in nitrate concentration.

The results of this test demonstrate that frozen preparations of the NOB of the present invention maintain their ability to oxidize nitrite to nitrate after 5 months of frozen storage. The results of this test also demonstrate that the optimum frozen storage temperature for the NOB of the present invention is −80° C., but that −20° C. and −15° C. are also good storage temperatures.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning and range of equivalency of the claims are intended to be embraced therein.

What is claimed is:

1. A biologically pure culture of a bacterial strain that oxidizes nitrite to nitrate, wherein the 16S rDNA of the bacterial strain has a nucleotide sequence comprising SEQ ID NO:1.

2. A composition, comprising a concentrated isolated bacterial strain that oxidizes nitrite to nitrate wherein the 16S rDNA of the bacterial strain has a nucleotide sequence comprising SEQ ID NO:1.

3. The composition of claim 2, further comprising a microorganism selected from the group consisting of ammonia-oxidizing organisms, nitrite-oxidizing microorganisms, nitrate-reducing microorganisms, heterotrophic microorganisms and combinations thereof.

4. A composition comprising nitrite-oxidizing bacteria and ammonia-oxidizing bacteria, present in an approximately 1:3 ratio, wherein the nitrite-oxidizing bacteria comprises an isolated bacterial strain having 16S rDNA including a nucleotide sequence identical to SEQ ID NO:1.

* * * * *

SEQUENCE LISTING

<160> NUMBER OF SEQ ID NOS: 22

<210> SEQ ID NO 1
<211> LENGTH: 1495
<212> TYPE: DNA
<213> ORGANISM: Unknown
<220> FEATURE:
<223> OTHER INFORMATION: NOB SB7c32 16S rDNA

<400> SEQUENCE: 1

```
tgatcatggc tcagattgaa cgctggcggc atgcctaaca catgcaagtc gagcggcagc      60
agcgcctttc ttcggaaagg tggctggcga gcggcggacg ggtgagtaac gcgtgggaat     120
ctaccttcgg tgggggatag cccggggaaa ctcggattaa taccgcatac gcctacgggg     180
gaaagcgggc ctctgcttgc aagctcgcac cgatggatga gcccgcgtcc gattagctag     240
ttggtggggt aatggcctac caaggcgacg atcggtagct ggtctgagag gacgatcagc     300
cacactggga ctgagacacg gcccagactc ctacgggagg cagcagtggg gaatattgga     360
caatgggcgc aagcctgatc cagcaatgcc gcgtgggtga agaaggcctg cgggttgtaa     420
agcccttcca gtcgggagga aaagcatcgg gttaatacct cggtgtcttg acgttaccgg     480
cagaagaagc accggctaac tccgtgccag cagccgcggt aatacggagg gtgcaagcgt     540
taatcggaat tactgggcgt aaagcgcatg taggcggtcg gataagtcgg gtgtgaaagc     600
cccgggctca acctgggaat tgcatccgat actgtttggc tagagtctgg tagagggagg     660
cggaattccc ggtgtagcgg tgaaatgcgt agatatcggg aggaacacca gtggcgaagg     720
cggtctcctg gatcaagact gacgctgagg tgcgaaagcg tggggagcaa acaggattag     780
ataccctggt agtccacgcc gtaaacgatg aggactagcc gttggattca ttaatgagtc     840
tagtggcgca gctaacgcgt taagtcctcc gcctggggag tacggccgca aggttaaaac     900
tcaaaggaat tgacgggggc ccgcacaagc ggtggagcat gtggtttaat tcgatgcaac     960
gcgaagaacc ttacctgctc ttgacatctc cggaacctta cagagatgtg agggtgcctt    1020
cgggaaccgg atgacaggtg ctgcatggct gtcgtcagct cgtgtcgtga gatgttgggt    1080
taagtcccgc aacgagcgca acccttgccc ctagttacca gcggttcggc cggggactct    1140
agggggactg ccggtgacaa accggaggaa ggtgggatg acgtcaagtc atcatggccc    1200
ttatgggcag gctacacac gtgctacaat ggccggtaca aagggttgca aaccgtggag    1260
gggagctaat cccaaaaagc cggtcccagt ccggattgca gtctgcaact cgactgcatg    1320
aagtcggaat cgctagtaat cgcggatcag caatgccgcg gtgaatacgt tcccgggcct    1380
tgtacacacc gcccgtcaca ccatgggagt cggctgcacc agaagtcggt agcctaacct    1440
tcttaggaag gagggcgctg cccacggtgt ggtcgatgac tggggtgaag tcgta         1495
```

<210> SEQ ID NO 2
<211> LENGTH: 1450
<212> TYPE: DNA
<213> ORGANISM: Unknown
<220> FEATURE:
<223> OTHER INFORMATION: NOB SB7c11 16S rDNA

<400> SEQUENCE: 2

```
gatcatggct cagattgaac gctggcggca tgcctaacac atgcaagtcg agcggcagca      60
gcacctctct tcggaaaggt ggctggcgag cggcggacgg gtgagtaacg cgtgggaatc     120
taccttcggt gggggatagc ccggggaaac tcggattaat accgcatacg cctacggggg     180
```

```
aaagcgggcc tctgcttgca agctcgcacc gatggatgag cccgcgaccg attagctagt        240
tggtggggta acggcctacc aaggcgacga tcggtagctg gtctgagagg acgatcagcc        300
acactgggac tgagacacgg cccagactcc tacgggaggc agcagtgggg aatattggac        360
aatgggcgca agcctgatcc agcaatgccg cgtgggtgaa gaaggcctgc gggttgtaaa        420 gcccttcag ccgggaggaa aagcatcggg ttaataccctc gatgtgttga cgttaccggc         480
agaagaagca ccggctaact ccgtgccagc agccgcggta atacggaggg tgcaagcgtt        540
aatcggaatt actgggcgta aagcgcatgt aggcggtcgg ataagtcggg tgtgaaagcc        600
ccgggctcaa cctgggaatt gcatccgata ctgtttgtct agagtctggt agagggaggc        660 ggaattccg gtgtagcggt gaaatgcgta gatatcggga ggaacaccag tggcgaaggc         720
ggtctcctgg atcaagactg acgctgaggt gcgaaagcgt ggggagcaaa caggattaga       780 tacccctggta gtccacgccg taaacgatga ggactagccg ttggattcat taatgagtct      840
agtggcgcag ctaacgcgtt aagtcctccg cctggggagt acggccgcaa ggttaaaact       900
caaaggaatt gacggggggcc cgcacaagcg gtggagcatg tggtttaatt cgatgcaacg      960
cgaagaacct tacctgctct tgacatctcc ggaaccttgc agagatgtga gggtgccttc      1020
gggaaccgga tgacaggtgc tgcatggctg tcgtcagctc gtgtcgtgag atgttgggtt      1080
aggtcccgca acgagcgcaa cccttgcccc tagttaccag cggttcggcc ggggactcta      1140
gggggactgc cggtgacaaa ccggaggatg tggggatga cgtcaagtca tcatggccct       1200
tatgagcagg gctacacacg tgctacaatg gccggtacaa agggttgcaa accgtgaggg     1260
ggagctaatc ccaaaaagcc ggtcccagtc cggattgcag tctgcaactc gactgcatga      1320
agtcggaatc gctagtaatc gcggatcagc aatgccgcgg tgaatacgtt cccgggcctt      1380
gtacacaccg cccgtcacac catgggagtc ggctgcacca gaagtcggta gcctaacctt       1440
cttaggaagg                                                            1450

<210> SEQ ID NO 3
<211> LENGTH: 1445
<212> TYPE: DNA
<213> ORGANISM: Unknown
<220> FEATURE:
<223> OTHER INFORMATION: NOB SB7c136 16S rDNA

<400> SEQUENCE: 3
tgatcatggc tcagaacgaa cgctggcggc gcgcctaaca catgcaagtc gaacgagaat         60
ccggggcaac tcggtagtaa agtggcaaac gggtgaggaa tacatgggta acctgcccttt      120 gagaagggaa taccccgccg aaaggtgagc taatacccta tacgctatca tttttacgaa       180
aaagatagga aagccaagtc gaggacttgg tactcaagga ggggctcatg tcctatcagc      240
ttgttggtgg ggtaacggcc taccaaggct acgacgggta gctggtctga gaggatgatc     300
agccacactg gcactgagat acgggccaga ctcctacggg aggcagcagt gaggaatatt       360
gcgcaatggg cgaaagcctg acgcagcgac gccgcgtggg ggatgaaggt tttcggattg       420 taaaccccctt tcatgaggaa agataaagtg gtaaccact tagacggtac ctcaagaaga      480
agccacggct aacttcgtgc cagcagccgc ggtaatacga wggtggcgag cgttgttcgg      540
atttactggg cgtaaagagc acgtaggcgg ttgggaaagc cttttgggaa atctcccggc      600
ttaaccggga aaggtcgaga ggaactactg agctagagga cggagagga gcgcggaatt      660 cccggtgtag cggtgaaatg cgtagatatc gggaagaagg ccggtggcga aggcggcgct      720
```

```
ctggaacgta cctgacgctg aggtgcgaaa gcgtggggag caaacaggat tagataccct      780
ggtagtccac gccctaaacg atgggtacta agtgtcggcg gtttaccgtc ggtgccgcag      840
ctaacgcagt aagtaccccg cctggggagt acggccgcaa ggttgaaact caaaggaatt      900
gacgggggcc cgcacaagcg gtggagcatg tggtttaatt cgacgcaacg cgaggaacct      960
tacccaggtt ggacatgctc gtggtacgaa cctgaaaggg tgaggacctc gaaaggggag     1020
cgagctcagg tgctgcatgg ctgtcgtcag ctcgtgccgt gaggtgttgg gttaagtccc     1080
gcaacgagcg taaccnctgt cttcagttgc catcgggtca tgccgagcac tctgaagaga     1140
ctgcccagga taacggggag aaggtgggga tgacgtcaa gtcagcatgg cctttatgcc     1200
tggggctaca cacgtgctac aatgaccggt acagagggtt gcaatcccgc aaggggagc     1260 caatctcaaa aaaccggcct cagttcagat tggggtctgc aactcgaccc catgaaggtg     1320
gaatcgctag taatcgcgga tcagcacgcc gcggtgaata cgttcccggg ccttgtacac     1380
accgcccgtc acaccacgaa agtcagctgt accagaagtc actggcgcca acctgcaagg     1440
gaggc                                                                1445

<210> SEQ ID NO 4
<211> LENGTH: 1450
<212> TYPE: DNA
<213> ORGANISM: Unknown
<220> FEATURE:
<223> OTHER INFORMATION: NOB SB7c47 16S rDNA

<400> SEQUENCE: 4
tgatcatggc tcagaacgaa cgctggcggc gcgcctaaca catgcaagtc gaacgagaat       60
ccggggcaac tcggtagtaa agtggcaaac gggtgaggaa cacatgggta acctgccctt      120
gagaagggaa taacccgccg aaaggtgagc taatacccta tacgctatca tttttacgaa      180
aaagatagga agccaagtc gaggacttgg tactcaagga ggggctcatg tcctatcagc      240
ttgttggtgg ggtaacggcc taccaaggct acgacgggta gctggtctga gaggatgatc      300
agccacactg gcactgagat acgggccaga ctcctacggg aggcagcagt gaggaatatt      360
gcgcaatggg cgaaagcctg acgcagcgac gccgcgtggg ggatgaaggt cttcggattg      420 taaaccccctt tcatgaggaa agataaagtg ggtaaccact tagacggtac ctcaagaaga      480
agccacggct aacttcgtgc cagcagccgc ggtaatacga aggtggcgag cgttgttcgg      540
atttactggg cgtaaagagc acgtaggcgg ttgggaaagc cttttgggaa atctcccggc      600
ttaaccggga aaggtcgaga ggaactactc agctagagga cggagaggac gcgcggaatt      660
cccggtgtag cggtgaaatg cgtagatatc gggaagaagg ccggtggcga aggcggcgct      720
ctggaacgta cctgacgctg aggtgcgaaa gcgtggggag caaacaggat tagataccct      780
ggtagtccac gccctaaacg atgggtacta agtgtcggcg gtttaccgtc ggtgccgcag      840
ctaacgcagt aagtaccccg cctggggagt acggccgcaa ggttgaaact caaaggaatt      900
gacgggggcc cgcacaagcg gtggagcatg tggtttaatt cgacgcaacg cgaagaacct      960
tgcccaggtt ggacatgctc gtggtacgaa cctgaaaggt gaggacctcg aaaggggagc     1020
gagctcaggt gctgcatggc tgtcgtcagc tcgtgccgtg aggtgttggg ttaagtcccg     1080
caacgagcgt aaccnctgtc ttcagttgcc atcgggtcat gccgagcact ctgaagagac     1140
tgcccaggat aacggggagg aaggtgggga tgacgtcaag tcagcatggc ctttatgcct     1200
ggggctacac acgtgctaca atgaccggta cagagggttg caatcccgca aggggagcc     1260 aatctcaaaa aaccggcctc agttcagatt ggggtctgca actcgacccc atgaaggtgg     1320
```

```
aatcgctagt aatcgcggat cagcacgccg cggtgaatac gttcccgggc cttgtacaca    1380
ccgcccgtca caccacgaaa gtcagctgta ccagaagtca ctggcgccaa cctgcaaggg    1440
agggcaggtg                                                          1450

<210> SEQ ID NO 5
<211> LENGTH: 1473
<212> TYPE: DNA
<213> ORGANISM: Unknown
<220> FEATURE:
<223> OTHER INFORMATION: NOB R21c76 16S rDNA

<400> SEQUENCE: 5
gaacgaacgc tggcggcgcg cctaacacat gcaagtcgaa cgagaatccg gggcaacccg      60
gtagtaaagt ggcaaacggg tgaggaatgc atgggcaacc tgcccttgag aagggaataa    120
cccgccgaaa ggtgggctaa taccctatac gctatcttct tttcggaaaa gataggaaag    180
cttggtcgag gactcggcac tcaaggaggg gctcatgtcc tatcagcttg ttggtggggt    240
aacggcctac caaggctacg acgggtagct ggtctgagag gatgatcagc cacactggca    300
ctgagatacg ggccagactc ctacggagg cagcagtgag gaatattgcg caatgggcga    360
aagcctgacg cagcgacgcc gcgtgggga tgaaggtttt cggattgtaa accccttca    420 tgaggaaaga taaagtgggt aaccacttag acggtacctc aagaagaagc cacggctaac    480
ttcgtgccag cagccgcggt aatacgaagg tggcaagcgt tgttcggatt tactgggcgt    540
aaagagcacg taggcggttg ggaaagcctc ttgggaaatc tcccggctta accgggaaag    600
ttcgagaggt actattcagc tagaggacgg gagaggagcg cggaattccc ggtgtagcgg    660
tgaaatgcgt agatatcggg aagaaggccg gtggcgaagg cggcgctctg gaacgtacct    720
gacgctgagg tgcgaaagcg tggggagcaa acaggattag ataccctggt agtccacgcc    780
ctaaacgatg ggtactaagt gtcggcggtt taccgtcggt gccgcagcta acgcagtaag    840
taccccgcct ggggagtacg gccgcaaggt tgaaactcaa aggaattgac ggggccgcgc    900
acaagcggtg gagcatgtgg tttaattcga cgcaacgcga agaaccttac ccaggttgga    960
catgctcgtg gtacgaacct gaaagggtga ggaccttgaa agaggagcga gctcaggtgc   1020
tgcatggctg tcgtcagctc gtgccgtgag gtgttgggtt aagtcccgca acgagcgtaa   1080
cccctgtctt cagttgccat cgggtcatgc cgagcactct gaagagactg cccaggataa   1140
cggggaggaa ggtggggatg acgtcaagtc agcatggcct ttatgcctgg ggctacacac   1200
gtgctacaat gaccggtaca gagggttgca atcccgcaag ggggagccaa tctcaaaaaa   1260
ccggcctcag ttcagattgg ggtctgcaac tcgaccccat gaaggtggaa tcgctagtaa   1320
tcgcggatca gcacgccgcg gtgaatacgt tcccgggcct tgtacacacc gcccgtcaca   1380
ccacgaaagt cagctgtacc agaagtcact ggcgccaacc cgcaaggggg gcaggtgccc   1440
aaggtatggt tggtaattgg ggtgaagtcg taa                                1473

<210> SEQ ID NO 6
<211> LENGTH: 1473
<212> TYPE: DNA
<213> ORGANISM: Unknown
<220> FEATURE:
<223> OTHER INFORMATION: NOB R21c28 16S rDNA

<400> SEQUENCE: 6
atcctggctc agaacgaacg ctgcggcgcg cctaacacat gcaagtcgaa cgagaatccg      60
```

-continued

| | |
|---|---|
| ggcaacctgg tagtaaagtg gcgaacgggt gaggaataca tgggtaacct gcccttgaga | 120 |
| atggaataac ctatcgaaag atgggctaat accatatacg cttcctgatt cgaggattgg | 180 |
| gaaggaaagt cgtatcgagg atacggcgtt caaggagggg ctcatggcct atcagcttgt | 240 |
| tggtggggta acggcctacc aaggcaacga cgggtagctg gtctgagagg atgatcagcc | 300 |
| acactggcac tgagatacgg gccagactcc tacgggaggc agcagtgagg aatattgcgc | 360 |
| aatgggcgaa agcctgacgc agcgacgccg cgtgggggat gaaggttttc ggattgtaaa | 420 |
| cccctttcag gaggaaagat aaggcaggtt actgcctgga cggtacctcc agaagaagcc | 480 |
| acggctaact cgtgccagc agccgcggta atacgaaggt ggcgagcgtt gttcggattt | 540 |
| actgggcgta aagagcgcgt aggcggttag gtaagcctct tgtggaatct ccggcttaac | 600 |
| cgggaatagt cgagggtaac tgcttagcta gagggcggga gaggagtgcg gaattcccgg | 660 |
| tgtagcggtg aaatgcgtag atatcgggaa gaaggccggt ggcgaaggcg cactctgga | 720 |
| acgcacctga cgctgaggcg cgaaagcgtg gggagcaaac aggattagat accctggtag | 780 |
| tccacgccct aaacgatggg cactaagtgt cggcggttta ccgccggtgc cgcagctaac | 840 |
| gcagtaagtg ccccgcctgg ggagtacggc cgcaaggttg aaactcaaag gaattgacgg | 900 |
| gggcccgcac aagcggtgga gcatgtggtt taattcgacg caacgcgaag aaccttaccc | 960 |
| aggttggaca tgcaagtagt aagaacctga aaggggatg agcccgcaag gcagcttgc | 1020 |
| tcaggtgctg catggctgtc gtcagctcgt gccgtgaggt gttggttaag tcccgcaacg | 1080 |
| agcgtaaccc ctgtcttcag ttgccatcgg gtcatgccgg gcactctgga gagactgccc | 1140 |
| aggataacgg ggaggaaggt ggggatgacg tcaagtcagc atggccttta tgcctggggc | 1200 |
| tacacacgtg ctacaatgac cggtacaaag ggttgcaatc ccgcaagggt gagctaatct | 1260 |
| caaaaaacca gtctcagttc ggatcgcagt ctgcaactcg actgcgtgaa gctggaatcg | 1320 |
| ctagtaatcg gagatcagca cgctccgatg aatacgttcc cgggccttgt acacaccgcc | 1380 |
| cgtcacacca tgggagtcgg ctgctccaga gtagttatc ttaacccgca aggagggagg | 1440 |
| ctaccaagga tcggtcggtg actggggtga agt | 1473 |

<210> SEQ ID NO 7
<211> LENGTH: 1480
<212> TYPE: DNA
<213> ORGANISM: Unknown
<220> FEATURE:
<223> OTHER INFORMATION: NOB B7c10 16S rDNA

<400> SEQUENCE: 7

| | |
|---|---|
| catggctcag aacgaacgct gcggcgcgcc taacacatgc aagtcgaacg agaatccggg | 60 |
| gcaactcggt agtaaagtgg cgaacgggtg aggaatacat gggtaacctg cccttgaaag | 120 |
| tggaataacc tatcgaaaga tgggctaata ccatatacgc ttcctagttt gcggattagg | 180 |
| aaggaaagtc gtatcgagga tacggtgttc aaggaggggc tcatggccta tcagcttgtt | 240 |
| ggtggggtaa tggcctacca aggcaacgac gggtagctgg tctgagagga tgatcagcca | 300 |
| cactggcact gagatacggg ccagactcct acggaggca gcagtgagga atattgcgca | 360 |
| atgggcgaaa gcctgacgca gcgacgccgc gggggggatg aaggttttcg gattgtaaac | 420 |
| cccttccagg agggaagaaa aagcgggtaa ccgcccggac ggtacctcca gaagaagcca | 480 |
| cggctaactt cgtgccagca gccgcggtaa tacgaaggtg gcgagcgttg ttcggattta | 540 |
| ctgggcgtaa agagcgcgta ggcggttagg taagcctctt gtgaaagctc ccggcttaac | 600 |
| cgggaatggt cgaggggaac tacttagcta gagggcggga gaggagtgcg gaattcccgg | 660 |

```
tgtagcggtg aaatgcgtag atatcgggaa gaaggccggt ggcgaaggcg gcactctgga      720
acgcacctga cgctgaggcg cgaaagcgtg gggagcaaac aggattagat accctggtag      780
tccacgccct aaacgatggg cactaagtgt cggcggttta ccgtcggtgc cgcagctaac      840
gcagtaagtg ccccgcctgg ggagtacggc cgcaaggttg aaactcaaag gaattgacgg      900
gggcccgcac aagcggtgga gcatgtggtt taattcgacg caacgcgaag aaccttaccc      960
aggttggaca tgcaagtagt aagaacctga aggggatga gcccgcaagg agcttgctca     1020
ggtgctgcat ggctgtcgtc agctcgtgcc gtgaggtgtt gggttaagtc ccgcaacgag     1080
cgtaacccct gtcttcagtt gccatcgggt catgccgggc actctggaga gactgcccag     1140
gataacgggg aggaaggtgg ggatgacgtc aagtcagcat ggcctttatg cctggggcta     1200
cacacgtgct acaatgaccg gtacaaaggg ttgcaatccc gtaaggggga gctaatctca     1260
aaaaaccggc ctcagttcag attggggtct gcaactcgac cccatgaagg tggaatcgct     1320
agtaatcggg gatcagcacg ccgcggtgaa tacgttcccg ggccttgtac atattgtccg     1380
tcacagcacg aaagtcagct gtaccagaag ttgctggcgc taacccgtaa ggaggcaggt     1440
gcccaaggta tggttggtaa ttggggtgaa gtcgtaacaa                           1480

<210> SEQ ID NO 8
<211> LENGTH: 1490
<212> TYPE: DNA
<213> ORGANISM: Unknown
<220> FEATURE:
<223> OTHER INFORMATION: NOB B7c7 16S rDNA

<400> SEQUENCE: 8
tttgatcatg gctcagaacg aacgctggcg gcgcvvctaa cacatgcaag tcgaacgaga       60
atccggggca actcggtagt aaagtggcga acgggtgagg aatacatggg taacctgccc      120
ttgaaagtgg aataacctat cgaaagatgg gctaatacca tatacgcttc ctagtttgcg      180
gattaggaag gaaagtcgta tcgaggatac ggtgttcaag gagggctca tggcctatca       240 gcttgttggt ggggtaatgg cctaccaagg caacgacggg tagctggtct gagaggatga      300
tcagccacac tggcactgag atacgggcca gactcctacg ggaggcagca gtgaggaata      360
ttgcgcaatg ggcgaaagcc tgacgcagcg acgccgcgtg ggggatgaag gttttcggat      420
tgtaaacccc tttcaggagg gaagaaaaag cgggtaaccg cccggacgat acctccagaa      480
gaagccacag ctaacttcgt gccagcaacc gcggtaatac aagggtagcg aacgttgttc      540
aaatttacta ggcgtaaaga gcacatagac aattaggtaa gcctcttgtg aaagctcccg      600
gcttaaccgg gaatggtcga gggaactac ttagctagaa acaggagaa aagtacgaaa       660 ttcccaatat aacaataaaa tacataaata tcaaaagaa ggccggtggc gaaggcggca      720
ctctggaacg cacctgacgc tgaggcgcga aagcgtgggg agcaaacagg attagatacc      780
ctggtagtcc acgccctaaa cgatgggcac taagtgtcgg cggtttaccg tcggtgccgc      840
agctaacgca gtaagtgccc cgcctgggga gtacggccgc aaggttgaaa ctcaaaggaa      900
ttgacggggg cccgcacaag cggtggagca tgtggtttaa ttcgacgcaa cgcgaagaac      960
cttacccagg ttggacatgc aagtagtaag aacctgaaag gggatgagcc cgcaaggagc     1020
ttgctcaggt gctgcatagc tgtcgtcaac tcgtgccata agtgttggg ttaagtccca      1080 caacaagcgt aaccctgtc ttcagttgcc atcgggtcat gccgggcact ctggagagac      1140
tgcccaggat aacggggagg aaggtgggga tgacgtcaag tcagcatggc ctttatgcct     1200
```

```
ggggctacac acgtgctaca atgaccggta caaaggggttg caatcccgta agggggagct    1260
aatctcaaaa aaccggcctc agttcagatt ggggtctgca actcgacccc atgaaggtgg    1320
aatcgctagt aatcgcggat cagcacgccg cggtgaatac gttcccgggc cttgtacaca    1380
ccgcccgtca caccgaaa gtcagctgta ccagaagtcg ctggcgctaa cccgtaagga    1440
ggcaggtgcc caaggtatgg ttggtaattg gggtgaagtc gtaacaaggt               1490
```

```
<210> SEQ ID NO 9
<211> LENGTH: 17
<212> TYPE: DNA
<213> ORGANISM: Artificial
<220> FEATURE:
<223> OTHER INFORMATION: PCR Primer

<400> SEQUENCE: 9
gtttgatcct ggctcag                                                   17

<210> SEQ ID NO 10
<211> LENGTH: 19
<212> TYPE: DNA
<213> ORGANISM: Artificial
<220> FEATURE:
<223> OTHER INFORMATION: PCR Primer

<400> SEQUENCE: 10
ggttaccttg ttacgactt                                                 19

<210> SEQ ID NO 11
<211> LENGTH: 17
<212> TYPE: DNA
<213> ORGANISM: Artificial
<220> FEATURE:
<223> OTHER INFORMATION: PCR Primer

<400> SEQUENCE: 11
cctacgggag gcagcag                                                   17

<210> SEQ ID NO 12
<211> LENGTH: 18
<212> TYPE: DNA
<213> ORGANISM: Artificial
<220> FEATURE:
<223> OTHER INFORMATION: PCR Primer

<400> SEQUENCE: 12
gwattaccgc ggckgctg                                                  18

<210> SEQ ID NO 13
<211> LENGTH: 22
<212> TYPE: DNA
<213> ORGANISM: Artificial
<220> FEATURE:
<223> OTHER INFORMATION: PCR Primer

<400> SEQUENCE: 13
caccgggaat tccgcgctcc tc                                             22

<210> SEQ ID NO 14
<211> LENGTH: 20
<212> TYPE: DNA
<213> ORGANISM: Artificial
<220> FEATURE:
<223> OTHER INFORMATION: Oligonucleotide Probe

<400> SEQUENCE: 14
```

```
gttgccccgg attctcgttc                                              20

<210> SEQ ID NO 15
<211> LENGTH: 22
<212> TYPE: DNA
<213> ORGANISM: Artificial
<220> FEATURE:
<223> OTHER INFORMATION: Oligonucleotide Probe

<400> SEQUENCE: 15
caccgggaat ccgcgctcc tc                                            22

<210> SEQ ID NO 16
<211> LENGTH: 22
<212> TYPE: DNA
<213> ORGANISM: Artificial
<220> FEATURE:
<223> OTHER INFORMATION: Oligonucleotide Probe

<400> SEQUENCE: 16
caccgggaat ccgcactcc tc                                            22

<210> SEQ ID NO 17
<211> LENGTH: 18
<212> TYPE: DNA
<213> ORGANISM: Artificial
<220> FEATURE:
<223> OTHER INFORMATION: Oligonucleotide Probe

<400> SEQUENCE: 17
gctgcctccc gtaggagt                                                18

<210> SEQ ID NO 18
<211> LENGTH: 21
<212> TYPE: DNA
<213> ORGANISM: Artificial
<220> FEATURE:
<223> OTHER INFORMATION: Oligonucleotide Probe

<400> SEQUENCE: 18
ctcgccagcc acctttccga a                                            21

<210> SEQ ID NO 19
<211> LENGTH: 17
<212> TYPE: DNA
<213> ORGANISM: Artificial
<220> FEATURE:
<223> OTHER INFORMATION: PCR Primer

<400> SEQUENCE: 19
tccggggcaa ccyggta                                                 17

<210> SEQ ID NO 20
<211> LENGTH: 16
<212> TYPE: DNA
<213> ORGANISM: Artificial
<220> FEATURE:
<223> OTHER INFORMATION: PCR Primer

<400> SEQUENCE: 20
tcmccctttc aggttc                                                  16

<210> SEQ ID NO 21
<211> LENGTH: 21
<212> TYPE: DNA
```

-continued

```
<213> ORGANISM: Artificial
<220> FEATURE:
<223> OTHER INFORMATION: PCR Primer

<400> SEQUENCE: 21
ttcggaaagg tggctggcga g                                              21

<210> SEQ ID NO 22
<211> LENGTH: 20
<212> TYPE: DNA
<213> ORGANISM: Artificial
<220> FEATURE:
<223> OTHER INFORMATION: PCR Primer

<400> SEQUENCE: 22
atctctgyaa ggttccggag                                                20
```